US008389797B2

(12) United States Patent
Concibido et al.

(10) Patent No.: US 8,389,797 B2
(45) Date of Patent: Mar. 5, 2013

(54) METHODS TO IDENTIFY SOYBEAN APHID RESISTANT QUANTITATIVE TRAIT LOCI IN SOYBEAN AND COMPOSITIONS THEREOF

(75) Inventors: Vergel Concibido, Maryland Heights, MO (US); James Narvel, Middletown, DE (US); Jennifer Yates, Elkton, MD (US); Henry Roger Boerma, Athens, GA (US)

(73) Assignees: University of Georgia Research Foundation, Inc., Athens, GA (US); Monsanto Technology LLC, St. Louis, MO (US)

( * ) Notice: Subject to any disclaimer, the term of this patent is extended or adjusted under 35 U.S.C. 154(b) by 792 days.

(21) Appl. No.: 12/187,502

(22) Filed: Aug. 7, 2008

(65) Prior Publication Data

US 2009/0049565 A1     Feb. 19, 2009

Related U.S. Application Data

(60) Provisional application No. 60/963,936, filed on Aug. 8, 2007.

(51) Int. Cl.
| | |
|---|---|
| *A01H 1/00* | (2006.01) |
| *A01H 1/02* | (2006.01) |
| *A01H 5/00* | (2006.01) |
| *C12N 5/04* | (2006.01) |

(52) U.S. Cl. ........ 800/265; 800/312; 800/302; 800/267; 435/468

(58) Field of Classification Search ........................ None
See application file for complete search history.

(56) References Cited

U.S. PATENT DOCUMENTS

| | | |
|---|---|---|
| 2005/0249769 A1 | 11/2005 | Zhu et al. |
| 2006/0015964 A1 | 1/2006 | Hill |
| 2006/0277627 A1 | 12/2006 | Wang et al. |
| 2006/0288444 A1 | 12/2006 | McCarroll et al. |
| 2007/0039065 A1 | 2/2007 | Laurie |
| 2009/0241214 A1 | 9/2009 | Wang et al. |
| 2010/0024073 A1 | 1/2010 | Wang et al. |
| 2012/0174246 A1 | 7/2012 | Chaky et al. |

FOREIGN PATENT DOCUMENTS

WO    WO 2006/125065    11/2006

OTHER PUBLICATIONS

Mensah, C; et al. Resistance to soybean aphid in early maturing soybean germplasm, Crop Science, 45 (6): 2228-2233 Nov.-Dec. 2005.
Hill, CB; Li, Y; Hartman, GL; Soybean aphid resistance in soybean Jackson is controlled by a single dominant gene, Crop Science, 46 (4): 1606-1608 Jul.-Aug. 2006.
Hill, CB; Li, Y; Hartman, GL; A single dominant gene for resistance to the soybean aphid in the soybean cultivar Dowling, Crop Science, 46 (4): 1601-1605 Jul.-Aug. 2006.
Narvel et al. A retrospective DNA marker assessment of the development of insect resistant soybean. Crop Science 41:1931-1939. 2001.
Venette et al. Assessing the Invasion by Soybean Aphid (Homoptera: Aphididae): Where Will It End?. Annals of the Entomological Society of America 97: 219-226. 2004.
Ha et al., Development of SNP Assays for Marker-Assisted Selection of Two Southern Root-Knot Nematode Resistance QTL in Soybean, Crop Science 47:S73-S82 (2007).
Mensah, Inheritance of Soybean Aphid Resistance in PI 567541B and PI567598B, ASA-CSSA-SSSA, 2006 International Meetings.
Mensah, Identification of QTLs Underlying Soybean Aphid Resistance in PI 567598B, ASA-CSSA-SSSA, 2006 International Meetings.
Rafalski, Applications of single nucleotide polymorphisms in crop genetics, Current Opinion in Plant Biology, 5:94-100 (2002).
Kim et al., "Identification of a New Soybean Aphid Biotype", ASA-CSSA-SSSA 2007 International Annual Meetings, Nov. 6, 2007, p. 159-3.
Hesler et al., "Characterization of Resistance to Aphis Glycines in Soybean Accessions", Euphytica, 2007, pp. 91-99, vol. 154, published online Oct. 17, 2006.
Curtis B. Hill et al., Resistance to the Soybean Aphid in Soybean Germplasm, Crop Science Society of America, 44:98-106 (2004), Madison, WI.
Soybean Aphid Research Update, pp. 1-12, North Central Soybean Research Program (2008).
Article entitled Aphid-resistant soybeans are a new option by Top Crop Manager, pp. 1-4, May 19, 2009 from http://www.toperopmanager.com/content/view/4424/67/.
Sinclair and Backman, Compendium of Soybean Disease, 3rd Ed. APS Press, St. Paul, MN, p. 1 (1989).
Cox et al., Relationship Between Coefficient of Parentage and Genetic Similarity Indices in the Soybean, Crop Sci. 25:529-532 (1985).
Vennette et al., Assessing the Invasion by Soybean Aphid (Homoptera: Aphididae): Where Will It End?, Annals of the Entomological Society of America, 97(2):219-226 (Mar. 2004).
Wang et al., Plant Protection 4, 20:12-13 (1994).
Landis et al., NCR-125 Arthropod Biological Control: State Reports for 2003. http://www.ncera125.ent.msu.edu/StateRpts2003MI.htm.
Li et al., Soybean aphid resistance genes in the soybean cultivars Dowling and Jackson map to linkage group M, Mol Breeding, 19:25-34 (2007).
Gomez et al., Diurnal pattern of aphid feeding and its effect on cotton leaf physiology, Environmental and Experimental Botany, 55:77-86 (2006).
Wang et al., Aphis glycines as a Vector of Persistently and Nonpersistently Transmitted Viruses and Potential Risks for Soybean and Other Crops, Plant Disease 90:920-926 (Jul. 2006).
Kim et al., Discovery of Soybean Aphid Biotypes, Crop. Sci. 48:923-928 (2008).

*Primary Examiner* — Medina A Ibrahim
(74) *Attorney, Agent, or Firm* — Thompson Coburn LLP; William A. Holtz

(57) ABSTRACT

The present invention is in the field of plant breeding and aphid resistance. More specifically, the invention includes a method for breeding soybean plants containing quantitative trait loci that are associated with resistance to aphids, *Aphis glycines*. The invention further includes method for monitoring the introgression quantitative trait loci (QTL) conferring aphid resistance into elite germplasm in a breeding program.

11 Claims, No Drawings

```
                            SEQUENCE LISTING

<160> NUMBER OF SEQ ID NOS: 200

<210> SEQ ID NO 1
<211> LENGTH: 27
<212> TYPE: DNA
<213> ORGANISM: Artificial Sequence
<220> FEATURE:
<223> OTHER INFORMATION: synthetic primer

<400> SEQUENCE: 1
gatggaggtc atgagttaga atctttt                                            27

<210> SEQ ID NO 2
<211> LENGTH: 27
<212> TYPE: DNA
<213> ORGANISM: Artificial Sequence
<220> FEATURE:
<223> OTHER INFORMATION: synthetic primer

<400> SEQUENCE: 2
ggtcacttag tcaatgacaa cacaatt                                            27

<210> SEQ ID NO 3
<211> LENGTH: 25
<212> TYPE: DNA
<213> ORGANISM: Artificial Sequence
<220> FEATURE:
<223> OTHER INFORMATION: synthetic primer

<400> SEQUENCE: 3
tgttcatgtc accactctcc aagta                                              25

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
gcatgcaatc agctctccaa                                                    20

<210> SEQ ID NO 5
<211> LENGTH: 29
<212> TYPE: DNA
<213> ORGANISM: Artificial Sequence
<220> FEATURE:
<223> OTHER INFORMATION: synthetic primer
```

<400> SEQUENCE: 5
agctttcaca taattaactt ttctttcca                                    29

<210> SEQ ID NO 6
<211> LENGTH: 27
<212> TYPE: DNA
<213> ORGANISM: Artificial Sequence
<220> FEATURE:
<223> OTHER INFORMATION: synthetic primer

<400> SEQUENCE: 6
ggtcttataa agcatcaaag aggacat                                      27

<210> SEQ ID NO 7
<211> LENGTH: 31
<212> TYPE: DNA
<213> ORGANISM: Artificial Sequence
<220> FEATURE:
<223> OTHER INFORMATION: synthetic primer

<400> SEQUENCE: 7
tgtattgagt tacactattg aaaatgtctg a                                 31

<210> SEQ ID NO 8
<211> LENGTH: 24
<212> TYPE: DNA
<213> ORGANISM: Artificial Sequence
<220> FEATURE:
<223> OTHER INFORMATION: synthetic primer

<400> SEQUENCE: 8
gctaaatggc aaaagttcat cctt                                         24

<210> SEQ ID NO 9
<211> LENGTH: 29
<212> TYPE: DNA
<213> ORGANISM: Artificial Sequence
<220> FEATURE:
<223> OTHER INFORMATION: synthetic primer

<400> SEQUENCE: 9
ggcatactgg ttttaggttt ttagatttt                                    29

<210> SEQ ID NO 10
<211> LENGTH: 32
<212> TYPE: DNA
<213> ORGANISM: Artificial Sequence
<220> FEATURE:
<223> OTHER INFORMATION: synthetic primer

<400> SEQUENCE: 10
cgataaatca atagttatat caacccataa aa                                32

<210> SEQ ID NO 11
<211> LENGTH: 28
<212> TYPE: DNA
<213> ORGANISM: Artificial Sequence
<220> FEATURE:
<223> OTHER INFORMATION: synthetic primer

<400> SEQUENCE: 11
gaccttcaat gtttattaca gctaaagc                                     28

```
<210> SEQ ID NO 12
<211> LENGTH: 28
<212> TYPE: DNA
<213> ORGANISM: Artificial Sequence
<220> FEATURE:
<223> OTHER INFORMATION: synthetic primer

<400> SEQUENCE: 12
aggaactgaa gcatattttt ggtatttc                                    28

<210> SEQ ID NO 13
<211> LENGTH: 22
<212> TYPE: DNA
<213> ORGANISM: Artificial Sequence
<220> FEATURE:
<223> OTHER INFORMATION: synthetic primer

<400> SEQUENCE: 13
ccatctttga atgtggcttt gg                                          22

<210> SEQ ID NO 14
<211> LENGTH: 22
<212> TYPE: DNA
<213> ORGANISM: Artificial Sequence
<220> FEATURE:
<223> OTHER INFORMATION: synthetic primer

<400> SEQUENCE: 14
gggcaatcct caccctataa gc                                          22

<210> SEQ ID NO 15
<211> LENGTH: 25
<212> TYPE: DNA
<213> ORGANISM: Artificial Sequence
<220> FEATURE:
<223> OTHER INFORMATION: synthetic primer

<400> SEQUENCE: 15
tcagttgagg gaaaaaaggt aagaa                                       25

<210> SEQ ID NO 16
<211> LENGTH: 27
<212> TYPE: DNA
<213> ORGANISM: Artificial Sequence
<220> FEATURE:
<223> OTHER INFORMATION: synthetic primer

<400> SEQUENCE: 16
ggcatgatta aacactaaga acattca                                     27

<210> SEQ ID NO 17
<211> LENGTH: 24
<212> TYPE: DNA
<213> ORGANISM: Artificial Sequence
<220> FEATURE:
<223> OTHER INFORMATION: synthetic primer

<400> SEQUENCE: 17
acttctttgc ttcaacgaat ccat                                        24

<210> SEQ ID NO 18
<211> LENGTH: 19
<212> TYPE: DNA
<213> ORGANISM: Artificial Sequence
<220> FEATURE:
<223> OTHER INFORMATION: synthetic primer
```

-continued

```
<400> SEQUENCE: 18
aagtcatggc aacggatgc                                              19

<210> SEQ ID NO 19
<211> LENGTH: 25
<212> TYPE: DNA
<213> ORGANISM: Artificial Sequence
<220> FEATURE:
<223> OTHER INFORMATION: synthetic primer

<400> SEQUENCE: 19
tgcaccctcg tacatacatg tattg                                       25

<210> SEQ ID NO 20
<211> LENGTH: 23
<212> TYPE: DNA
<213> ORGANISM: Artificial Sequence
<220> FEATURE:
<223> OTHER INFORMATION: synthetic primer

<400> SEQUENCE: 20
tcgtcaaaac ctcaaacaag gat                                         23

<210> SEQ ID NO 21
<211> LENGTH: 33
<212> TYPE: DNA
<213> ORGANISM: Artificial Sequence
<220> FEATURE:
<223> OTHER INFORMATION: synthetic primer

<400> SEQUENCE: 21
atgtattttt ttattccata gatgttatta gca                              33

<210> SEQ ID NO 22
<211> LENGTH: 25
<212> TYPE: DNA
<213> ORGANISM: Artificial Sequence
<220> FEATURE:
<223> OTHER INFORMATION: synthetic primer

<400> SEQUENCE: 22
gatgatgatg acaaaaattg tttgc                                       25

<210> SEQ ID NO 23
<211> LENGTH: 27
<212> TYPE: DNA
<213> ORGANISM: Artificial Sequence
<220> FEATURE:
<223> OTHER INFORMATION: synthetic primer

<400> SEQUENCE: 23
cactcactta agttatcctt ccttcgt                                     27

<210> SEQ ID NO 24
<211> LENGTH: 31
<212> TYPE: DNA
<213> ORGANISM: Artificial Sequence
<220> FEATURE:
<223> OTHER INFORMATION: synthetic primer

<400> SEQUENCE: 24
aattaataag agtacaatcc aggagatctt g                                31

<210> SEQ ID NO 25
<211> LENGTH: 21
<212> TYPE: DNA
```

```
<213> ORGANISM: Artificial Sequence
<220> FEATURE:
<223> OTHER INFORMATION: synthetic primer

<400> SEQUENCE: 25
caccagtgaa gcattggcaa t                                           21

<210> SEQ ID NO 26
<211> LENGTH: 28
<212> TYPE: DNA
<213> ORGANISM: Artificial Sequence
<220> FEATURE:
<223> OTHER INFORMATION: synthetic primer

<400> SEQUENCE: 26
tggcactacc tcacttttgt taaataaa                                    28

<210> SEQ ID NO 27
<211> LENGTH: 31
<212> TYPE: DNA
<213> ORGANISM: Artificial Sequence
<220> FEATURE:
<223> OTHER INFORMATION: synthetic primer

<400> SEQUENCE: 27
ttcagattta cacatgtaat agatttagcg t                                31

<210> SEQ ID NO 28
<211> LENGTH: 26
<212> TYPE: DNA
<213> ORGANISM: Artificial Sequence
<220> FEATURE:
<223> OTHER INFORMATION: synthetic primer

<400> SEQUENCE: 28
ggcaattgac aaacaatgaa tagaat                                      26

<210> SEQ ID NO 29
<211> LENGTH: 21
<212> TYPE: DNA
<213> ORGANISM: Artificial Sequence
<220> FEATURE:
<223> OTHER INFORMATION: synthetic primer

<400> SEQUENCE: 29
cccaagactt ttcccgaaca a                                           21

<210> SEQ ID NO 30
<211> LENGTH: 25
<212> TYPE: DNA
<213> ORGANISM: Artificial Sequence
<220> FEATURE:
<223> OTHER INFORMATION: synthetic primer

<400> SEQUENCE: 30
gataccattg gcaccattaa tacgt                                       25

<210> SEQ ID NO 31
<211> LENGTH: 22
<212> TYPE: DNA
<213> ORGANISM: Artificial Sequence
<220> FEATURE:
<223> OTHER INFORMATION: synthetic primer

<400> SEQUENCE: 31
actgccaaac taagccattt cc                                          22
```

<210> SEQ ID NO 32
<211> LENGTH: 26
<212> TYPE: DNA
<213> ORGANISM: Artificial Sequence
<220> FEATURE:
<223> OTHER INFORMATION: synthetic primer

<400> SEQUENCE: 32
atgtgcatat tcaagaaatg atgtca                                        26

<210> SEQ ID NO 33
<211> LENGTH: 26
<212> TYPE: DNA
<213> ORGANISM: Artificial Sequence
<220> FEATURE:
<223> OTHER INFORMATION: synthetic primer

<400> SEQUENCE: 33
gcattggtta cagtattttc ctgttg                                        26

<210> SEQ ID NO 34
<211> LENGTH: 24
<212> TYPE: DNA
<213> ORGANISM: Artificial Sequence
<220> FEATURE:
<223> OTHER INFORMATION: synthetic primer

<400> SEQUENCE: 34
accagtggga aagaaatgtc atct                                          24

<210> SEQ ID NO 35
<211> LENGTH: 24
<212> TYPE: DNA
<213> ORGANISM: Artificial Sequence
<220> FEATURE:
<223> OTHER INFORMATION: synthetic primer

<400> SEQUENCE: 35
acccctgcat gttctaaact tgtt                                          24

<210> SEQ ID NO 36
<211> LENGTH: 26
<212> TYPE: DNA
<213> ORGANISM: Artificial Sequence
<220> FEATURE:
<223> OTHER INFORMATION: synthetic primer

<400> SEQUENCE: 36
ctcacctttg taggcttgta ttctca                                        26

<210> SEQ ID NO 37
<211> LENGTH: 20
<212> TYPE: DNA
<213> ORGANISM: Artificial Sequence
<220> FEATURE:
<223> OTHER INFORMATION: synthetic primer

<400> SEQUENCE: 37
gccggaagga ctccaaaatt                                               20

<210> SEQ ID NO 38
<211> LENGTH: 28
<212> TYPE: DNA
<213> ORGANISM: Artificial Sequence
<220> FEATURE:
<223> OTHER INFORMATION: synthetic primer -continued

```
<400> SEQUENCE: 38
tctgtggtag aatcatgtcc tagatttt                                        28

<210> SEQ ID NO 39
<211> LENGTH: 26
<212> TYPE: DNA
<213> ORGANISM: Artificial Sequence
<220> FEATURE:
<223> OTHER INFORMATION: synthetic primer

<400> SEQUENCE: 39
cacctaagat cattcctagc attcct                                          26

<210> SEQ ID NO 40
<211> LENGTH: 30
<212> TYPE: DNA
<213> ORGANISM: Artificial Sequence
<220> FEATURE:
<223> OTHER INFORMATION: synthetic primer

<400> SEQUENCE: 40
gttaaacatt attttttca attgaccaat                                       30

<210> SEQ ID NO 41
<211> LENGTH: 27
<212> TYPE: DNA
<213> ORGANISM: Artificial Sequence
<220> FEATURE:
<223> OTHER INFORMATION: synthetic primer

<400> SEQUENCE: 41
cagtgaatga cacatcaaac aaaataa                                         27

<210> SEQ ID NO 42
<211> LENGTH: 20
<212> TYPE: DNA
<213> ORGANISM: Artificial Sequence
<220> FEATURE:
<223> OTHER INFORMATION: synthetic primer

<400> SEQUENCE: 42
gcatcccagc tgcttgtttc                                                 20

<210> SEQ ID NO 43
<211> LENGTH: 26
<212> TYPE: DNA
<213> ORGANISM: Artificial Sequence
<220> FEATURE:
<223> OTHER INFORMATION: synthetic primer

<400> SEQUENCE: 43
agcatgtcaa atgcacctaa gtacat                                          26

<210> SEQ ID NO 44
<211> LENGTH: 27
<212> TYPE: DNA
<213> ORGANISM: Artificial Sequence
<220> FEATURE:
<223> OTHER INFORMATION: synthetic primer

<400> SEQUENCE: 44
ggaaagccca agtattaagt atcaaca                                         27

<210> SEQ ID NO 45
<211> LENGTH: 25
<212> TYPE: DNA
```

```
<213> ORGANISM: Artificial Sequence
<220> FEATURE:
<223> OTHER INFORMATION: synthetic primer

<400> SEQUENCE: 45
ggtttcaacc atgaattatt tccat                                         25

<210> SEQ ID NO 46
<211> LENGTH: 22
<212> TYPE: DNA
<213> ORGANISM: Artificial Sequence
<220> FEATURE:
<223> OTHER INFORMATION: synthetic primer

<400> SEQUENCE: 46
ggatgacttt ggtgggttta gg                                            22

<210> SEQ ID NO 47
<211> LENGTH: 15
<212> TYPE: DNA
<213> ORGANISM: Artificial Sequence
<220> FEATURE:
<223> OTHER INFORMATION: synthetic primer

<400> SEQUENCE: 47
cgccggcgtg gttga                                                    15

<210> SEQ ID NO 48
<211> LENGTH: 19
<212> TYPE: DNA
<213> ORGANISM: Artificial Sequence
<220> FEATURE:
<223> OTHER INFORMATION: synthetic primer

<400> SEQUENCE: 48
gggcttccac cctgtgatc                                                19

<210> SEQ ID NO 49
<211> LENGTH: 25
<212> TYPE: DNA
<213> ORGANISM: Artificial Sequence
<220> FEATURE:
<223> OTHER INFORMATION: synthetic primer

<400> SEQUENCE: 49
ccaggaatat caattgattt aacgc                                         25

<210> SEQ ID NO 50
<211> LENGTH: 27
<212> TYPE: DNA
<213> ORGANISM: Artificial Sequence
<220> FEATURE:
<223> OTHER INFORMATION: synthetic primer

<400> SEQUENCE: 50
ttccgttgtc ttgtaatctg ttatctg                                       27

<210> SEQ ID NO 51
<211> LENGTH: 32
<212> TYPE: DNA
<213> ORGANISM: Artificial Sequence
<220> FEATURE:
<223> OTHER INFORMATION: synthetic primer

<400> SEQUENCE: 51 ctgttttttgg ctctatacta cagagattta tt                                32
```

```
<210> SEQ ID NO 52
<211> LENGTH: 24
<212> TYPE: DNA
<213> ORGANISM: Artificial Sequence
<220> FEATURE:
<223> OTHER INFORMATION: synthetic primer

<400> SEQUENCE: 52
atcttttggg ctgcaattat ttgt                                          24

<210> SEQ ID NO 53
<211> LENGTH: 25
<212> TYPE: DNA
<213> ORGANISM: Artificial Sequence
<220> FEATURE:
<223> OTHER INFORMATION: synthetic primer

<400> SEQUENCE: 53
gggatacaag aaaattgtgg catag                                         25

<210> SEQ ID NO 54
<211> LENGTH: 23
<212> TYPE: DNA
<213> ORGANISM: Artificial Sequence
<220> FEATURE:
<223> OTHER INFORMATION: synthetic primer

<400> SEQUENCE: 54
gctcaactca tcttctgctt cca                                           23

<210> SEQ ID NO 55
<211> LENGTH: 27
<212> TYPE: DNA
<213> ORGANISM: Artificial Sequence
<220> FEATURE:
<223> OTHER INFORMATION: synthetic primer

<400> SEQUENCE: 55
gatggaggtc atgagttaga atcttttt                                      27

<210> SEQ ID NO 56
<211> LENGTH: 27
<212> TYPE: DNA
<213> ORGANISM: Artificial Sequence
<220> FEATURE:
<223> OTHER INFORMATION: synthetic primer

<400> SEQUENCE: 56
ggtcacttag tcaatgacaa cacaatt                                       27

<210> SEQ ID NO 57
<211> LENGTH: 28
<212> TYPE: DNA
<213> ORGANISM: Artificial Sequence
<220> FEATURE:
<223> OTHER INFORMATION: synthetic primer

<400> SEQUENCE: 57
gatagattga gaggtttgaa tttgatga                                      28

<210> SEQ ID NO 58
<211> LENGTH: 27
<212> TYPE: DNA
<213> ORGANISM: Artificial Sequence
<220> FEATURE:
<223> OTHER INFORMATION: synthetic primer
```

<400> SEQUENCE: 58
gagtatctta acaccccgtt tattctg						27

<210> SEQ ID NO 59
<211> LENGTH: 30
<212> TYPE: DNA
<213> ORGANISM: Artificial Sequence
<220> FEATURE:
<223> OTHER INFORMATION: synthetic primer

<400> SEQUENCE: 59
taattgttat tctgaaatat aatgcagcaa						30

<210> SEQ ID NO 60
<211> LENGTH: 25
<212> TYPE: DNA
<213> ORGANISM: Artificial Sequence
<220> FEATURE:
<223> OTHER INFORMATION: synthetic primer

<400> SEQUENCE: 60
cccatcactt tattcaccaa atttt						25

<210> SEQ ID NO 61
<211> LENGTH: 25
<212> TYPE: DNA
<213> ORGANISM: Artificial Sequence
<220> FEATURE:
<223> OTHER INFORMATION: synthetic primer

<400> SEQUENCE: 61
cctttcaaaa cctttaaggc atgta						25

<210> SEQ ID NO 62
<211> LENGTH: 25
<212> TYPE: DNA
<213> ORGANISM: Artificial Sequence
<220> FEATURE:
<223> OTHER INFORMATION: synthetic primer

<400> SEQUENCE: 62
gttcctagcc aacaatgagt ttctc						25

<210> SEQ ID NO 63
<211> LENGTH: 22
<212> TYPE: DNA
<213> ORGANISM: Artificial Sequence
<220> FEATURE:
<223> OTHER INFORMATION: synthetic primer

<400> SEQUENCE: 63
aaagcgtatc taaggcccat ca						22

<210> SEQ ID NO 64
<211> LENGTH: 23
<212> TYPE: DNA
<213> ORGANISM: Artificial Sequence
<220> FEATURE:
<223> OTHER INFORMATION: synthetic primer

<400> SEQUENCE: 64
tttgcacccg atgatctaaa cat						23

<210> SEQ ID NO 65
<211> LENGTH: 26
<212> TYPE: DNA

```
<213> ORGANISM: Artificial Sequence
<220> FEATURE:
<223> OTHER INFORMATION: synthetic primer

<400> SEQUENCE: 65
accatgaggt aatttcactt tcagaa                                          26

<210> SEQ ID NO 66
<211> LENGTH: 22
<212> TYPE: DNA
<213> ORGANISM: Artificial Sequence
<220> FEATURE:
<223> OTHER INFORMATION: synthetic primer

<400> SEQUENCE: 66
acgcaccata tgctgaaatg ag                                              22

<210> SEQ ID NO 67
<211> LENGTH: 21
<212> TYPE: DNA
<213> ORGANISM: Artificial Sequence
<220> FEATURE:
<223> OTHER INFORMATION: synthetic primer

<400> SEQUENCE: 67
gcattgaggg gaagtgtcgt a                                               21

<210> SEQ ID NO 68
<211> LENGTH: 25
<212> TYPE: DNA
<213> ORGANISM: Artificial Sequence
<220> FEATURE:
<223> OTHER INFORMATION: synthetic primer

<400> SEQUENCE: 68
ttccttctgc aatttattct ccaaa                                           25

<210> SEQ ID NO 69
<211> LENGTH: 24
<212> TYPE: DNA
<213> ORGANISM: Artificial Sequence
<220> FEATURE:
<223> OTHER INFORMATION: synthetic primer

<400> SEQUENCE: 69
aagagttctc gtttctcact tccg                                            24

<210> SEQ ID NO 70
<211> LENGTH: 25
<212> TYPE: DNA
<213> ORGANISM: Artificial Sequence
<220> FEATURE:
<223> OTHER INFORMATION: synthetic primer

<400> SEQUENCE: 70
ggtgatggtg gaaatgaaat gtatt                                           25

<210> SEQ ID NO 71
<211> LENGTH: 30
<212> TYPE: DNA
<213> ORGANISM: Artificial Sequence
<220> FEATURE:
<223> OTHER INFORMATION: synthetic primer

<400> SEQUENCE: 71
ctttcatatc tgaaaattca atttcaaagt                                      30
```

```
<210> SEQ ID NO 72
<211> LENGTH: 20
<212> TYPE: DNA
<213> ORGANISM: Artificial Sequence
<220> FEATURE:
<223> OTHER INFORMATION: synthetic primer

<400> SEQUENCE: 72
gcatgtggac ggttggaaac                                              20

<210> SEQ ID NO 73
<211> LENGTH: 23
<212> TYPE: DNA
<213> ORGANISM: Artificial Sequence
<220> FEATURE:
<223> OTHER INFORMATION: synthetic primer

<400> SEQUENCE: 73
attcagttcg atggccaata aaa                                          23

<210> SEQ ID NO 74
<211> LENGTH: 30
<212> TYPE: DNA
<213> ORGANISM: Artificial Sequence
<220> FEATURE:
<223> OTHER INFORMATION: synthetic primer

<400> SEQUENCE: 74
ttttgtttga ttctatgtta actttgcttt                                   30

<210> SEQ ID NO 75
<211> LENGTH: 30
<212> TYPE: DNA
<213> ORGANISM: Artificial Sequence
<220> FEATURE:
<223> OTHER INFORMATION: synthetic primer

<400> SEQUENCE: 75
ttaaacttgt tacggtacgt actgtacaaa                                   30

<210> SEQ ID NO 76
<211> LENGTH: 25
<212> TYPE: DNA
<213> ORGANISM: Artificial Sequence
<220> FEATURE:
<223> OTHER INFORMATION: synthetic primer

<400> SEQUENCE: 76
gaagcatgtg catgtgtagt gtaga                                        25

<210> SEQ ID NO 77
<211> LENGTH: 20
<212> TYPE: DNA
<213> ORGANISM: Artificial Sequence
<220> FEATURE:
<223> OTHER INFORMATION: synthetic primer

<400> SEQUENCE: 77
tggagcgtta tggggagcta                                              20

<210> SEQ ID NO 78
<211> LENGTH: 24
<212> TYPE: DNA
<213> ORGANISM: Artificial Sequence
<220> FEATURE:
<223> OTHER INFORMATION: synthetic primer
```

```
<400> SEQUENCE: 78
ggagtggtat cactgaagca tcct                                               24

<210> SEQ ID NO 79
<211> LENGTH: 28
<212> TYPE: DNA
<213> ORGANISM: Artificial Sequence
<220> FEATURE:
<223> OTHER INFORMATION: synthetic primer

<400> SEQUENCE: 79
tctaacataa cgagaatcca aacatgat                                           28

<210> SEQ ID NO 80
<211> LENGTH: 25
<212> TYPE: DNA
<213> ORGANISM: Artificial Sequence
<220> FEATURE:
<223> OTHER INFORMATION: synthetic primer

<400> SEQUENCE: 80
ccatgaagct aatccaaaca cacta                                              25

<210> SEQ ID NO 81
<211> LENGTH: 890
<212> TYPE: DNA
<213> ORGANISM: Glycine max

<400> SEQUENCE: 81 attttacccct gaggttttgc catatggtga aactttcttc catgagccag ttggtagagc       60
ttctgatggt cgccttatca tagatttcat tggtatatac cttttcaata attctcatca      120
tttttttgct ttatttctta ttcatttatt tgtgaaacac gatcaaatga catgtttgct      180
ttttctatct actttgtttt cttttttcttt aatcatcatg tggtgtctca caacacaagc    240
taaatcttct tttctttgag ttttgttcca caaagattgg attccagttt gtgttgttat      300
tggagttata agatacatgt ggttgaaggg agaagaggga agggtgatgg aggtcatgag      360
ttagaatctt ttttattaac aaaaattaac aaattaacaa ctaatatata ttgactgata      420
aaaagaattg tgttgtcatt gactaagtga ccaacacaaa catctctacc caaatgaata      480
aagttgggat tcaataagaa tgagttgtga aattttttta cacaatatct ctgtctacca      540
ttatctattt agcagccata gaatcctatg atggtcatac ttacaaagtg gtacataaaa      600
aatataaagt tttcacgaag tgaaaattta atatgagaag atcataatat atatattaag      660
ggatctagtt caattagttg aagtgtatat aagtattgta aatttcctct tatcgtgttc      720
aatttctgca tatcaaaaaa tatatcataa tatatatagt tctattgcca agaaactatc      780
atactagtga tttggtgcca tttgtgtttg cagcccagca tctaggtttc ccattcttga      840
gtgcatacat aaattcaatt gggacaagtt ataggcacgg tgcaaacttt                 890

<210> SEQ ID NO 82
<211> LENGTH: 1252
<212> TYPE: DNA
<213> ORGANISM: Glycine max

<400> SEQUENCE: 82
ggccagcttg catgcctgca ggagaagtat cgcaaaactt aagagtgaag gaaaaagcag       60
tgttgttcag tttttcacct tctcttattt taagcctagc tttcacataa ttaacttttc      120
tttccaaaac tcaagtttat gatttgaaaa actatgtcct ctttgatgct ttataagacc      180
```

| | |
|---|---|
| atatagattt tcttgcctag aacagtggtc aataatttgg aactatagtg actttgctgc | 240 |
| tgtataaatt tatatttaat atagaattat caatttctt attgcatctc aaatctcaat | 300 |
| gcctacctat tcctcctcat gcaggacatg aagcggcaat gtgatgaaaa aaggtttgta | 360 |
| tttacacaac tgctattgtt ttttctcatc attatgtgat gtttcctgaa tctgttttat | 420 |
| tgccttcaga gatgtttatg aatacatgat tgcccaacag aaagagaaag gaaagtcaaa | 480 |
| aagtgctaaa ggtgaaagtt tcacgctaca gcagttgcaa gcagctcatg ctgaatatga | 540 |
| agacgaagca aaactttgtg cctttcggtt aaaatcgctg aagcaaggcc agtcacgcag | 600 |
| tctcctaaca caagcagcgc gtcaccatgc tgctcaggtt ttcttgaact atgacctttc | 660 |
| tcattcaaat ctttttatcat ttcttcagcc tagtcttgat gcatctttgt tcttgttctt | 720 |
| ctttcaatat agttgaattt cttccggaaa ggacttaaat cactagaggc tgttgaccca | 780 |
| catgttagga tgattgctga acgacaacat attgattacc aattcagtgg cctggaggat | 840 |
| gatggaggtg aaaatgataa taatgatgat gggaatgatt ttgacgtcat tgaaggtggt | 900 |
| gagttgagtt ttgactacag ggcaaataag caagggccat atattgtttc cacatcaccg | 960 |
| aactcagcag aggtaggaaa tttgtattac tcaaaacttg aatggttttc aaagcctggg | 1020 |
| tgcatattga actttattct tattgctcat ttgctttttt atttaaaata ttaccaaact | 1080 |
| ttgtcacagt tgtcatttta tacttgttgc agtctatagc tcgctacaaa ttaaaaacat | 1140 |
| tccattgttg ttttcataat ctgaactata aattcatctt atcataatca ttggcaatgt | 1200 |
| tttgccaggt ggaagaatca ggccgttcat atattcgagc ttcaaccccca ga | 1252 |

<210> SEQ ID NO 83
<211> LENGTH: 614
<212> TYPE: DNA
<213> ORGANISM: Glycine max

<400> SEQUENCE: 83

| | |
|---|---|
| atggatgtta tcaataagtg cttctctaaa aaggctgttg aggaaatatt atcttctctc | 60 |
| gtaagttgta ttgagttaca ctattgaaaa tgtctgatta atattcttca gcatgatcaa | 120 |
| ggatgaactt tgccatttta gcaacctgaa ttttagcctg ctgttttagg aggtggaagc | 180 |
| tacgagaaag gctgatcctt ggatttctgc aactattcaa tccttaaaga aagcatctcc | 240 |
| aacaagcctt aaaatctttc ttagatcggt atgtgtccag aatgtattaa aagttctgtt | 300 |
| ttatgtacat tctaaaattc acttctcttc tgtgttcaac tgttgaagta tcatttttat | 360 |
| catcatcatc attttactat cattattgtg attataacaa ctgttttttt tttaaattta | 420 |
| ttttggcctt tttcagatta gacaaggaag gctccaaggt gttggacaat gccttgtttc | 480 |
| tgattataga gttgtttgtc atattctaaa aggacactac agcaaggatt tcttcgaggt | 540 |
| tatctgatga ttcctataca tagttatgct tttaattatt tttctttcat gccctatggt | 600 |
| taatgttacc cttt | 614 |

<210> SEQ ID NO 84
<211> LENGTH: 597
<212> TYPE: DNA
<213> ORGANISM: Glycine max

<400> SEQUENCE: 84

| | |
|---|---|
| gttttttcctc actctctcca tcatgttcat gtcaccactc tccaagtagt tactcccttg | 60 |
| caagtcatgc taacttggag agctgattgc atgcttctct gtaacataat cctagtgtac | 120 |
| accttaatag gatgggtttc aattattcag ttgttgaaaa gtcattacta ctcagctagg | 180 |

| | |
|---|---|
| aaaggcaggc atggaatggc cattttctaa ataatttgtt ataacaattg aagagagtga | 240 |
| taacagggta agaagtgagt gaaagctaca gcctacacaa aagagagaac ttactttgaa | 300 |
| aggaatttat aaaattgaat caccaaatcc aggtcattct catataccgt actgagtttt | 360 |
| cccaggcatg agatgccaaa tcttgggtct gttgtataaa ttatattaat aacaatgttt | 420 |
| cagaataaaa tactatgaag tttggttata caaatacaat agaacagatt ctgcatgcaa | 480 |
| ccattccatg tatcaaaatg ctcaagttaa ccccacagct atcctagact atataatggg | 540 |
| aggaaaagaa atgtaaagta aataaaagt taagaaaggt cattcctttc aaatgta | 597 |

<210> SEQ ID NO 85
<211> LENGTH: 1209
<212> TYPE: DNA
<213> ORGANISM: Glycine max

<400> SEQUENCE: 85

| | |
|---|---|
| tggcaatcca cacatacgac tgtttgatgt taactcaaat agtcctcaac cagtttgtct | 60 |
| ttctcacctg atacacttgc tgcaaaataa atcatttatt ttctggttcc caacaatttt | 120 |
| tgttcctgat tttgtggcag gtaatgagct atgattcaca taccaataat gtaatggctg | 180 |
| ttgggtttca atgtgatggt aattggatgt attctggctc agaggatggc acagttaaaa | 240 |
| tctgggattt gaggtgaagt agatatacag catgtagtgt aataagtttg tagtatgact | 300 |
| tatgccctta agttcattct tgataatcat tgcttatatg tgataacaaa aatgcagggc | 360 |
| acccggttgt caaagggaat atgaaagtcg tgcagctgta acactgttg ttctacaccc | 420 |
| aaatcaggtt atgtttcacc atttttggtg gatatacaat ttattcctgg cttatgagta | 480 |
| cattaatcat taacatggta caacaagtta gaagatgtaa caattaataa caataattaa | 540 |
| tgcaagaatc agattagtag cttggactga attggcctta cggcatactg gttttaggtt | 600 |
| tttagatttt atttactc atttaactgc ttaccacttt tatggggtga tataactatt | 660 |
| gatttatcga ttgatgttta tttagatctg gattatgaca tactttcaat tataagtgct | 720 |
| tatttgtttc atagcatttc agttgaagaa tgggtcattg gtgctctttc ttcattgatt | 780 |
| atggttcctt aattttgca atatccagaa tactcagatt gcagttctta tagtttcttg | 840 |
| ctttgtggtt ctcattgatt ttttttctgg tgatcctaca gactgaacta atatctggtg | 900 |
| accaaaatgg caacattcgt gtgtgggatt tgacagcaaa tcatgcagt tgcgaattgg | 960 |
| tattagttat gaccttttt tattgaatat ggatatcact gtaggatcaa gattcaaaat | 1020 |
| attttctatc caagaaaaaa atccaaaata atatttatta agaatgaact gtctaaatta | 1080 |
| taagtcttgt agttctaact ctataggcat acaccttgca aaagcacatg atgcttctct | 1140 |
| ttgacctccc acatgtactc taatatagta atatgcattc aattgtcatg cttcaccaaa | 1200 |
| gggttcttt | 1209 |

<210> SEQ ID NO 86
<211> LENGTH: 750
<212> TYPE: DNA
<213> ORGANISM: Glycine max

<400> SEQUENCE: 86

| | |
|---|---|
| aaactatcta tctacgtgct ttgtatggat aggttacttg cctccattca tccatttctt | 60 |
| aaaccatttg aaaagtatct ctttagcata actagttttt cctaagagaa ggccacataa | 120 |
| ttacatatta atcaataggg gtaggggtga tgtcaaaatt aggactcagt ctcatttata | 180 |
| gcttgatttt caatagttca taacagaact taaaaatata aaggaccttc aatgtttatt | 240 |

```
acagctaaag ccactaaatg gtaggcatca ataacagtat atatccaatc actgatataa    300
attaatgaaa taccaaaaat atgcttcagt tccttctgag cttctcggat aatataagct    360
aaagaaattc atattgaaga aaacaaaaat tacttcataa attttgttga agagaaggcc    420
agtgcaaaaa acatattttc ctaaaaaaga ttatgaacga gtatagatac cacctgatag    480
accatcttcc agtcccattc ggtatatgac gagaagctga gatgcagaag ctcataatgt    540
ccaatgtcag gagcatcttt ggttgacttt ttcttagaga acaatttatc cataaaaagt    600
gtgttcagat gggcaaaagt aaaaacagat gaagcactaa aagccattta tgctttaaca    660
ttgcttggat ttatttattt ttaatatttt tatgaaagaa cttgcactag ctgtcacaat    720
gttctttgga tgagattcta aagaactaaa                                     750

<210> SEQ ID NO 87
<211> LENGTH: 578
<212> TYPE: DNA
<213> ORGANISM: Glycine max

<400> SEQUENCE: 87
aaagggcaaa acatattgtt gatctgcatg ttccttttac gcagattctc ttttgtgggc     60
aatctgcccc tgcataatct ccaagcgaat accgcaattt tgctaggtat ctttgtcttc    120
catagttcca tactccaatg tggcctgttt aatggatcta agattttga taccatcttt     180 gaatgtggct ttgggcttaa ctcaatcaaa agctagctta tagggtgagg attgccccc     240 atttatatgc cttatcttga ccttgagatg atgtgagact tgggttttc cttttttat     300 tttattgtgt tgatgcgctt cttgaatatt tcacattaca aagattagg aaactgatgg     360 tggcagtgca acaaaagatt agggaaccaa cccaattgtg acagtttgt caaacaaatg    420 ccaagaaaat ttgggccaaa acaagatcat tcccaaatca ataatgaagc aaatcaccaa    480
acacttggtg cacaaagata tgcaatctga tgtgatgagg cactaaccag ccgtcaggat    540
tgagaaccga tgaagaacat gaacatgtcc ccgagaac                            578

<210> SEQ ID NO 88
<211> LENGTH: 758
<212> TYPE: DNA
<213> ORGANISM: Glycine max

<400> SEQUENCE: 88
atgtacttag gtatgttagt tgtttgctga attagtttga accaatgttt gttgtttgag     60
taaattgtta tctcctcctt tgtatttgt gttactatgc ctacctccca tctattatgc    120
aaacctacaa aaagaactta ctgtatttgc aaaacaaaac tttacaacta actccaaaat    180
gctggcaaga ctagtagatt tgtcagatca aggaagtttg ttttatagtc aaatattatt    240
cctacactgt tcaacctttc agttgaggga aaaaggtaa gaatacattc atctggcagt    300
gcagcagatt tgaatgttct tagtgtttaa tcatgcctct tgtccctttt tcttgttata    360
taagtctcgg aaagggtagg atttaatcat gagacattca tgataatgta ttagttaaac    420
aatctgttag acataaatagt ttattggatt tagtttcagc attgctgtaa attcaatgga    480
ggtatttgcc tgctttcata taaatggat gtctgtgtta ggaacccaat gaataactct     540
gttgattgaa tgaaattgaa cagaaacaaa gagaaagaat tctcctccaa gggttttccc    600
tttcttacga acttgctaat tgtctgcatc tccttcttcc ccctatttgt gtaattgatg    660
ccctttaatg aactaactgc tgtatttgtt gctaacaaat ttcccctccc attctgttcc    720
aactcctatc aatctatgca gctgatgctt ttgcactt                            758
```

<210> SEQ ID NO 89
<211> LENGTH: 776
<212> TYPE: DNA
<213> ORGANISM: Glycine max

<400> SEQUENCE: 89

| | | | | | | |
|---|---|---|---|---|---|---|
| atgatggagt | attcaattct | atccaaagag | gttgatatct | taagtgacga | aagtctcttc | 60 |
| gttattggca | ttctttcctt | aattttgtat | ctttccacca | ataaagcact | tgaagagact | 120 |
| tccaaggcca | ttcttttaa | tacttgtata | atctctatgg | tcagcacacc | gtagtctgtg | 180 |
| ctgcttcttc | gaagggacct | gctttggttg | accatgacga | gggaacatgc | acaggagaaa | 240 |
| ctttaatatt | tgttcttttg | attcattact | tcgccgttaa | aaggtaagcc | ggttcgaatc | 300 |
| agtaataaga | aaccttttat | attctagctt | gcatgctatc | ctaccagggt | tcgtggattg | 360 |
| gcaaaacttc | tttgcttcaa | cgaatccatc | ggagccgcta | gctttcattg | gcatccgttg | 420 |
| ccatgacttg | tgcagacttc | tgcattttgg | ttctcctgta | atcaagattg | ctgcttctta | 480 |
| tagcctgtta | gagttattta | acagaatatc | agatcaaata | aacagtgatc | atgaagagtt | 540 |
| gagatgtact | attgggtact | taatgcccat | aaggattgga | aggaatggtt | ttctataatg | 600 |
| atctgagagt | ggctaaaaat | tgttccctct | gtctgtcaat | gattctggga | tgggaaaagc | 660 |
| tgacaaagga | aacaaaagtc | ttagaagaga | gtagctggtg | tagattgatt | atagaggaga | 720 |
| tgacagtatc | tttggccgct | cctgctttag | catcacaatc | attcacgaac | aatcaa | 776 |

<210> SEQ ID NO 90
<211> LENGTH: 597
<212> TYPE: DNA
<213> ORGANISM: Glycine max

<400> SEQUENCE: 90

| | | | | | | |
|---|---|---|---|---|---|---|
| tgacttcctt | agcacatgtt | caaagttcaa | actaccttaa | ctgtttcctt | tcttgttctc | 60 |
| tttgataggt | gtcacaccaa | tatcttctca | tatgcatccc | atattttatc | ctttcttata | 120 |
| tgtccacatc | ttcatcttaa | tgttttcttt | tttactccta | caactttttt | ttttgtgttg | 180 |
| tccttttaaa | gcccaatatt | cttgctacca | taaagtataa | ctagttatat | aaccatgcca | 240 |
| tgaaacttga | ttttagtaag | tagtttacag | tcagaaataa | tccttgatgt | tttccctcgt | 300 |
| atttaaccac | ccagcttgga | ttccacgtgt | ggcattgtga | tggtgtaaac | ctatccttgt | 360 |
| aagaaagtct | tgagtttcac | ttccaagagt | tgcaccctcg | tacatacatg | tattgtatag | 420 |
| cttattaatg | tcgcaatatg | tcgtgagtga | tccttgtttg | aggttttgac | gagttttcgt | 480 |
| tttcgttggc | tatcaaggat | ctaatacaat | tttcctccat | tatcagaatt | taggatttgt | 540 |
| tactagacta | taggcagagt | tatctttgtt | gattttgata | ttctattaaa | ataatat | 597 |

<210> SEQ ID NO 91
<211> LENGTH: 1036
<212> TYPE: DNA
<213> ORGANISM: Glycine max

<400> SEQUENCE: 91

| | | | | | | |
|---|---|---|---|---|---|---|
| tctagagtcg | acctgcagga | aaatactca | ggagtatata | atgctaacag | gttttcccga | 60 |
| aggactccta | caggcacagc | ttgttagtgt | aagtccacac | tcactgtaga | cttggctgtt | 120 |
| ctctccccta | tctatttatt | gaaacttagg | atgataggat | ccacttttgc | tgaaggaaag | 180 |
| gtccatgtgt | atacttaaag | tcacagaatg | tcatttggtg | tttgaatata | aattttcagt | 240 |
| gagttcgatg | gcagctatgg | aaagtaatca | aaataaccag | gtagatgtca | aatgcaagaa | 300 |

```
atggtagtcc aaattacaga tttcagcagt ttgtacccta aaacgatagc atctggtata      360
taaccaatca gttaatctga tttactatca taaatgaata aaaaaaataa gtaaagagga      420
gtacaacaca cttttaaaa catccttta acatactctc tactattaat taaaaataaa       480
atttattaga aattgcaaaa tcacgaatga ggctcattat ataaggtgag acctgcccaa      540
ttttgtattt tctgataaat tccagccaat agagtactta aaaatgtgcg acaaagagtg     600
tgttgttagc atttctcaat aactaaacct gaagacttca attgcattct gactcatgct     660
tctaataaat gagactaaat aatacttcca tgtatttttt tattccatag atgttattag     720
cataacactc actccattct tgtcttatga attaggcaaa caattttgt catcatcatc      780
atcatcaaga atgagtttaa ctccattatt cttaagagca ttcacaacag cccaaaccct      840
ggtttggttc ttaaatcctt tcttcccaac ttctttagtt atgtttgcat gaatccctct     900
tccttctcct tcattaagcc cctcaacttt cagccgcctg gccaatacct ctccaacaac     960
agctgctgct tttgcattgc aggatctgcc acactcaagt gactctttaa tggtgtgttc    1020
tgcaggtcga ctctag                                                     1036

<210> SEQ ID NO 92
<211> LENGTH: 1008
<212> TYPE: DNA
<213> ORGANISM: Glycine max

<400> SEQUENCE: 92
tgacactgct ttgtacttat tttcttcctt ctttctttgg tctatgaaag atattataat       60
tttaccttga tctcgatctt tccaattcaa ttgtactttc aatcaaatcg cgttttctat      120
gaaattaatt ctcaatattg tgatattata tatgctgagg tatgtgtgag attttttta      180
tatttttttt tttgtaattt cagaaattct tgttagctca agaagtaccc agcagcaatt     240
cctagttatt ttgcaggaag taaccactc acttaagtta tccttccttc gtcctctaac     300
aatgaaagta atattttgg ggtatgcaca aagtctttca aaaacaaaca agatctcctg      360
gattgtactc ttattaatta atggagttct gtacatatac atggcatcac acttccaata    420
tagtccaaca aaatggcctt actcctcaat tgccctcttg taattaagat gaaagcacca    480
attgagaggt ggaagcatgg caaacttttt taggtatatg ttcttttga gaagaaattt     540
atgcatgaat atatgtcttt tattttttt tttcctattt tcagactgcg aacaacatca     600
gtatatatga tggttttctc catacgatgt ttccagaagc tagagataca aatgaaaaaa     660
aggttcagga ctgcatatga agggataatt tgaaaagaag aataaaagag gaaaagatat     720
ttaagtaatt ttttttttct tgaagaaaaa gaaagaaagg aagatatata tatctttaga    780
taaatataat taaggacgt gtaaatatta ttaattgtca aaaaagtaaa gtagcagaga     840
actacatata gtattacatg caacaacaag cggagacaac taagggactc gcttaagtac    900
tagagtcctc atcgccctct ctttatttc attaatataa attttacaac attatgatat    960
atagtatcct gcgactgaaa aactgccctg caggcatgca agctggcg                1008

<210> SEQ ID NO 93
<211> LENGTH: 660
<212> TYPE: DNA
<213> ORGANISM: Glycine max

<400> SEQUENCE: 93
agtatggaat tttccatgac ctaatgtcca tcttgaaacg agttgagctc atattattat       60
gcaattggtt gcaaggaaaa ttaacatgat caaatgcatt tgtaactaaa ttgcaagcaa      120
```

-continued

| | |
|---|---|
| catgcttttt taacatactt tctctgttgg aggatacttc tcatgttgat cttatttaat | 180 |
| aacctgggtc cattctttat tagtgggacc aatattaaat aaattcatca ataaaaaaag | 240 |
| gcagtatttc tagtatcatt ttcgtgactt taaggtggcc agtgaagcat ccaccgaccc | 300 |
| ccataatacc tgaactgaat gcagtaagca atgcactgtt tttcaccagt gaagcattgg | 360 |
| caatgttggt atttaattgt gcttgtgtta ttagtggtca atttatttaa caaaagtgag | 420 |
| gtagtgccag tagtttggtt ataaaatgcg gcaaatgtat taggaaaaca gggatcaatt | 480 |
| cattatgtgt gaagtagtga agcacaaaac ttgtttcaat aaaattgtta acctggttga | 540 |
| aatcatcaca agagatctgt gtattggcta taaaagctat gatacaatta aagggtaaca | 600 |
| taacataatg tagcaatggt taactaaact ccttcagtgt gttttaaat ctttccaccc | 660 |

<210> SEQ ID NO 94
<211> LENGTH: 1159
<212> TYPE: DNA
<213> ORGANISM: Glycine max

<400> SEQUENCE: 94

| | |
|---|---|
| atatacttca agtggtttca ctttgtggga agagtcgtcg gggaagaggg gaaagacagg | 60 |
| aaaggagaat aatgcgggcg agaaaccctc tctaggaggt aaaccataaa ttttctcttt | 120 |
| attgtgtaca ttgcatcagt agtattttgt aaaaattcgc cgaaatatttt ttcaatttat | 180 |
| aaaaataata aatgaaattt ataatttat ttatatatat tcatataaaa attttgattt | 240 |
| tttcaaacaa acacttttca tcttaattca atgaatttca tagatgaatt tataacaaat | 300 |
| ttttgtatga taataattta ttgaataaat acttaactaa atatgcctta aatattagag | 360 |
| aaaagaggtt atgatataaa attattttat attttttattt aattacaaat tattatttat | 420 |
| gataaattta ttaattttta taaaaaaata atcttaaaaa ttatacaaat aataatttgt | 480 |
| gattaaacaa taatatttta taccaatgta tcgccacttt gttccaccaa tttcctacat | 540 |
| tgtcatggag ttttctgtaa cttttgttta tacgtgcatg aatctaaact taaatcaaaa | 600 |
| caaggatcaa acaaccactt ttccttcctt atttctcaat attgaagtct attggcaatt | 660 |
| tatatatgca aatcatctca attgttcat agaaatttga tctcttccta aaaacaagta | 720 |
| gatggagaaa gtcatctatt tacaatagga aattatatct gtataatttt aaaaaatata | 780 |
| tttaataaga agaaaagaaa aaagatgata cctacaaata tatttgtaca aacatttgtt | 840 |
| tatataaaat tattaatgtg ataaaaaata aaaagtaaaa atagaaaatc ttgtattaca | 900 |
| tctataaata aatatatatg tcttgccaca atatatgtgt tgattccttt cagatttaca | 960 |
| catgtaatag atttagcgtg gcagtgcgct ggactagtta gccaaattct attcattgtt | 1020 |
| tgtcaattgc cagtattcag caataaaaaa cagtagaagt aataataata gtaattacaa | 1080 |
| tattaatgtt gtcaaatatc aactgcataa tgtgtctaac ggtaacagcg tttggccgcg | 1140 |
| cttgatactg tgacagagt | 1159 |

<210> SEQ ID NO 95
<211> LENGTH: 973
<212> TYPE: DNA
<213> ORGANISM: Glycine max

<400> SEQUENCE: 95

| | |
|---|---|
| acaataagca agctaattag tagttaccca agacttttcc cgaacaactg gtttgctcaa | 60 |
| gaatatttgt agcacgtatt aatggtgcca atggtatcaa ttcttaaatg aaatgttggt | 120 |
| cataccttcc aacgtatagg ttttcatcca aaaaatatgg aagcaaaaat agccactatc | 180 |

| | |
|---|---|
| acaagcgcga gagggttgaa aacacatgca tacaatggac ctttaatccg tacacaccat | 240 |
| gcagtaacaa taaccactaa tccagagtac acaattccct gccacaacat cttggtttct | 300 |
| tagtaattac taattttttag tatactagtt caccatccaa ttaatgcaaa ttttaactta | 360 |
| cagaaaatcc gcagttagaa gcctaatatc ccacccaac ttccattggc tccaatcctt | 420 |
| cacaacacat agggctaaga ctgtggcttg tattgccccc attaaggtca tcagcgctgt | 480 |
| acttgagtaa tggcttggat attcgatctt tactcatctt agtctgtccc atttagtgat | 540 |
| tattcatcaa caacaacaac tacacttttt ttttttttgc caacaaatag aattataatt | 600 |
| agataaggcc ataagggtaa acccttaaca catcatatat ttcatcaaca tttttttta | 660 |
| tcgctttctt ctaatcatgt tatttatctt attgcatgtt atacttatat tttttttttt | 720 |
| ctctctttct caattagcaa ctgagtgccc atgaaaatata tatttctctt taagtactga | 780 |
| gatataacaa caggaagctt aattacctga atgatgagcc ataatgaaag actaaaaaca | 840 |
| cttccaagac aacataaaac acctagccat tttcttccag aaacagcatg cgatgatcca | 900 |
| aggtggccat tttgattttt gtgaaaaaat atttatgtgc aaagtcaaaa tgtcaatttc | 960 |
| taaccctta aaa | 973 |

<210> SEQ ID NO 96
<211> LENGTH: 1395
<212> TYPE: DNA
<213> ORGANISM: Glycine max

<400> SEQUENCE: 96

| | |
|---|---|
| tcttgcatgc ctgcagaatt aatatcgtgt gtatgtatat acatgcaaga ctagctaatt | 60 |
| tttttttttt tttatattga aaggagcaag acaaaagcta gttgatggtg caattaatat | 120 |
| ttcaggtaat ttatactaca ataaaacttc agaatctcac tgaaaaggta gggcacacta | 180 |
| cagggtcatt aattttgatg acaagctaat taaacaacaa aaattcattt gattacactg | 240 |
| tagaaaaaag gcactgttcc attaatacaa gagaaaattg aggcatcgat ctcatatta | 300 |
| tacatttaac tagcaaacaa tcagataaat tttacctacg ctagatttaa attggatgca | 360 |
| gttttgtaga tgttttagt attgtttttt aattagaatt ggatcgagtt tcgactcggt | 420 |
| aatctgctta atgaagattt ttattaaagg ttaatgtaaa ttagtaagat aaaactctaa | 480 |
| ttataggtag aggataatac caacaacact tgtaatcgtt ttaaattcat ttggcgctag | 540 |
| cacactcttt ttgcatggtt aaactttttg tttgtagtaa tcccaattca actgtagtat | 600 |
| atcataagac ataacccccc aaattaagtg ccaaacaccc ctccattcat cggctatcct | 660 |
| actacttaaa aaaaaaaggt ttttctgtta ttcccatgtc tcgattgtat cgaagatctt | 720 |
| caaacgctga accaacaggt caaatgcaaa ataacttaat gaaaaaacaa tggatatttc | 780 |
| aaaccggatt caaaccttaa ttatatgtat aggtactta ggaaattcaa cgaacttacc | 840 |
| ttatgcttaa acggcacttg ccctacctaa tcctgatttt cgttataact tatctgacaa | 900 |
| taaagttctc cgtgtggcgg aaaattgcca aagggtaatc tctaggtaac ttcttcaca | 960 |
| ctgccaaact aagccatttc cctggtatat acatgtttcc catttggttt tcaattcaa | 1020 |
| aaaaaaataa ttaaacctaa ttgaaaaaaa caataataat gatgacatca tttcttgaat | 1080 |
| atgcacatcc cctctgcacc tataaaacca aatatcacga gcaattaacc tatgctatac | 1140 |
| ggtcctagtt aacttagctt ttccccaaga gcatacactt gctaataact gctaactatt | 1200 |
| ctttgcctta gaaatatat tcgctgtgcc actgcattat gggaaggtca ccatgctgtg | 1260 |
| aagagaatgt tggtgtaaag aaagggccat ggacgccaga agaagatgag aagctgattg | 1320 |

```
attatatcag caaacacggc catggcagtt ggagaacact tccaaagcgt gcaggtctca    1380
ataggtgtgg taaga                                                     1395

<210> SEQ ID NO 97
<211> LENGTH: 868
<212> TYPE: DNA
<213> ORGANISM: Glycine max

<400> SEQUENCE: 97
gatttgtcag cgagatacat agttgatagg tatctacctg ataaagctat tgacctcata     60
gatgaagcag gaagtagagc ttgtattgaa gcctttaaga agaaaaagga gcacgaaact    120
ggaatccttt ctaagtgccc agctgattac tggcaagaaa ttaaagatgt taagtccatg    180
catgaaatgg taatggcatt ggttacagta ttttcctgtt gcctgtatca attgcttaca    240
gtattagttt aagatgacat ttcttttccca ctggttcagg agaacaagct taaatactat    300
ggcgcttcta gcattgacga taccaatgaa ctcatactgg actcatattt atcttctaca    360
accaccgata atgagtatgt tatttgaccc cataatcaga gggcattcat tgtatgtat    420 ctggatttga tttctgagcg ctaacacat tatattttct ctttagacct atagaagttg    480
ggccagaaga tatagcagca gttgcttccc tctggtcagg aattcctgta cagaagctca    540
cagctgatca aagaattctt ctgttagatc ttgagaatca acttcggaag cgtgtgattg    600
gacaagagga ggctgttgct gccatttcta gagctgtgaa gagatcccgg gttggcctaa    660
aggatcctga tagacccata gctgctatgt tattctgtgg cccaaccggt gttgggaaaa    720
cagaactcgc aaaatctttg gcggcgtgtt actttggatc ggtaaggctt gacacactat    780
atgttttagc aatcatagtt agagatgatt tgttgttgt tttcttctt tttaatgatc    840 tgcaggccat gcaagatggc gtaataaa                                       868

<210> SEQ ID NO 98
<211> LENGTH: 480
<212> TYPE: DNA
<213> ORGANISM: Glycine max

<400> SEQUENCE: 98 aactttacc aaattttaa ttatgtcccg ggaactttt tccccttca attggataaa     60 agttcaagga cccaattgaa acaaaaaag gttcagggac atatttgaaa atgacaaata    120
gttcaaggac ctaattaaaa aattgtgaat ctctccaagc tagtcttttc acccctgcat    180
gttctaaact tgttgaagaa cctaagaata cggagtttag aacctgcaaa agtgagaata    240
caagcctaca aaggtgagaa tacaagccta caaaggttgg taattttaa ttaggtcctt    300 gaactttttc attttaaat aaggccctga atattttttt tcaattaggt ccctgaactt    360 attttttta attaggtcca acatggacct aattaataaa tacatacaag ttcagggaac    420
caattaaaga aaaaaaagt tcaggggacc taattaaaaa atttagtaaa agttcaggaa    480

<210> SEQ ID NO 99
<211> LENGTH: 760
<212> TYPE: DNA
<213> ORGANISM: Glycine max

<400> SEQUENCE: 99
agtatcttgc cggaaggact ccaaaattct acggttttca ttatctacag aaggttgtag     60
ataaaatcta ggacatgatt ctaccacaga atcctttctt tcccgcactg tccttaatat    120
aagtgtcttc aagaagttca ttacttgaac tgcatacatc aatgcagata tagggtctgc    180
```

```
catctgcaat cagaaagacc aaatactttc attgactcga acctactatc agatggaaca      240
actatcacat tggcatcttt atttactctt ggaaaaacac agcatagtaa agacttcact      300
aaaggtaaaa atattgtcaa gacaagtagt gcagaaaaga tttcccgaga aagaaaaca      360 attggatttc aaaagatttc catatgcaat ttagtaaagt agaaaatgaa aatatatagc      420
acttgtatgg tacatctttt cttccttgca gtcacttgag aatgaaaaaa tatggaaaca      480
cacctgagtc atgtttggtg caaaaaccat ggcaatgtta cgcgcattca tcttattaac      540
atgctcatgt aggacaacat cagccatcag attgatggtc cagtccaaga gtgaagcttc      600
agtatgaggt agatgtctca ctagttcaga acattcatcc tcagtctggc attgcattac      660
ctgctcgggt gataatgaat ctagaatgcc tgtaggaagt tccctaaacc aagccttgaa      720
aaatgcaaga ttatcaaaaa gtttctaata acatgcattt                            760

<210> SEQ ID NO 100
<211> LENGTH: 502
<212> TYPE: DNA
<213> ORGANISM: Glycine max

<400> SEQUENCE: 100
attcagaaaa ctcacttctt gctaaaagtt caacaacctg attccccaaa cctaccacat       60
cctgtaacgt agtgtaaaat tagtcccttg tgtatgtgca gaatgaatca agttatagag      120
ttttgatttt gaacaactgg ggtttcttta aaattgacct atcttgaaat gggattcttg      180
tattttcgcc ttaattcaac gcgagactag tgcttagagc cttaaatttt tcattacatc      240
tcaggttctt acccacctaa gatcattcct agcattcctc aatacctcta aaacttgttt      300
taaatattgg tcaattgaaa aaaataatgt ttaacagaat cctgggataa aattttttgag     360 gcaatgttta gtagcatgta tcaaatagct tagtgaaaga tgatttgagg tatatgatgc      420
ttaccaaaag aagatcctcc tcattaatgc caaatgcttt gcgagcctct tctaaagact      480
tcgaagaagt gctcttatgt tt                                               502

<210> SEQ ID NO 101
<211> LENGTH: 759
<212> TYPE: DNA
<213> ORGANISM: Glycine max

<400> SEQUENCE: 101
attttaagtt tgatcacaac acaagagaat tcaagtgaag acaagaggc agaaattta         60 atgtataaat aatataagga aaagaggatg gaaaagaaga atggagagaa agttaaccac      120
acataaaaga gaactcattc attgtaaatt gttgcagtga atgacacatc aaacaaaata      180
aaattatgat atacctctgt taatccaacc atgctaagtt caggatgagt gaaacaagca      240
gctgggatgc ttaaatgatt gagcacgtga tcttttccag tgacttgttc aaccactgtt      300
agacaatttt ttcatcaact gatattgctg cataaactaa attttggaaa agttacatca      360
gttaccactt acctgaaatt ccttgtgcac tggcagcatg agcaagcatc atcttgccat      420
ttgcatcacc aatacaatat aaatgaggca cctatcattc cacatcctat gtcagtaaca      480
ataagtcagg gagggataat tattgcatga gaaattgaga caaaccagct tgccattcgc      540
atcaattact cgcatgtgct catccactgg aacaaaacca cgctgtgtta ccacatcaat      600
ctgtaggtaa aagttaccaa aaatatacaa ttacttcctt tggagaaaat ctcctaatcc      660
taaagcacat ctctgtcgga attgcttaca ttctccaatc caagaccttg tgtgaacgga      720
gcccttccag ttgctattag tgcagcatcc acctgtaac                             759
```

```
<210> SEQ ID NO 102
<211> LENGTH: 457
<212> TYPE: DNA
<213> ORGANISM: Glycine max

<400> SEQUENCE: 102
gctctcaaga gagcaaatgt tgatccatca ctcgtgcaag aggtgttttt tgggaatgtt      60
cttagtgcca atttagggca ggctcctgcc agacaggctg cattaggtgc aggaattcct     120
acatctgtaa tctgcactac tattaacaag gtctgtgcat cagggatgaa aggtatgttc     180
tttttttgtt gttgttgatt tggaagggta ttccagtatt cccacttaaa tatatgaatt     240
ttaattggaa gggtcctttt cattgcagct accatgcttg cagcactcac catacaattc     300
ggtctcaatg atgttgttgt ggctggtggt atggaaagca tgtcaaatgc acctaagtac     360
attgcggagg ccaggttcgc ttttctttca tgaattgttg atacttaata cttgggcttt     420
ccgataaaag ataacgtttt ttaaatctga caaaatc                              457

<210> SEQ ID NO 103
<211> LENGTH: 659
<212> TYPE: DNA
<213> ORGANISM: Glycine max

<400> SEQUENCE: 103
aatcttgttt tttgcttcct tcacttcttc tgcatgcctt gaattttgat cttcaataca      60
actcctcagt ttgctggaca tattaagcaa gttttcaacc acttaaaaca agattatgaa     120
gacaacagag aaaaagaaa gatatggata gagatgaaaa caataaacta acagcaaaat     180
acacgataaa acttttctaa ttggacttga aatacttact cagtaattaa agcttcatca     240
caaagaaaat tcagcagtgt gagctttta gataaatcca aattgtaata tccaccaacg     300
ccttcttgaa gccaatccaa aggaaaatct tttaatatat gatcagatcc agcaattaaa     360
tcctccaatg gtttcaacca tgaattattt ccattgctag tagttaagga tggagaccta     420
aacccaccaa agtcatccat atgacaacct taatccaaga ttccaagtat atcatagaaa     480
aattatttcc cccaaaacta tacactaaca aataaataaa agctataagg gataactcac     540
tcatttcctg aatcagttag tatcaaggtc aacactctaa tttgaaactg aaccactaaa     600
gtgttttgtc ctcgacgcaa attttgttta cgcactaatt ctcgtaagat ggcttcagg      659

<210> SEQ ID NO 104
<211> LENGTH: 586
<212> TYPE: DNA
<213> ORGANISM: Glycine max

<400> SEQUENCE: 104
tggtgtcaaa agtcacatcc catttgaagg aatactacac tataaagtgg gcatccgcac      60
atgaagaggt gcttgtgttc ttctcgccgg cgtggttgag tcctctggag aatgcatatt     120
tgtggatcac agggtggaag ccctccatgg tgttcaagct tctggaaact ctcaagaagc     180
aagcgagtgg tggtgatttt gtgatgacgg aggagcaggt gaggaagatc gaggagctga     240 ggagaggac gaggatggag gaggagaagg tggagaggga gatggagagg cagcaggtgg     300
ccatggctga ccgaaagatg gtggagttgg tcaagctcac cggcagagca aggaacaacg     360
gtagtggtgg tggtggtgat gcggtggatg cggtggtgga ggtggcctta aaggggttc     420 ttgcgggggtt ggagagggtc atgaaagctt cggattgcgt gaggctcaag acactcaaag     480
gggtgttgga tgtgcttagt ccaatgcagt gtgtcgattt cttggctgca aatattgcta     540
```

```
tgcagctaag actcaggcaa tgggggaaga agaagaggga cattgc        586
```

<210> SEQ ID NO 105
<211> LENGTH: 294
<212> TYPE: DNA
<213> ORGANISM: Glycine max

<400> SEQUENCE: 105

```
agcttgcatg ctctgtagaa gaacatctac gacacaatac atgacccaag gaactatagt    60
tatatcaacc tctgaactca gacaaacccg acaaacccat gctgcttttg ctgtatcagc   120
ctcttttgtt gccttttcaa ccctttcctg tacaatgtat aatggtgatg tcattccaaa   180
cttatcataa agattaactc taccagatat atgcattaca aagcatcaag gaagctactt   240
caatcattac tcgtttctac actttaaaac tatccctaaa gccttaaaca actg         294
```

<210> SEQ ID NO 106
<211> LENGTH: 797
<212> TYPE: DNA
<213> ORGANISM: Glycine max

<400> SEQUENCE: 106

```
ttgcacgatt accctgtgtt gtggcatatc gtgcccatat tttgacagaa tggtatattt    60
ggtacaaagc gaagatacag tatatatcac ttaccaatat tcttttggac aaagccatta   120
ttcctgaagc actctttcaa tcttgcaaac cacttaactt agccttgttg ctcaagtaag   180
gctgaaattc aaattatttc gtctgtatta ctaatttgag aaagctgaga atttatcagt   240
tatagccagt atttttgttg gaatgtttga cacctgtttt tggctctata ctacagagat   300
ttattacatg atgatggttg tcgagaagaa caaataattg cagcccaaaa gattctcaag   360
cttctatggc cttcagagag aataaagctc aaccttctac aacaaaattt gaaaacttgt   420
gctgattaca ctccaagtgc agttgcagca ttgactatat aaaccatgg gaagccaatg   480
actagtatct aaggacatat ctttctgcaa gggctctggg attggatttt tcactgcaa    540
agtttgaagg tttgaagctg gaggatattt tcatttcata tgtaactgag aaaaaaatag   600
cttttcaaaag tgtagaatca agttattgat aaacatggag atggaaaagc attgctccat   660
gttttgtttc agctaactca aaaattcccg accttgcatt ttttcttcta ttgcagcttg   720
tttgtctgca ttgatttact ggtgtataat attcttatg aatgatgatg attatgatca    780
tgatctgcag gtcgact                                                   797
```

<210> SEQ ID NO 107
<211> LENGTH: 785
<212> TYPE: DNA
<213> ORGANISM: Glycine max
<220> FEATURE:
<221> NAME/KEY: unsure
<222> LOCATION: (1)..(785)
<223> OTHER INFORMATION: unsure at all n locations

<400> SEQUENCE: 107

```
aattgacgca acagtacctt acacacaaag gacatctcat gcaatcctcc aaaaaaactt    60
cactactacg tacatttatg agacagaata aggtaaaaaa aaaaactttg gaatgcaagt   120
tgaagacagg gacaaagaca agcaacttca cttggctatc cttattcctt ggtcaaattt   180
ctcaatctgt tgctcctcca tcaccaaaca gatgattgtg ggttggaaag aatagtggta   240
catcaacacc tcttttcatt ttaataaact aataataagc atctcaaatg tgtctttcct   300
gtttccacat taagtgatta agggatacaa gaaaattgtg gcatagtttt ttttttttta   360
```

| | |
|---|---|
| caaatgatgt tagttctcac ctggaagcag aagatgagtt gagcaaaaca aaattgatta | 420 |
| gatcctcaat tttgcctcct tggtacttct aattctgtaa atttggaaat ttgaaagtgt | 480 |
| tgcattattt ttctttatta ttttctctta atatgaatat attcataaca ataattcaaa | 540 |
| atcactagag agcacctact ctaaattgat ttttatagct aaatcttcaa aggaggcaat | 600 |
| aagaattatg ctttaataaa tcgaagggct ataccctctgt ctaatgccat ggatgctctc | 660 |
| aaggagttca attgggttgg tgcaccctaa aaattctttg gggctctttt tctttttccc | 720 |
| ggnaccaagg ttgggaacct ttcaaaccag gaactggtcg ggggtggact tgccctgggg | 780 |
| gtgtt | 785 |

<210> SEQ ID NO 108
<211> LENGTH: 890
<212> TYPE: DNA
<213> ORGANISM: Glycine max

<400> SEQUENCE: 108

| | |
|---|---|
| attttacccct gaggttttgc catatggtga aactttcttc catgagccag ttggtagagc | 60 |
| ttctgatggt cgccttatca tagatttcat tggtatatac cttttcaata attctcatca | 120 |
| ttttttttgct ttatttctta ttcatttatt tgtgaaacac gatcaaatga catgtttgct | 180 |
| ttttctatct actttgtttt cttttttcttt aatcatcatg tggtgtctca caacacaagc | 240 |
| taaatcttct tttctttgag ttttgttcca caaagattgg attccagttt gtgttgttat | 300 |
| tggagttata agatacatgt ggttgaaggg agaagaggga agggtgatgg aggtcatgag | 360 |
| ttagaatctt ttttattaac aaaaattaac aaattaacaa ctaatatata ttgactgata | 420 |
| aaaagaattg tgttgtcatt gactaagtga ccaacacaaa catctctacc caaatgaata | 480 |
| aagttgggat tcaataagaa tgagttgtga aattttttta cacaatatct ctgtctacca | 540 |
| ttatctattt agcagccata gaatcctatg atggtcatac ttacaaagtg gtacataaaa | 600 |
| aatataaagt tttcacgaag tgaaaattta atatgagaag atcataatat atatattaag | 660 |
| ggatctagtt caattagttg aagtgtatat aagtattgta aatttcctct tatcgtgttc | 720 |
| aatttctgca tatcaaaaaa tatatcataa tatatatagt tctattgcca agaaactatc | 780 |
| atactagtga tttggtgcca tttgtgtttg cagcccagca tctaggtttc ccattcttga | 840 |
| gtgcatacat aaaattcaatt gggacaagtt ataggcacgg tgcaaacttt | 890 |

<210> SEQ ID NO 109
<211> LENGTH: 1236
<212> TYPE: DNA
<213> ORGANISM: Glycine max

<400> SEQUENCE: 109

| | |
|---|---|
| atccttgcta tatatatcgg aaagttgaaa agctggtggt ggctgatgat ggtgccaatt | 60 |
| actagtacat gactcgtcta ttatgaaacc tgtttctggt ttaataacct cagtgtagat | 120 |
| agattgagag gtttgaattt gatgattctg cgctgtgttg tttcccagaa taaacggggt | 180 |
| gttaagatac tcagaccatt ttagatcttc ttgttctgct tgtagaggca ctacttgagc | 240 |
| ctctttgtta atgttaacaa tcttcataga ctctgccacc ccccacgtgc tgtcaaggta | 300 |
| gtttgtgcta ctttgtaact gcatattccc attgttttttg tttgtgttgt tacttgtttc | 360 |
| ccagttttga acccccatcag atgaaatgga agaagggttg ttgttattag attggagctt | 420 |
| cacatgttgt gttgggaaaa ttgaagggag catggaggag gaggttatga tggagttgtt | 480 |
| attattaatg tctgaagaag tggagggtag aatgaaacaa agagaggtgt tggggtttga | 540 |

```
agagagggcc atgcttgttg ttgttccata gttcaagtgc tggaaggaga agtatgatcc    600
taccaaatca gaagtgttgt tgttgttgtt ttcgtggcag gtggtggtgg tggtgccaaa    660
cctatctagg aacagttcct gggtggaact agtagtggaa acttcaagag ggtatctctc    720
tgatgaagaa ttaggcatgg tttttggtgg ctgatgatga tcaaccaaat tactcactac    780
ttcattggat cccacagagg ctttctgagt gcttttgtcg gttgagggtg gcatcatatt    840
catgtccttg tcgttctcaa cctcagagag tggcttgtgt gtggttgggt caatgcctct    900
ttgcctcagc ttcttcttca ggcacgagtt ccataggttc ttaatctcat tgtctgttct    960
tcctggtaac tgtgctgcaa tctgagacca cctgataaag cacccaccaa gctaaaaatt   1020
aataaaaacc atacatcaag aacaaaagtc aaagtaataa ctgtacgctg aaaaaaaaaa   1080
aaaaaaaaat ggccttgtat gagatatata aatatataac tatataacta aaactacctg   1140
tttccaagaa ctgcatgaag ttcaacaatc atgttctctt cttgctgtga aatgctcct    1200 ctcttcaaat caggccttag ataatttatc cacctc                             1236

<210> SEQ ID NO 110
<211> LENGTH: 1212
<212> TYPE: DNA
<213> ORGANISM: Glycine max

<400> SEQUENCE: 110
atctcgataa tttcggagaa atcaggtctc aatgtaggat cttgctgcca gacctctcaa     60
gaagctccac aaactttgga tgagtgttct tcgggatggt gggtcgcaaa ccctgaaatc    120
catttaaagt tatggtagga aaaaattact atttgtacga tacacatatt tccatttaat    180
catataaaaa ccgctttcct caaaatttga gtttattcta ccactgatgt ttaaggaaaa    240 aaatacccttt tgaaccactc ctatagctgc ctgtaggggg gttaaatatt cgtatggaag    300
ctggcaagaa aaacacaata atttacatga gaggaaaact aatactgtaa gagtcataag    360
gtgttacaaa taagaaatac cttttccggtg agcaactccc ataaacaat tccaaaacta    420 aatacatcag ccttgtgatc atacggcttg tgttctataa ccttcaatac aaaggaatca    480
tggtaagaaa gatgacaata tgagttatac ctctcatcta tcttagccac cagaaaatat    540
ttaaacaaga aaacaaaaac tattaaacag catattttag tgggctagta ctaacattca    600
gggcctgaga tttatcaaac cttcaaatct ttcagcaaga aaaacagcaa tgaacaattg    660
atttaccaca ctacatttcc ccagatatta aaaagttaa tactattatt ttgcccgatg     720
tttgaactga acattttcta ccgataactc gaccttaatt gttattctga aatataatgc    780
agcaataatc ctttttctca tactaaatcc atcgtacaat ctaatctcat aaaatttggt    840
gaataaagtg atgggggaaa gacattatag aaggagaag gaaagtcgt gggtttgatc     900 ccctctgcta atatatgacc acatgacagg acacttagct acagtaatgt catccatttc    960
atttattata aatttccaga acgacaggtt cacataattg atcaaacatc aaaataagat   1020
ttaacactag acatctatt aggttgaaaa aaccaattaa aaaagtgcaa actcctatgg   1080
taatataaca agaaaacaga caacaggtgt tgaaaagcta acaatgtca tcaaaactat   1140 ttgaacaact tgatggcagt aacatgagaa gatcaaatac ctcaggagcc atccatcgat   1200
atgttccagt tt                                                      1212

<210> SEQ ID NO 111
<211> LENGTH: 774
<212> TYPE: DNA
<213> ORGANISM: Glycine max
```

```
<400> SEQUENCE: 111
ggaaaaactt tgagacaaaa actaaaacac ttatgaaatt agacaaaaga atgcaatatt    60
aacagaatgc tacaacattt caagaggacc caaacgtaga ttataaggag aataatgaat   120
cctcctattt aaaacagaaa gaaactccta tcctatctaa aacagaaaga acccaatgag   180
ccaaagtggc tcaaaaatgc aataaagtat tccaatattt tcgcatacaa atgattgatt   240
ctttgaagca gccattaacc aagaaccatc atagagacaa tcctatccta tgacgactgt   300
aaagggaaag aggtgctctt gaaaatacac gcatttcatt acaaccaaat gcactactag   360
ataactacat atactgcaca atgcgataaa atttaacact ctttgttcct ttcaaaacct   420
ttaaggcatg taaagagaaa agctccaacc tatgattgga gaaactcatt gttggctagg   480
aaccccaaaa caattcagca ggtgtaccac aaaagtggcc tacctatagt attatcagct   540
tattttagca tgtttatacc tagatgtctc tatttcttta tgaacttcaa tagttcaact   600
accatttgat gaatgtgtcc atgatcatat cataacttat atcacgcaaa cttcagaggt   660
tattatcttt tttgtttctc attgtattct acaccaatga ggtaaaacaa gcgagcccca   720
aacgcatgat gaaacataat catccattgt tgctacttgt cagatcacct cttg         774

<210> SEQ ID NO 112
<211> LENGTH: 1080
<212> TYPE: DNA
<213> ORGANISM: Glycine max

<400> SEQUENCE: 112
aacatcccag ccttttatta ttaactatat ctataaaaat attcttgcag caactttaag    60
tattataatg gagattatat atcattaact ataatggcac ataatttagt tactgcactc   120
aaaatagtag taaaaaatat acatgataag gggtttggct tgataaatag gagacaaaac   180
taaaagatca attgatccag catttatgct cttaaaaaat agcagtagta aacagttacc   240
actagttgtt ttcctatatt cagcattttt atgtttccta cctccagcag cgcgcataca   300
attgatccat tattatggca ggatgtgttg tataataaat aaaataata attaagttaa   360 aaacaattga gatccattta acacacccttt gcaaacattt ccaagctctt aatgatttca   420
gaagcaaaca gatcccatgt ttcttgtata tataactcaa taaatctgaa agcgtatcta   480
aggcccatca tcgtcttgtt tgaatccata gttgatgttt agatcatcgg gtgcaaagct   540
tttaagaact atatacgtat taagaaatta attaaatata tatacttgcg cagatggtga   600
tccgatcgag gaaactagct agacaacaat atatgtgaac aaagagaaaa atatcttgaa   660
tatagacaaa aaataactag tggaaaatat taacctccta ggggattaaaa cttatttaac   720 cacagagact aagtgaatgc ttaattagtt gataagagaa gttttttttaa aaccaaaaca   780 ttttggtttt ctattttctt ttcgctatcg cagtttcttc cctcacttct attgtctaac   840
aatcattttt tgaaatttgt tttatagaac attttttaaaa atgaaaaaca caatcaaaca   900
tggccttaat attttgtttc ttatcgccag aacttgttgc tccacagacc tctcttcagt   960
tgctgctctc cctcccaaaa aggcaagaca atgcataagc atttctgtac tttcagtttt  1020
accaacacca ctttctccac taaccaaaat agattggctt tcttcttcgt ttatcatctt  1080

<210> SEQ ID NO 113
<211> LENGTH: 969
<212> TYPE: DNA
<213> ORGANISM: Glycine max

<400> SEQUENCE: 113
```

```
tgttgaattg tccttgagct tgatgatgat gaccttagtc ctgctccaaa accttgcata    60
aatgatttct tcccaaccat tgtcttgaag gcagtatcaa tgttttcttg ttccgttgtt   120
tccaccactt cctgagaatc ttctatttga catctcttct cattagtttg ttcagcaact   180
ttgtcctaca atgaattggt acaacaattg gtcatttaga gaagacgggg aacatcaaat   240
caaatcatat ataagaaaat atagcagtaa tgtaaaatgc agttacattg atttccttag   300
atgctttgtc aatccattcc ccatttcccc ttttgtgtgt caactggcaa aatgtctgca   360
aatcaggctc ctttccggtc actgggtcac gctgttaaaa ttatgtttat taaacattat   420
acaaaaaatg tcataaaatt agatgagaca atcataagag caaacattga gttcaacaga   480
aatctcactg catcattgct gacagctaga aaggattttg agcctgcaga gtgtattaa    540 ttccttcaac aaaaagcagc gtctgcacca ccctcacttt atcatcctga atcattgtat   600
caatatttga aatatcaata tcaaatctct atataatagg acaatgcaaa gtaaaactaa   660
aaaagaccat gaggtaattt cacttttcaga atcaacattt ttccttctct gtgggaccca   720
cacggctcat ttcagcatat ggtgcgtcaa aacaaaatat ataaaacaaa aacaaaaaa    780 acaatgtaaa ggcaaaacaa aaagtttctc cattcctcct cagtagagag atttggcaat   840
atcaaacaat ttcatcatac ataataatat aaaacaaaat gaagaagcaa aacaaaagga   900
attgaagttg aagggaatga cttacatcac ttccacccat caaaggcaca agaaatgaag   960
gaatcatga                                                           969

<210> SEQ ID NO 114
<211> LENGTH: 611
<212> TYPE: DNA
<213> ORGANISM: Glycine max

<400> SEQUENCE: 114
gcagtgagca agacattctt tgattttgct gaaagaaaaa taatcatggt gtctatttt    60 caaggaacta gtgccgtagt gggccttaag gtttacatgg agtctatttt tcaagtttat   120
aagcatactt taacatacat ttgaggaaat catacgatat tgaagcattg aggggaagtg   180
tcgtaatttg gaactacctg atccttgttt ggagaataaa ttgcagaagg aagcttttt    240 tgcaatttgg gatttgaact ctgatgaaac tatagctggt ttggaaattg caaggataga   300
cggtgatgaa ataatgtggt aggaaatgca aatgatagtg tgtcttgaca gtgggcacgc   360
cgaaacatga ttgttacgtc aaccaaaact actcaattag gggagagcta catctcatta   420
tacagttgga ttctcagcaa aatatttatg tggaaagctg agaactaatg gtttcatagg   480 atactttgc ttaatttggg ggtgttttca tttggtcaat ttagtagtac gttcaatggt    540
taatatatat gccttgaaaa ataaatattg tgctcaacaa attcgcttct ccgctcttcc   600
tttccaagcg g                                                        611

<210> SEQ ID NO 115
<211> LENGTH: 751
<212> TYPE: DNA
<213> ORGANISM: Glycine max

<400> SEQUENCE: 115
aaatttccct atccctaacc tcctctacag aatcaaaata accaacatct ttagtttctt    60
caacttcatt gcctctgacc acgtactttt catctttccc ttcctcattt cgaccagaac   120
ccatattcac tccatcattc ttttttcgct gattctgaaa cagatcaggc atgacagaaa   180
tgtcaccact ctgcaacaaa aaatcatcca ggtctcgcga tccaaatgcc acggaagaat   240
```

```
tcataaacaa agagttctcg tttctcactt ccggctcctc aaaataaccct ttattttttcc    300 acaaatacat ttcatttcca ccatcaccat cactaccata gtcatacata gaatcatcac    360
cctccgataa ctcctcttct tcctcctcct ccttttcttc ctcctcctcc ttttcttctt    420
ccacttcttc ttcttctctt ttctcaattt ccaattcaaa accatttcca ccactcactt    480
caccgttccc tttcgactct tcgatccgat gattaagccc gataaactcc gacgaatcga    540
gcgctgtcat agagagctcc tcactgcaat caccgtacat ctccaatcca ctggaaccgt    600
accgcaaact ccgcctccgg tcgccgccgc cgccgcgatt caccctccgcg ctccttttc    660 ccaaactgaa attctcgaaa ccctcgccgc cggcagaagc gaaatcgcaa tcggagaatt    720
cgtggaagag cgtaacggcg ctgcaggcaa c                                  751

<210> SEQ ID NO 116
<211> LENGTH: 833
<212> TYPE: DNA
<213> ORGANISM: Glycine max

<400> SEQUENCE: 116
actggtgtac attttaaact cgattttata gttgaaaaat atagacaaac agatagaaga     60
cagtgaatat ctttcatatc tgaaaattca atttcaaagt ataatcatta ttagtttgtt    120
tggaatatta tctcaaagtt tccaaccgtc cacatgcact tttcaaggca ctaaacgaag    180
aaagaactcc aacgttagat tgagaatgac ttagagttaa agtatatcta aacatataat    240
aaatatattt aaataatatc tattaatttc agttaacagt ttcccctctt tactttaatc    300
tctacaaatt caaattcaaa gtataatcat tatagtttgt ttgagttatt gttttaaagc    360
ttcaaaatgc ctacatgcat tttttaagac actaaatgga aagaaaaaaa aaggttata    420 aaattgatta gagagtaaaa gaagaaaaaa gggaaaaaaa gatcacaaat ttgattcact    480
agttaataaa aaattaacaa ttaatcacta atgaaataaa agtacattta aaatttttaaa    540 tatataaaca ctatgagata ctaaaatatt atctattaat ttcaattaac agctatcatt    600
gaaagaaacg agaaaaaatg gagacaatgt ttttcgttta gtgtgtttga attgttttca    660
tggcactaaa cgaaaaaata aataagaaa ctgtcatcga actgaatata acgtcgactt    720
gtgttggatg caaaaaaaat tccaacacac gaggttatga gtatgacatt ctgttaattg    780
gatatttatt ttccatggca aatatgaact tcgactgaac cacaatgaca caa           833

<210> SEQ ID NO 117
<211> LENGTH: 410
<212> TYPE: DNA
<213> ORGANISM: Glycine max

<400> SEQUENCE: 117
attcttgcta aatgaaacaa aacattattc tgcaaaggag tgcgaccccc accctagata     60
ccttcaactt ttttttcttt gaactttaa actcggattc agttcgatgg ccaataaaaa    120
gccatcataa ggaaactcta agcaaagtt aacatagaat caaacaaaac tacagtttca    180
acattgtttt tcctccttat cctaaatcaa aacaatgtgt caaggtctaa cagaggatac    240
ataaaatttt acgtctaaag taagtaacac ttcctgagat gagaaaaaaa aaacaaaaat    300
gaaaacagaa ctaagattga gggcatgaaa tgatctattg atgtgggaac tctttctgcc    360
tacttttgct tgacaacctg aattcctgag gcgattgtag taccccttcat           410

<210> SEQ ID NO 118
<211> LENGTH: 707
<212> TYPE: DNA
```

<213> ORGANISM: Glycine max

<400> SEQUENCE: 118

```
tactcccgaa gacactacaa cagaatttct ttttgttttt cttctccttt gtcgcattaa      60
acgtacaagc cttaattact ttcttttcaa taaggtaatc ataatcctat ttattttgcc     120
atgtcccatc aatctaaact tttttttctt ctttcattga atcccatcaa tctaaaccgc     180
ctctatagtt aaacttgtta cggtacgtac tgtacaaatt aactaactat ctgtttattg     240
attgaatgta tagttctctt tttatatta aaaataaaaa atatgttaca aattgttggt      300
agttatctac actacacatg cacatgcttc accccaaaag cacaaaatgg ttttgacatt     360
cttccaattg atgttgaaaa tacctttac ttccagaagg catcttcaag taaatggcaa      420
ctatggaaca cgtggcttct gtacctgtaa ttctgtcaac acataaaaac aagaacgaat     480
ttttttttaa tctcagtatt ttctagtttt aaaccgtgac acatgatgac cactttggtg     540
caaattaaga aggtagattt atgtatttaa ttggactttt ttttttgcaa gttatctagc     600
tttgatttgc ggataattcc tattcaatag ttgaatctac tggaaaattt gtaccttcca     660
ctcttggtca gcataccttc atggtttctt tttatttctt taagcaa                    707
```

<210> SEQ ID NO 119
<211> LENGTH: 856
<212> TYPE: DNA
<213> ORGANISM: Glycine max

<400> SEQUENCE: 119

```
gtcctggagc gttatgggga gctagatttg gtcctgccgg taatgggaga ggatgcttca      60
gtgataccac tccagatctc tcgtttgtaa tctcaggagg ctttatgcag ccccttccg      120
ggtggcatcc gttgtcaaat gttgtgttga acttgagtag ctgggaggtg ctgtgactcc     180
tagagtatga ataatctcat tagtaacgca gaaatgcgta atttggaatg acatgcactc     240
gcatttagtt atatagttgc caataatatg gtaacgcatt ggtgtttcg ttgttgtgtt      300
taagctctac cgtgtttagg acttatttta tcattgaaga actttgcaca atcattgtaa     360
gtagaccggt aggacagtag gatatataca tggatgtatg gttcgtgcct caattcatcc     420
agaacagtat atttatcata cggaactcat cgatggtgtg aagtttgctg ctcccgatga     480
ttggagttcc attgcaatcg aaagtgattc caaaaaggta ggtaacatta atagaaatgt     540
aacagattgg tctgaactag gtgttatta tgagaggcat aagattagca gtcattgttt      600
gatgaatgta tttccaactt tgttcctagg aaaggaacta aatttgccca ccaagttgac     660
aatgggcaca ttcctcggtt gaaagtttgg cttgggggtt taattccttg gtgatatact     720
ctgaatctgt tgctggttaa tgaatttgat ggatatttga aaagaaaaa tatgtagaga      780
tagctaaact aacctaaaag gggtttaaga attttagctt attgatgatc ggatttatcc     840
aaaatatggc cttttt                                                     856
```

<210> SEQ ID NO 120
<211> LENGTH: 858
<212> TYPE: DNA
<213> ORGANISM: Glycine max

<400> SEQUENCE: 120

```
aaaattaact tagtccgtgt ttgaatgaag ctaatttaga aagaaagaaa attaatttcg      60
gtcaaaaatt gatttaaaaa tgaagtgatt tatgcttgat tgtttttata ttaaaacaaa     120
attagtagaa aaatccatta taaatcgct tcactcaaaa ttgactttgg agccagaatc      180
```

```
aatcaattct tcaacacgca accaaaaaca tgaacagttt accttaaaaa atcaagttag      240
ctggtacagt ggtacctcaa catgatttta tctaacataa cgagaatcca aacatgattt      300
taatcaacat gataatgact cctgaatgat taatagtgtg tttggattag cttcatggcg      360
aaaaataatt aattattatt ttttccatgg tgaaggtaaa gcaacaaata gttccttcca      420
ttattgatgg tatcaccatg attttgtgag ttagaattga ttttgacac actgaagagt       480 ttggaaaagc aaacctgttg aaaacaagtg acaaggtatc aaaattgaga ggatcctcca      540
agaaaaactt caactgtgca gctctcttgg cagtggagaa tctaacaaca ggtgccctag      600
acatgcaatc cctcaaaacc acactgctgg ccccaccaga agcatagatg gccttgcacc      660
ctctgttggt actcgccaca aggcaccctt ccgtggtggc catcggcaca gtgtattcga      720
atccatccaa caacaacggc cccgccaccc ctaccggaat ctgcacatac cctaccggca      780
tttcgcagca ctgccctaaa atggagtcgt agtcgaaccc ctccagcggc aggccctcaa      840
gcgactgccc cgtcaggc                                                   858

<210> SEQ ID NO 121
<211> LENGTH: 18
<212> TYPE: DNA
<213> ORGANISM: Artificial Sequence
<220> FEATURE:
<223> OTHER INFORMATION: synthetic probe

<400> SEQUENCE: 121
atattgacag ataaaaag                                                    18

<210> SEQ ID NO 122
<211> LENGTH: 18
<212> TYPE: DNA
<213> ORGANISM: Artificial Sequence
<220> FEATURE:
<223> OTHER INFORMATION: synthetic probe

<400> SEQUENCE: 122
atattgactg ataaaaag                                                    18

<210> SEQ ID NO 123
<211> LENGTH: 16
<212> TYPE: DNA
<213> ORGANISM: Artificial Sequence
<220> FEATURE:
<223> OTHER INFORMATION: synthetic probe

<400> SEQUENCE: 123
cttgcaagtc atgcta                                                      16

<210> SEQ ID NO 124
<211> LENGTH: 15
<212> TYPE: DNA
<213> ORGANISM: Artificial Sequence
<220> FEATURE:
<223> OTHER INFORMATION: synthetic probe

<400> SEQUENCE: 124
tcccttgcat gtcat                                                       15

<210> SEQ ID NO 125
<211> LENGTH: 20
<212> TYPE: DNA
<213> ORGANISM: Artificial Sequence
<220> FEATURE:
<223> OTHER INFORMATION: synthetic probe
```

```
<400> SEQUENCE: 125
actcaagttt aagatttgaa                                              20

<210> SEQ ID NO 126
<211> LENGTH: 19
<212> TYPE: DNA
<213> ORGANISM: Artificial Sequence
<220> FEATURE:
<223> OTHER INFORMATION: synthetic probe

<400> SEQUENCE: 126
aactcaagtt tatgatttg                                               19

<210> SEQ ID NO 127
<211> LENGTH: 16
<212> TYPE: DNA
<213> ORGANISM: Artificial Sequence
<220> FEATURE:
<223> OTHER INFORMATION: synthetic probe

<400> SEQUENCE: 127
attcttcagc atgatc                                                  16

<210> SEQ ID NO 128
<211> LENGTH: 16
<212> TYPE: DNA
<213> ORGANISM: Artificial Sequence
<220> FEATURE:
<223> OTHER INFORMATION: synthetic probe

<400> SEQUENCE: 128
attcttctgc atgatc                                                  16

<210> SEQ ID NO 129
<211> LENGTH: 18
<212> TYPE: DNA
<213> ORGANISM: Artificial Sequence
<220> FEATURE:
<223> OTHER INFORMATION: synthetic probe

<400> SEQUENCE: 129
tggtaagtag ttaaatga                                                18

<210> SEQ ID NO 130
<211> LENGTH: 16
<212> TYPE: DNA
<213> ORGANISM: Artificial Sequence
<220> FEATURE:
<223> OTHER INFORMATION: synthetic probe

<400> SEQUENCE: 130
tggtaagcag ttaaat                                                  16

<210> SEQ ID NO 131
<211> LENGTH: 16
<212> TYPE: DNA
<213> ORGANISM: Artificial Sequence
<220> FEATURE:
<223> OTHER INFORMATION: synthetic probe

<400> SEQUENCE: 131
tggtaggcat caataa                                                  16

<210> SEQ ID NO 132
<211> LENGTH: 17
<212> TYPE: DNA
```

```
<213> ORGANISM: Artificial Sequence
<220> FEATURE:
<223> OTHER INFORMATION: synthetic probe

<400> SEQUENCE: 132
atggtaggca ttaataa                                                  17

<210> SEQ ID NO 133
<211> LENGTH: 13
<212> TYPE: DNA
<213> ORGANISM: Artificial Sequence
<220> FEATURE:
<223> OTHER INFORMATION: synthetic probe

<400> SEQUENCE: 133
ctcaaccaaa agc                                                      13

<210> SEQ ID NO 134
<211> LENGTH: 15
<212> TYPE: DNA
<213> ORGANISM: Artificial Sequence
<220> FEATURE:
<223> OTHER INFORMATION: synthetic probe

<400> SEQUENCE: 134
aactcaatca aaagc                                                    15

<210> SEQ ID NO 135
<211> LENGTH: 14
<212> TYPE: DNA
<213> ORGANISM: Artificial Sequence
<220> FEATURE:
<223> OTHER INFORMATION: synthetic probe

<400> SEQUENCE: 135
ctggcagtgc agca                                                     14

<210> SEQ ID NO 136
<211> LENGTH: 13
<212> TYPE: DNA
<213> ORGANISM: Artificial Sequence
<220> FEATURE:
<223> OTHER INFORMATION: synthetic probe

<400> SEQUENCE: 136
ctggcggtgc agc                                                      13

<210> SEQ ID NO 137
<211> LENGTH: 13
<212> TYPE: DNA
<213> ORGANISM: Artificial Sequence
<220> FEATURE:
<223> OTHER INFORMATION: synthetic probe

<400> SEQUENCE: 137
ccgctagcct tca                                                      13

<210> SEQ ID NO 138
<211> LENGTH: 13
<212> TYPE: DNA
<213> ORGANISM: Artificial Sequence
<220> FEATURE:
<223> OTHER INFORMATION: synthetic probe

<400> SEQUENCE: 138
ccgctagctt tca                                                      13
```

```
<210> SEQ ID NO 139
<211> LENGTH: 16
<212> TYPE: DNA
<213> ORGANISM: Artificial Sequence
<220> FEATURE:
<223> OTHER INFORMATION: synthetic probe

<400> SEQUENCE: 139
catattgcga cattaa                                                        16

<210> SEQ ID NO 140
<211> LENGTH: 15
<212> TYPE: DNA
<213> ORGANISM: Artificial Sequence
<220> FEATURE:
<223> OTHER INFORMATION: synthetic probe

<400> SEQUENCE: 140
ctcacgacat attac                                                         15

<210> SEQ ID NO 141
<211> LENGTH: 16
<212> TYPE: DNA
<213> ORGANISM: Artificial Sequence
<220> FEATURE:
<223> OTHER INFORMATION: synthetic probe

<400> SEQUENCE: 141
actccattct ggtctt                                                        16

<210> SEQ ID NO 142
<211> LENGTH: 17
<212> TYPE: DNA
<213> ORGANISM: Artificial Sequence
<220> FEATURE:
<223> OTHER INFORMATION: synthetic probe

<400> SEQUENCE: 142
ctccattctt gtcttat                                                       17

<210> SEQ ID NO 143
<211> LENGTH: 13
<212> TYPE: DNA
<213> ORGANISM: Artificial Sequence
<220> FEATURE:
<223> OTHER INFORMATION: synthetic probe

<400> SEQUENCE: 143
ttgtgcatac ccc                                                           13

<210> SEQ ID NO 144
<211> LENGTH: 13
<212> TYPE: DNA
<213> ORGANISM: Artificial Sequence
<220> FEATURE:
<223> OTHER INFORMATION: synthetic probe

<400> SEQUENCE: 144
ttgtgcagac ccc                                                           13

<210> SEQ ID NO 145
<211> LENGTH: 15
<212> TYPE: DNA
<213> ORGANISM: Artificial Sequence
<220> FEATURE:
<223> OTHER INFORMATION: synthetic probe
```

```
<400> SEQUENCE: 145
acacaagcgc aatta                                                    15

<210> SEQ ID NO 146
<211> LENGTH: 15
<212> TYPE: DNA
<213> ORGANISM: Artificial Sequence
<220> FEATURE:
<223> OTHER INFORMATION: synthetic probe

<400> SEQUENCE: 146
caagcacaat taaat                                                    15

<210> SEQ ID NO 147
<211> LENGTH: 13
<212> TYPE: DNA
<213> ORGANISM: Artificial Sequence
<220> FEATURE:
<223> OTHER INFORMATION: synthetic probe

<400> SEQUENCE: 147
cagtgcgctg gac                                                      13

<210> SEQ ID NO 148
<211> LENGTH: 15
<212> TYPE: DNA
<213> ORGANISM: Artificial Sequence
<220> FEATURE:
<223> OTHER INFORMATION: synthetic probe

<400> SEQUENCE: 148
cagtgtgctg gacta                                                    15

<210> SEQ ID NO 149
<211> LENGTH: 18
<212> TYPE: DNA
<213> ORGANISM: Artificial Sequence
<220> FEATURE:
<223> OTHER INFORMATION: synthetic probe

<400> SEQUENCE: 149
tattcttgtg caaaccag                                                 18

<210> SEQ ID NO 150
<211> LENGTH: 17
<212> TYPE: DNA
<213> ORGANISM: Artificial Sequence
<220> FEATURE:
<223> OTHER INFORMATION: synthetic probe

<400> SEQUENCE: 150
attcttgagc aaaccag                                                  17

<210> SEQ ID NO 151
<211> LENGTH: 16
<212> TYPE: DNA
<213> ORGANISM: Artificial Sequence
<220> FEATURE:
<223> OTHER INFORMATION: synthetic probe

<400> SEQUENCE: 151
acatgtttcc atttgg                                                   16

<210> SEQ ID NO 152
<211> LENGTH: 16
<212> TYPE: DNA
```

```
<213> ORGANISM: Artificial Sequence
<220> FEATURE:
<223> OTHER INFORMATION: synthetic probe

<400> SEQUENCE: 152
atgtttccca tttggt                                                     16

<210> SEQ ID NO 153
<211> LENGTH: 19
<212> TYPE: DNA
<213> ORGANISM: Artificial Sequence
<220> FEATURE:
<223> OTHER INFORMATION: synthetic probe

<400> SEQUENCE: 153
caattgctta cagtattag                                                  19

<210> SEQ ID NO 154
<211> LENGTH: 18
<212> TYPE: DNA
<213> ORGANISM: Artificial Sequence
<220> FEATURE:
<223> OTHER INFORMATION: synthetic probe

<400> SEQUENCE: 154
aattgcttac agttttag                                                   18

<210> SEQ ID NO 155
<211> LENGTH: 17
<212> TYPE: DNA
<213> ORGANISM: Artificial Sequence
<220> FEATURE:
<223> OTHER INFORMATION: synthetic probe

<400> SEQUENCE: 155
aaactccgta ttcttag                                                    17

<210> SEQ ID NO 156
<211> LENGTH: 16
<212> TYPE: DNA
<213> ORGANISM: Artificial Sequence
<220> FEATURE:
<223> OTHER INFORMATION: synthetic probe

<400> SEQUENCE: 156
caggttctaa actcag                                                     16

<210> SEQ ID NO 157
<211> LENGTH: 17
<212> TYPE: DNA
<213> ORGANISM: Artificial Sequence
<220> FEATURE:
<223> OTHER INFORMATION: synthetic probe

<400> SEQUENCE: 157
ccttctgttg ataatga                                                    17

<210> SEQ ID NO 158
<211> LENGTH: 16
<212> TYPE: DNA
<213> ORGANISM: Artificial Sequence
<220> FEATURE:
<223> OTHER INFORMATION: synthetic probe

<400> SEQUENCE: 158
ccttctgtag ataatg                                                     16
```

<210> SEQ ID NO 159
<211> LENGTH: 17
<212> TYPE: DNA
<213> ORGANISM: Artificial Sequence
<220> FEATURE:
<223> OTHER INFORMATION: synthetic probe

<400> SEQUENCE: 159
caatacctct aaaactt                                                  17

<210> SEQ ID NO 160
<211> LENGTH: 17
<212> TYPE: DNA
<213> ORGANISM: Artificial Sequence
<220> FEATURE:
<223> OTHER INFORMATION: synthetic probe

<400> SEQUENCE: 160
caatacctct taaactt                                                  17

<210> SEQ ID NO 161
<211> LENGTH: 16
<212> TYPE: DNA
<213> ORGANISM: Artificial Sequence
<220> FEATURE:
<223> OTHER INFORMATION: synthetic probe

<400> SEQUENCE: 161
tcatcctgaa cttagc                                                   16

<210> SEQ ID NO 162
<211> LENGTH: 15
<212> TYPE: DNA
<213> ORGANISM: Artificial Sequence
<220> FEATURE:
<223> OTHER INFORMATION: synthetic probe

<400> SEQUENCE: 162
tcatcctgaa attag                                                    15

<210> SEQ ID NO 163
<211> LENGTH: 14
<212> TYPE: DNA
<213> ORGANISM: Artificial Sequence
<220> FEATURE:
<223> OTHER INFORMATION: synthetic probe

<400> SEQUENCE: 163
aggttcgctt ttct                                                     14

<210> SEQ ID NO 164
<211> LENGTH: 14
<212> TYPE: DNA
<213> ORGANISM: Artificial Sequence
<220> FEATURE:
<223> OTHER INFORMATION: synthetic probe

<400> SEQUENCE: 164
caggtttgct tttc                                                     14

<210> SEQ ID NO 165
<211> LENGTH: 17
<212> TYPE: DNA
<213> ORGANISM: Artificial Sequence
<220> FEATURE:
<223> OTHER INFORMATION: synthetic probe -continued

<400> SEQUENCE: 165
ccatccttga ctactag                                                  17

<210> SEQ ID NO 166
<211> LENGTH: 17
<212> TYPE: DNA
<213> ORGANISM: Artificial Sequence
<220> FEATURE:
<223> OTHER INFORMATION: synthetic probe

<400> SEQUENCE: 166
tctccatcct taactac                                                  17

<210> SEQ ID NO 167
<211> LENGTH: 15
<212> TYPE: DNA
<213> ORGANISM: Artificial Sequence
<220> FEATURE:
<223> OTHER INFORMATION: synthetic probe

<400> SEQUENCE: 167
caaatatgca ttctc                                                    15

<210> SEQ ID NO 168
<211> LENGTH: 16
<212> TYPE: DNA
<213> ORGANISM: Artificial Sequence
<220> FEATURE:
<223> OTHER INFORMATION: synthetic probe

<400> SEQUENCE: 168
acaaataagc attctc                                                   16

<210> SEQ ID NO 169
<211> LENGTH: 18
<212> TYPE: DNA
<213> ORGANISM: Artificial Sequence
<220> FEATURE:
<223> OTHER INFORMATION: synthetic probe

<400> SEQUENCE: 169
tttcaacttt taattcca                                                 18

<210> SEQ ID NO 170
<211> LENGTH: 15
<212> TYPE: DNA
<213> ORGANISM: Artificial Sequence
<220> FEATURE:
<223> OTHER INFORMATION: synthetic probe

<400> SEQUENCE: 170
aactttcaat tccat                                                    15

<210> SEQ ID NO 171
<211> LENGTH: 16
<212> TYPE: DNA
<213> ORGANISM: Artificial Sequence
<220> FEATURE:
<223> OTHER INFORMATION: synthetic probe

<400> SEQUENCE: 171
atggttgtcg agaaga                                                   16

<210> SEQ ID NO 172
<211> LENGTH: 16
<212> TYPE: DNA

-continued

<213> ORGANISM: Artificial Sequence
<220> FEATURE:
<223> OTHER INFORMATION: synthetic probe

<400> SEQUENCE: 172
atggttgtgg agaaga                                                     16

<210> SEQ ID NO 173
<211> LENGTH: 18
<212> TYPE: DNA
<213> ORGANISM: Artificial Sequence
<220> FEATURE:
<223> OTHER INFORMATION: synthetic probe

<400> SEQUENCE: 173
tgagaactaa catcattt                                                   18

<210> SEQ ID NO 174
<211> LENGTH: 18
<212> TYPE: DNA
<213> ORGANISM: Artificial Sequence
<220> FEATURE:
<223> OTHER INFORMATION: synthetic probe

<400> SEQUENCE: 174
agaactaaca ccatttgt                                                   18

<210> SEQ ID NO 175
<211> LENGTH: 18
<212> TYPE: DNA
<213> ORGANISM: Artificial Sequence
<220> FEATURE:
<223> OTHER INFORMATION: synthetic probe

<400> SEQUENCE: 175
atattgacag ataaaaag                                                   18

<210> SEQ ID NO 176
<211> LENGTH: 18
<212> TYPE: DNA
<213> ORGANISM: Artificial Sequence
<220> FEATURE:
<223> OTHER INFORMATION: synthetic probe

<400> SEQUENCE: 176
atattgactg ataaaaag                                                   18

<210> SEQ ID NO 177
<211> LENGTH: 15
<212> TYPE: DNA
<213> ORGANISM: Artificial Sequence
<220> FEATURE:
<223> OTHER INFORMATION: synthetic probe

<400> SEQUENCE: 177
aacaacacag cgcag                                                      15

<210> SEQ ID NO 178
<211> LENGTH: 15
<212> TYPE: DNA
<213> ORGANISM: Artificial Sequence
<220> FEATURE:
<223> OTHER INFORMATION: synthetic probe

<400> SEQUENCE: 178
aacaacacaa cgcag                                                      15

```
<210> SEQ ID NO 179
<211> LENGTH: 19
<212> TYPE: DNA
<213> ORGANISM: Artificial Sequence
<220> FEATURE:
<223> OTHER INFORMATION: synthetic probe

<400> SEQUENCE: 179
agattgtacg atggattta                                              19

<210> SEQ ID NO 180
<211> LENGTH: 19
<212> TYPE: DNA
<213> ORGANISM: Artificial Sequence
<220> FEATURE:
<223> OTHER INFORMATION: synthetic probe

<400> SEQUENCE: 180
tagattgtac catggattt                                              19

<210> SEQ ID NO 181
<211> LENGTH: 16
<212> TYPE: DNA
<213> ORGANISM: Artificial Sequence
<220> FEATURE:
<223> OTHER INFORMATION: synthetic probe

<400> SEQUENCE: 181
agctccaaca tatgat                                                 16

<210> SEQ ID NO 182
<211> LENGTH: 16
<212> TYPE: DNA
<213> ORGANISM: Artificial Sequence
<220> FEATURE:
<223> OTHER INFORMATION: synthetic probe

<400> SEQUENCE: 182
ctccaaccta tgattg                                                 16

<210> SEQ ID NO 183
<211> LENGTH: 17
<212> TYPE: DNA
<213> ORGANISM: Artificial Sequence
<220> FEATURE:
<223> OTHER INFORMATION: synthetic probe

<400> SEQUENCE: 183
tatggattca aacaaga                                                17

<210> SEQ ID NO 184
<211> LENGTH: 17
<212> TYPE: DNA
<213> ORGANISM: Artificial Sequence
<220> FEATURE:
<223> OTHER INFORMATION: synthetic probe

<400> SEQUENCE: 184
aactatggat ccaaaca                                                17

<210> SEQ ID NO 185
<211> LENGTH: 15
<212> TYPE: DNA
<213> ORGANISM: Artificial Sequence
<220> FEATURE:
<223> OTHER INFORMATION: synthetic probe
```

```
<400> SEQUENCE: 185
agagaaggga aaatg                                                    15

<210> SEQ ID NO 186
<211> LENGTH: 15
<212> TYPE: DNA
<213> ORGANISM: Artificial Sequence
<220> FEATURE:
<223> OTHER INFORMATION: synthetic probe

<400> SEQUENCE: 186
cacagagaag gaaaa                                                    15

<210> SEQ ID NO 187
<211> LENGTH: 14
<212> TYPE: DNA
<213> ORGANISM: Artificial Sequence
<220> FEATURE:
<223> OTHER INFORMATION: synthetic probe

<400> SEQUENCE: 187
actacccgat cctt                                                     14

<210> SEQ ID NO 188
<211> LENGTH: 16
<212> TYPE: DNA
<213> ORGANISM: Artificial Sequence
<220> FEATURE:
<223> OTHER INFORMATION: synthetic probe

<400> SEQUENCE: 188
aactacctga tccttg                                                   16

<210> SEQ ID NO 189
<211> LENGTH: 17
<212> TYPE: DNA
<213> ORGANISM: Artificial Sequence
<220> FEATURE:
<223> OTHER INFORMATION: synthetic probe

<400> SEQUENCE: 189
aataacctgt atttttc                                                  17

<210> SEQ ID NO 190
<211> LENGTH: 19
<212> TYPE: DNA
<213> ORGANISM: Artificial Sequence
<220> FEATURE:
<223> OTHER INFORMATION: synthetic probe

<400> SEQUENCE: 190
cctcaaaata acctttatt                                                19

<210> SEQ ID NO 191
<211> LENGTH: 17
<212> TYPE: DNA
<213> ORGANISM: Artificial Sequence
<220> FEATURE:
<223> OTHER INFORMATION: synthetic probe

<400> SEQUENCE: 191
agtttgtttg gaatatt                                                  17
```

-continued

```
<210> SEQ ID NO 192
<211> LENGTH: 19
<212> TYPE: DNA
<213> ORGANISM: Artificial Sequence
<220> FEATURE:
<223> OTHER INFORMATION: synthetic probe

<400> SEQUENCE: 192
agtttgtttg gattattat                                               19

<210> SEQ ID NO 193
<211> LENGTH: 16
<212> TYPE: DNA
<213> ORGANISM: Artificial Sequence
<220> FEATURE:
<223> OTHER INFORMATION: synthetic probe

<400> SEQUENCE: 193
agccatcata aggaaa                                                  16

<210> SEQ ID NO 194
<211> LENGTH: 15
<212> TYPE: DNA
<213> ORGANISM: Artificial Sequence
<220> FEATURE:
<223> OTHER INFORMATION: synthetic probe

<400> SEQUENCE: 194
ccatcgtaag gaaac                                                   15

<210> SEQ ID NO 195
<211> LENGTH: 18
<212> TYPE: DNA
<213> ORGANISM: Artificial Sequence
<220> FEATURE:
<223> OTHER INFORMATION: synthetic probe

<400> SEQUENCE: 195
acaatttgta acatttttt                                               18

<210> SEQ ID NO 196
<211> LENGTH: 19
<212> TYPE: DNA
<213> ORGANISM: Artificial Sequence
<220> FEATURE:
<223> OTHER INFORMATION: synthetic probe

<400> SEQUENCE: 196
caatttgtaa cataattttt                                              19

<210> SEQ ID NO 197
<211> LENGTH: 14
<212> TYPE: DNA
<213> ORGANISM: Artificial Sequence
<220> FEATURE:
<223> OTHER INFORMATION: synthetic probe

<400> SEQUENCE: 197
tggtcccgcc ggta                                                    14

<210> SEQ ID NO 198
<211> LENGTH: 15
<212> TYPE: DNA
<213> ORGANISM: Artificial Sequence
<220> FEATURE:
<223> OTHER INFORMATION: synthetic probe
```

```
-continued

<400> SEQUENCE: 198
tggtcctgcc ggtaa                                                          15

<210> SEQ ID NO 199
<211> LENGTH: 15
<212> TYPE: DNA
<213> ORGANISM: Artificial Sequence
<220> FEATURE:
<223> OTHER INFORMATION: synthetic probe

<400> SEQUENCE: 199
caggagtcgt tatca                                                          15

<210> SEQ ID NO 200
<211> LENGTH: 15
<212> TYPE: DNA
<213> ORGANISM: Artificial Sequence
<220> FEATURE:
<223> OTHER INFORMATION: synthetic probe

<400> SEQUENCE: 200
caggagtcat tatca                                                          15
```

METHODS TO IDENTIFY SOYBEAN APHID RESISTANT QUANTITATIVE TRAIT LOCI IN SOYBEAN AND COMPOSITIONS THEREOF

CROSS-REFERENCE TO RELATED APPLICATIONS

This application claims the benefit under 35 U.S.C. §119(e) of U.S. Provisional Application No. 60/963,936 filed Aug. 8, 2007. The entirety of the application is hereby incorporated by reference.

INCORPORATION OF THE SEQUENCE LISTING

A sequence listing is contained in the file named "53776seqlisting.txt" which is 80,088 bytes (measured in MS-Windows) and was created on Aug. 7, 2008. This electronic sequence listing is electronically filed herewith and is incorporated herein by reference.

FIELD OF THE INVENTION

The present invention is in the field of plant breeding. More specifically, the invention includes methods and compositions for screening plants from the genus *Glycine* with markers associated with quantitative trait loci that are related to the aphid resistance in *Glycine* plants. The invention further includes methods and compositions of genomic regions for screening plants from the genus *Glycine* associated with aphid resistance.

BACKGROUND OF THE INVENTION

Soybean, *Glycine max* (L.) Merril, is a major economic crop worldwide and is a primary source of vegetable oil and protein (Sinclair and Backman, *Compendium of Soybean Diseases*, 3$^{rd}$ Ed. APS Press, St. Paul, Minn., p. 106. (1989). The growing demand for low cholesterol and high fiber diets has also increased soybean's importance as a health food.

Soybean varieties grown in the United States have a narrow genetic base. Six introductions, 'Mandarin,' 'Manchu,' 'Mandarin' (Ottawa), "Richland,' 'AK' (Harrow), and 'Mukden,' contributed nearly 70% of the germplasm represented in 136 cultivar releases. To date, modern day cultivars can be traced back from these six soybean strains from China. In a study conducted by Cox et al., *Crop Sci.* 25:529-532 (1988), the soybean germplasm is comprised of 90% adapted materials, 9% unadapted, and only 1% from exotic species. The genetic base of cultivated soybean could be widened through exotic species. In addition, exotic species may possess such key traits as disease, stress, and insect resistance.

Soybean aphid, *Aphis glycines* Matsumura, was identified as new insect pest of soybeans in 2001 and spread to over 21 states in the United States and 3 Canadian provinces by 2003 (Vennette et al. *Ann Entomol Soc Am* 97:217-226 (2004)). High yields are critical to a farmer's profit margin. Soybean aphid can cause over 50% yield losses (Wang et al., *Plant Protect* 20:12-13 (1994)). In addition to the decrease in yield, an increase in insecticide use can also decrease a farmer's profit margin. Over 7 million acres of soybean in the North Central U.S. were sprayed with insecticide to control soybean aphids in 2003; the estimated cost of the insecticide treatments was $84-$105 million in the North Central region alone in 2003 (Landis et al. NCR-125 Arthropod biological control: state reports for 2003; Li et al., *Mol Breeding* 19:25-34 (2007)).

Soybean aphids can directly damage the plant by removing significant amounts of water and nutrients causing the leaves to yellow and wilt. Additionally, aphids excrete honeydew, a sugar-rich sticky substance, on to the leaves and plants. Honeydew often leads to the development of sooty mold, which affects photosynthesis resulting significant yield losses (Gomez et al., *Environ Exp Bot* 55: 77-86 (2006)). Soybean aphids vector a number of viruses that can stunt plant growth, distorts leaves, cause mottling of leaves and stem, reduce pod number and cause discoloration in the seed. Viruses transmitted via soybean aphid include, Soybean mosaic virus, yellow mosaic virus, tobacco etch virus and tobacco vein mottling virus (Wang et al. *Plant Dis* 90: 920-926 (2006)).

Host plant resistance to insect are often quantitatively inherited traits and not major resistance gene. Stacking quantitative resistances is more durable than a major gene for resistance, but is difficult to identify and incorporate multiple quantitative resistances into a single soybean variety. Molecular markers associated with insect resistance offers breeders a more efficient method to work with quantitative traits and insect resistance. Aphid resistance genes and QTLs in soybean are known. Examples of which including Rag1 was identified in the soybean variety Dowling and mapped to linkage group M (U.S. patent application Ser. No. 11/158, 307). Additionally, quantitative trait loci associated with aphid resistance were identified in Plant Introduction (PI) 567598B and mapped linkage groups B2, D1b, J and K (PCT/US2006/019200).

There is a need in the art of plant breeding to identify additional quantitative trait loci associated with aphid resistance in soybean. Additionally, there is a need for rapid, cost-efficient method to assay the absence or presence of aphid resistance loci in soybean. The present invention provides a method for screening and selecting a soybean plant comprising a quantitative trait loci associated with aphid resistance using single nucleotide polymorphism (SNP) technology.

SUMMARY OF THE INVENTION

The present invention provides methods for producing aphid resistance in soybean plants. The present invention relates to methods to determine the presence or absence of quantitative trait loci conferring aphid resistance in soybean plants, including but not limited to exotic germplasm, populations, lines, elite lines, cultivars and varieties. The present invention is not limited to any one type of aphid resistant trait, such as antibiosis, antixenosis or repellency of aphids. More particularly, the invention relates to methods involving for identifying molecular markers associated with aphid resistance quantitative trait loci (QTL). The present invention relates to the use of molecular markers to screen and select for aphid resistance within soybean plants, including but not limited to exotic germplasm, populations, lines, elite lines, and varieties.

In a preferred embodiment, the present invention further provides quantitative trait loci associated with resistance to one or more of arthropods including but not limited to Coleoptera, examples of which including *Cerotoma* sp. such as bean leaf beetle (*Cerotoma trifurcata*), *Diabrotica* sp. such as spotted cucumber beetle (*Diabrotica undecimpunctata howardi*), *Epicauta* sp. such as blister beetle (*Epicauta pestifera*), *Popilli* sp. such as Japanese beetle (*Popillia japonica*), *Dectes* sp. such as soybean stem borer (*Dectes texanus texanus*), and *Colaspis* sp. such as grape *colaspis* (*Colaspis brunnea*), etc.; Orthoptera, examples of which including *Melanoplus* sp. such as red-legged grasshopper (*Melanoplus*

*femurrubrum*), and *Shistocerca* sp. such as American locust (*Shistocerca Americana*), etc.; Lepidoptera, examples of which including *Plathypen* sp. such as green cloverworm (*Plathypena scabra*), *Pseudoplusia* sp. such as soybean looper (*Pseudoplusia includens*), *Anticarsia* sp. such as velvetbean caterpillar (*Anticarsia gemmatalis*), *Epargyreus* sp. such as Silverspotted skipper (*Epargyreus clarus*), *Estigmene* sp. such as saltmarsh caterpillar (*Estigmene acrea*), *Spodoptera* sp. such as beet armyworm (*Spodoptera exigua*), *Heliothis* sp. such as Corn earworm (*Heliothis zea*), and *Matsumuraeses* sp. such as bean podworm (*Matsumuraeses phaseoli*); Hemiptera, examples of which including *Acrosternum* sp. such as green stink bugs (*Acrosternum hilare*), *Euschistus* sp. such as brown stink bug (*Euschistus servus*), *Nezara* sp. such as southern stinkbug (*Nezara viridula*); Homoptera, examples of which including *Spissistilus* sp. such as threecornered alfalfa hopper (*Spissistilus festinus*), and *Aphis* sp. such as soybean aphid (*Aphis glycines*); Thysanoptera, examples of which including *Sericothrips* sp. such as soybean thrips (*Sericothrips variabilis*).

In a preferred embodiment, the present invention further provides loci associated with resistance to nematodes, including, but not limited to *Heterodera* sp. such as soybean cyst nematode (*Heterodera glycines*), *Belonolaimus* sp. such as sting nematode (*Belonolaimus longicaudatus*), *Rotylenchulus* sp. such as reniform nematode (*Rotylenchulus reniformis*), *Meloidogyne* sp. such as southern root-knot nematode (*Meloidogyne incognita*), peanut root-knot nematode (*Meloidogyne arenaria*) and the Javanese root-knot nematode (*Meloidogyne javanica*).

The present invention relates to producing aphid resistant plants, populations, lines, elite lines, and varieties. More particularly, the present invention includes a method of introgressing an aphid resistant allele into a soybean plant comprising (A) crossing at least one first soybean plant comprising a nucleic acid sequence selected from the group consisting of SEQ ID NO: 81 through SEQ ID NO: 120 with at least one second soybean plant in order to form a segregating population, (B) screening the segregating population with one or more nucleic acid markers to determine if one or more soybean plants from the segregating population contains the nucleic acid sequence, and (C) selecting from the segregation population one or more soybean plants comprising a nucleic acid sequence selected from the group consisting of SEQ ID NO: 81 through SEQ ID NO: 120.

The present invention includes a method of introgressing an allele into a soybean plant comprising: (A) crossing at least one aphid resistant soybean plant with at least one aphid susceptible soybean plant in order to form a segregating population; (B) screening said segregating population with one or more nucleic acid markers to determine if one or more soybean plants from said segregating population contains an aphid resistant allele, wherein said aphid resistance allele is an allele selected from the group consisting of aphid resistance allele 1, aphid resistance allele 2, aphid resistance allele 3, aphid resistance allele 4, aphid resistance allele 5, aphid resistance allele 6, aphid resistance allele 7, aphid resistance allele 8, aphid resistance allele 9, aphid resistance allele 10, aphid resistance allele 11, aphid resistance allele 12, aphid resistance allele 13, aphid resistance allele 14, aphid resistance allele 15, aphid resistance allele 16, aphid resistance allele 17, aphid resistance allele 18, aphid resistance allele 19, aphid resistance allele 20, aphid resistance allele 21, aphid resistance allele 22, aphid resistance allele 23, aphid resistance allele 24, aphid resistance allele 25, aphid resistance allele 26, aphid resistance allele 27, aphid resistance allele 28, aphid resistance allele 29, aphid resistance allele 30, aphid resistance allele 31, aphid resistance allele 32, aphid resistance allele 33, aphid resistance allele 34, aphid resistance allele 35, aphid resistance allele 36, aphid resistance allele 37 and aphid resistance allele 38, aphid resistance allele 39, and aphid resistance allele 40.

The present invention includes an elite soybean plant comprising a nucleic acid sequence selected from the group consisting of SEQ ID NO: 81 through SEQ ID NO: 120.

BRIEF DESCRIPTION OF NUCLEIC ACID SEQUENCES

SEQ ID NO: 1 is a forward PCR primer for the amplification of SEQ ID NO: 81.

SEQ ID NO: 2 is a reverse PCR primer for the amplification of SEQ ID NO: 81.

SEQ ID NO: 3 is a forward PCR primer for the amplification of SEQ ID NO: 82.

SEQ ID NO: 4 is a reverse PCR primer for the amplification of SEQ ID NO: 82.

SEQ ID NO: 5 is a forward PCR primer for the amplification of SEQ ID NO: 83.

SEQ ID NO: 6 is a reverse PCR primer for the amplification of SEQ ID NO: 83.

SEQ ID NO: 7 is a forward PCR primer for the amplification of SEQ ID NO: 84.

SEQ ID NO: 8 is a reverse PCR primer for the amplification of SEQ ID NO: 84.

SEQ ID NO: 9 is a forward PCR primer for the amplification of SEQ ID NO: 85.

SEQ ID NO: 10 is a reverse PCR primer for the amplification of SEQ ID NO: 85.

SEQ ID NO: 11 is a forward PCR primer for the amplification of SEQ ID NO: 86.

SEQ ID NO: 12 is a reverse PCR primer for the amplification of SEQ ID NO: 86.

SEQ ID NO: 13 is a forward PCR primer for the amplification of SEQ ID NO: 87.

SEQ ID NO: 14 is a reverse PCR primer for the amplification of SEQ ID NO: 87.

SEQ ID NO: 15 is a forward PCR primer for the amplification of SEQ ID NO: 88.

SEQ ID NO: 16 is a reverse PCR primer for the amplification of SEQ ID NO: 88.

SEQ ID NO: 17 is a forward PCR primer for the amplification of SEQ ID NO: 89.

SEQ ID NO: 18 is a reverse PCR primer for the amplification of SEQ ID NO: 89.

SEQ ID NO: 19 is a forward PCR primer for the amplification of SEQ ID NO: 90.

SEQ ID NO: 20 is a reverse PCR primer for the amplification of SEQ ID NO: 90.

SEQ ID NO: 21 is a forward PCR primer for the amplification of SEQ ID NO: 91.

SEQ ID NO: 22 is a reverse PCR primer for the amplification of SEQ ID NO: 91.

SEQ ID NO: 23 is a forward PCR primer for the amplification of SEQ ID NO: 92.

SEQ ID NO: 24 is a reverse PCR primer for the amplification of SEQ ID NO: 92.

SEQ ID NO: 25 is a forward PCR primer for the amplification of SEQ ID NO: 93.

SEQ ID NO: 26 is a reverse PCR primer for the amplification of SEQ ID NO: 93.

SEQ ID NO: 27 is a forward PCR primer for the amplification of SEQ ID NO: 94.

SEQ ID NO: 28 is a reverse PCR primer for the amplification of SEQ ID NO: 94.
SEQ ID NO: 29 is a forward PCR primer for the amplification of SEQ ID NO: 95.
SEQ ID NO: 30 is a reverse PCR primer for the amplification of SEQ ID NO: 95.
SEQ ID NO: 31 is a forward PCR primer for the amplification of SEQ ID NO: 96.
SEQ ID NO: 32 is a reverse PCR primer for the amplification of SEQ ID NO: 96.
SEQ ID NO: 33 is a forward PCR primer for the amplification of SEQ ID NO: 97.
SEQ ID NO: 34 is a reverse PCR primer for the amplification of SEQ ID NO: 97.
SEQ ID NO: 35 is a forward PCR primer for the amplification of SEQ ID NO: 98.
SEQ ID NO: 36 is a reverse PCR primer for the amplification of SEQ ID NO: 98.
SEQ ID NO: 37 is a forward PCR primer for the amplification of SEQ ID NO: 99.
SEQ ID NO: 38 is a reverse PCR primer for the amplification of SEQ ID NO: 99.
SEQ ID NO: 39 is a forward PCR primer for the amplification of SEQ ID NO: 100.
SEQ ID NO: 40 is a reverse PCR primer for the amplification of SEQ ID NO: 100.
SEQ ID NO: 41 is a forward PCR primer for the amplification of SEQ ID NO: 101.
SEQ ID NO: 42 is a reverse PCR primer for the amplification of SEQ ID NO: 101.
SEQ ID NO: 43 is a forward PCR primer for the amplification of SEQ ID NO: 102.
SEQ ID NO: 44 is a reverse PCR primer for the amplification of SEQ ID NO: 102.
SEQ ID NO: 45 is a forward PCR primer for the amplification of SEQ ID NO: 103.
SEQ ID NO: 46 is a reverse PCR primer for the amplification of SEQ ID NO: 103.
SEQ ID NO: 47 is a forward PCR primer for the amplification of SEQ ID NO: 104.
SEQ ID NO: 48 is a reverse PCR primer for the amplification of SEQ ID NO: 104.
SEQ ID NO: 49 is a forward PCR primer for the amplification of SEQ ID NO: 105.
SEQ ID NO: 50 is a reverse PCR primer for the amplification of SEQ ID NO: 105.
SEQ ID NO: 51 is a forward PCR primer for the amplification of SEQ ID NO: 106.
SEQ ID NO: 52 is a reverse PCR primer for the amplification of SEQ ID NO: 106.
SEQ ID NO: 53 is a forward PCR primer for the amplification of SEQ ID NO: 107.
SEQ ID NO: 54 is a reverse PCR primer for the amplification of SEQ ID NO: 107.
SEQ ID NO: 55 is a forward PCR primer for the amplification of SEQ ID NO: 108.
SEQ ID NO: 56 is a reverse PCR primer for the amplification of SEQ ID NO: 108;
SEQ ID NO: 57 is a forward PCR primer for the amplification of SEQ ID NO: 109.
SEQ ID NO: 58 is a reverse PCR primer for the amplification of SEQ ID NO: 109.
SEQ ID NO: 59 is a forward PCR primer for the amplification of SEQ ID NO: 110.
SEQ ID NO: 60 is a reverse PCR primer for the amplification of SEQ ID NO: 110.
SEQ ID NO: 61 is a forward PCR primer for the amplification of SEQ ID NO: 111.
SEQ ID NO: 62 is a reverse PCR primer for the amplification of SEQ ID NO: 111
SEQ ID NO: 63 is a forward PCR primer for the amplification of SEQ ID NO: 112.
SEQ ID NO: 64 is a reverse PCR primer for the amplification of SEQ ID NO: 112.
SEQ ID NO: 65 is a forward PCR primer for the amplification of SEQ ID NO: 113.
SEQ ID NO: 66 is a reverse PCR primer for the amplification of SEQ ID NO: 113
SEQ ID NO: 67 is a forward PCR primer for the amplification of SEQ ID NO: 114.
SEQ ID NO: 68 is a reverse PCR primer for the amplification of SEQ ID NO: 114.
SEQ ID NO: 69 is a forward PCR primer for the amplification of SEQ ID NO: 115.
SEQ ID NO: 70 is a reverse PCR primer for the amplification of SEQ ID NO: 115.
SEQ ID NO: 71 is a forward PCR primer for the amplification of SEQ ID NO: 116.
SEQ ID NO: 72 is a reverse PCR primer for the amplification of SEQ ID NO: 116.
SEQ ID NO: 73 is a forward PCR primer for the amplification of SEQ ID NO: 117.
SEQ ID NO: 74 is a reverse PCR primer for the amplification of SEQ ID NO: 117.
SEQ ID NO: 75 is a forward PCR primer for the amplification of SEQ ID NO: 118.
SEQ ID NO: 76 is a reverse PCR primer for the amplification of SEQ ID NO: 118.
SEQ ID NO: 77 is a forward PCR primer for the amplification of SEQ ID NO: 119.
SEQ ID NO: 78 is a reverse PCR primer for the amplification of SEQ ID NO: 119.
SEQ ID NO: 79 is a forward PCR primer for the amplification of SEQ ID NO: 120.
SEQ ID NO: 80 is a reverse PCR primer for the amplification of SEQ ID NO: 120.
SEQ ID NO: 81 is a genomic sequence derived from *Glycine Max* corresponding to aphid resistance locus 1.
SEQ ID NO: 82 is a genomic sequence derived from *Glycine Max* corresponding to aphid resistance locus 1.
SEQ ID NO: 83 is a genomic sequence derived from *Glycine Max* corresponding to aphid resistance locus 1.
SEQ ID NO: 84 is a genomic sequence derived from *Glycine Max* corresponding to aphid resistance locus 1.
SEQ ID NO: 85 is a genomic sequence derived from *Glycine Max* corresponding to aphid resistance locus 2.
SEQ ID NO: 86 is a genomic sequence derived from *Glycine Max* corresponding to aphid resistance locus 3.
SEQ ID NO: 87 is a genomic sequence derived from *Glycine Max* corresponding to aphid resistance locus 4.
SEQ ID NO: 88 is a genomic sequence derived from *Glycine Max* corresponding to aphid resistance locus 5.
SEQ ID NO: 89 is a genomic sequence derived from *Glycine Max* corresponding to aphid resistance locus 6.
SEQ ID NO: 90 is a genomic sequence derived from *Glycine Max* corresponding to aphid resistance locus 7.
SEQ ID NO: 91 is a genomic sequence derived from *Glycine Max* corresponding to aphid resistance locus 8.
SEQ ID NO: 92 is a genomic sequence derived from *Glycine Max* corresponding to aphid resistance locus 8.
SEQ ID NO: 93 is a genomic sequence derived from *Glycine Max* corresponding to aphid resistance locus 9.

SEQ ID NO: 94 is a genomic sequence derived from *Glycine Max* corresponding to aphid resistance locus 10.
SEQ ID NO: 95 is a genomic sequence derived from *Glycine Max* corresponding to aphid resistance locus 11.
SEQ ID NO: 96 is a genomic sequence derived from *Glycine Max* corresponding to aphid resistance locus 12.
SEQ ID NO: 97 is a genomic sequence derived from *Glycine Max* corresponding to aphid resistance locus 13.
SEQ ID NO: 98 is a genomic sequence derived from *Glycine Max* corresponding to aphid resistance locus 14.
SEQ ID NO: 99 is a genomic sequence derived from *Glycine Max* corresponding to aphid resistance locus 15.
SEQ ID NO: 100 is a genomic sequence derived from *Glycine Max* corresponding to aphid resistance locus 16.
SEQ ID NO: 101 is a genomic sequence derived from *Glycine Max* corresponding to aphid resistance locus 16.
SEQ ID NO: 102 is a genomic sequence derived from *Glycine Max* corresponding to aphid resistance locus 16.
SEQ ID NO: 103 is a genomic sequence derived from *Glycine Max* corresponding to aphid resistance locus 17.
SEQ ID NO: 104 is a genomic sequence derived from *Glycine Max* corresponding to aphid resistance locus 18.
SEQ ID NO: 105 is a genomic sequence derived from *Glycine Max* corresponding to aphid resistance locus 19.
SEQ ID NO: 106 is a genomic sequence derived from *Glycine Max* corresponding to aphid resistance locus 20.
SEQ ID NO: 107 is a genomic sequence derived from *Glycine Max* corresponding to aphid resistance locus 21.
SEQ ID NO: 108 is a genomic sequence derived from *Glycine Max* corresponding to aphid resistance locus 21.
SEQ ID NO: 109 is a genomic sequence derived from *Glycine Max* corresponding to aphid resistance locus 22.
SEQ ID NO: 110 is a genomic sequence derived from *Glycine Max* corresponding to aphid resistance locus 23.
SEQ ID NO: 111 is a genomic sequence derived from *Glycine Max* corresponding to aphid resistance locus 23.
SEQ ID NO: 112 is a genomic sequence derived from *Glycine Max* corresponding to aphid resistance locus 24.
SEQ ID NO: 113 is a genomic sequence derived from *Glycine Max* corresponding to aphid resistance locus 25.
SEQ ID NO: 114 is a genomic sequence derived from *Glycine Max* corresponding to aphid resistance locus 26.
SEQ ID NO: 115 is a genomic sequence derived from *Glycine Max* corresponding to aphid resistance locus 26.
SEQ ID NO: 116 is a genomic sequence derived from *Glycine Max* corresponding to aphid resistance locus 27.
SEQ ID NO: 117 is a genomic sequence derived from *Glycine Max* corresponding to aphid resistance locus 28.
SEQ ID NO: 118 is a genomic sequence derived from *Glycine Max* corresponding to aphid resistance locus 28.
SEQ ID NO: 119 is a genomic sequence derived from *Glycine Max* corresponding to aphid resistance locus 28.
SEQ ID NO: 120 is a genomic sequence derived from *Glycine Max* corresponding to aphid resistance locus 28.
SEQ ID NO: 121 is a probe for the detection of the SNP of SEQ ID NO: 81.
SEQ ID NO: 122 is a probe for the detection of the SNP of SEQ ID NO: 81.
SEQ ID NO: 123 is a probe for the detection of the SNP of SEQ ID NO: 82.
SEQ ID NO: 124 is a probe for the detection of the SNP of SEQ ID NO: 82.
SEQ ID NO: 125 is a probe for the detection of the SNP of SEQ ID NO: 83.
SEQ ID NO: 126 is a probe for the detection of the SNP of SEQ ID NO: 83.
SEQ ID NO: 127 is a probe for the detection of the SNP of SEQ ID NO: 84.
SEQ ID NO: 128 is a probe for the detection of the SNP of SEQ ID NO: 84.
SEQ ID NO: 129 is a probe for the detection of the SNP of SEQ ID NO: 85.
SEQ ID NO: 130 is a probe for the detection of the SNP of SEQ ID NO: 85.
SEQ ID NO: 131 is a probe for the detection of the SNP of SEQ ID NO: 86.
SEQ ID NO: 132 is a probe for the detection of the SNP of SEQ ID NO: 86.
SEQ ID NO: 133 is a probe for the detection of the SNP of SEQ ID NO: 87.
SEQ ID NO: 134 is a probe for the detection of the SNP of SEQ ID NO: 87.
SEQ ID NO: 135 is a probe for the detection of the SNP of SEQ ID NO: 88.
SEQ ID NO: 136 is a probe for the detection of the SNP of SEQ ID NO: 88.
SEQ ID NO: 137 is a probe for the detection of the SNP of SEQ ID NO: 89.
SEQ ID NO: 138 is a probe for the detection of the SNP of SEQ ID NO: 89.
SEQ ID NO: 139 is a probe for the detection of the SNP of SEQ ID NO: 90.
SEQ ID NO: 140 is a probe for the detection of the SNP of SEQ ID NO: 90.
SEQ ID NO: 141 is a probe for the detection of the SNP of SEQ ID NO: 91.
SEQ ID NO: 142 is a probe for the detection of the SNP of SEQ ID NO: 91.
SEQ ID NO: 143 is a probe for the detection of the SNP of SEQ ID NO: 92.
SEQ ID NO: 144 is a probe for the detection of the SNP of SEQ ID NO: 92.
SEQ ID NO: 145 is a probe for the detection of the SNP of SEQ ID NO: 93.
SEQ ID NO: 146 is a probe for the detection of the SNP of SEQ ID NO: 93.
SEQ ID NO: 147 is a probe for the detection of the SNP of SEQ ID NO: 94.
SEQ ID NO: 148 is a probe for the detection of the SNP of SEQ ID NO: 94.
SEQ ID NO: 149 is a probe for the detection of the SNP of SEQ ID NO: 95.
SEQ ID NO: 150 is a probe for the detection of the SNP of SEQ ID NO: 95.
SEQ ID NO: 151 is a probe for the detection of the SNP of SEQ ID NO: 96.
SEQ ID NO: 152 is a probe for the detection of the SNP of SEQ ID NO: 96.
SEQ ID NO: 153 is a probe for the detection of the SNP of SEQ ID NO: 97.
SEQ ID NO: 154 is a probe for the detection of the SNP of SEQ ID NO: 97.
SEQ ID NO: 155 is a probe for the detection of the SNP of SEQ ID NO: 98.
SEQ ID NO: 156 is a probe for the detection of the SNP of SEQ ID NO: 98.
SEQ ID NO: 157 is a probe for the detection of the SNP of SEQ ID NO: 99.
SEQ ID NO: 158 is a probe for the detection of the SNP of SEQ ID NO: 99.
SEQ ID NO: 159 is a probe for the detection of the SNP of SEQ ID NO: 100.

SEQ ID NO: 160 is a probe for the detection of the SNP of SEQ ID NO: 100.
SEQ ID NO: 161 is a probe for the detection of the SNP of SEQ ID NO: 101.
SEQ ID NO: 162 is a probe for the detection of the SNP of SEQ ID NO: 101.
SEQ ID NO: 163 is a probe for the detection of the SNP of SEQ ID NO: 102.
SEQ ID NO: 164 is a probe for the detection of the SNP of SEQ ID NO: 102.
SEQ ID NO: 165 is a probe for the detection of the SNP of SEQ ID NO: 103.
SEQ ID NO: 166 is a probe for the detection of the SNP of SEQ ID NO: 103.
SEQ ID NO: 167 is a probe for the detection of the SNP of SEQ ID NO: 104.
SEQ ID NO: 168 is a probe for the detection of the SNP of SEQ ID NO: 104.
SEQ ID NO: 169 is a probe for the detection of the SNP of SEQ ID NO: 105.
SEQ ID NO: 170 is a probe for the detection of the SNP of SEQ ID NO: 105.
SEQ ID NO: 171 is a probe for the detection of the SNP of SEQ ID NO: 106.
SEQ ID NO: 172 is a probe for the detection of the SNP of SEQ ID NO: 106.
SEQ ID NO: 173 is a probe for the detection of the SNP of SEQ ID NO: 107.
SEQ ID NO: 174 is a probe for the detection of the SNP of SEQ ID NO: 107.
SEQ ID NO: 175 is a probe for the detection of the SNP of SEQ ID NO: 108.
SEQ ID NO: 176 is a probe for the detection of the SNP of SEQ ID NO: 108.
SEQ ID NO: 177 is a probe for the detection of the SNP of SEQ ID NO: 109.
SEQ ID NO: 178 is a probe for the detection of the SNP of SEQ ID NO: 109.
SEQ ID NO: 179 is a probe for the detection of the SNP of SEQ ID NO: 110.
SEQ ID NO: 180 is a probe for the detection of the SNP of SEQ ID NO: 110.
SEQ ID NO: 181 is a probe for the detection of the SNP of SEQ ID NO: 111.
SEQ ID NO: 182 is a probe for the detection of the SNP of SEQ ID NO: 111.
SEQ ID NO: 183 is a probe for the detection of the SNP of SEQ ID NO: 112.
SEQ ID NO: 184 is a probe for the detection of the SNP of SEQ ID NO: 112.
SEQ ID NO: 185 is a probe for the detection of the SNP of SEQ ID NO: 113.
SEQ ID NO: 186 is a probe for the detection of the SNP of SEQ ID NO: 113.
SEQ ID NO: 187 is a probe for the detection of the SNP of SEQ ID NO: 114.
SEQ ID NO: 188 is a probe for the detection of the SNP of SEQ ID NO: 114.
SEQ ID NO: 189 is a probe for the detection of the SNP of SEQ ID NO: 115.
SEQ ID NO: 190 is a probe for the detection of the SNP of SEQ ID NO: 115.
SEQ ID NO: 191 is a probe for the detection of the SNP of SEQ ID NO: 116.
SEQ ID NO: 192 is a probe for the detection of the SNP of SEQ ID NO: 116.
SEQ ID NO: 193 is a probe for the detection of the SNP of SEQ ID NO: 117.
SEQ ID NO: 194 is a probe for the detection of the SNP of SEQ ID NO: 117.
SEQ ID NO: 195 is a probe for the detection of the SNP of SEQ ID NO: 118.
SEQ ID NO: 196 is a probe for the detection of the SNP of SEQ ID NO: 118.
SEQ ID NO: 197 is a probe for the detection of the SNP of SEQ ID NO: 119.
SEQ ID NO: 198 is a probe for the detection of the SNP of SEQ ID NO: 119.
SEQ ID NO: 199 is a probe for the detection of the SNP of SEQ ID NO: 120.
SEQ ID NO: 200 is a probe for the detection of the SNP of SEQ ID NO: 120.
SEQ ID NO: 201 is a probe for the detection of the SNP of SEQ ID NO: 82.
SEQ ID NO: 202 is a probe for the detection of the SNP of SEQ ID NO: 82.
SEQ ID NO: 203 is a probe for the detection of the SNP of SEQ ID NO: 83.
SEQ ID NO: 204 is a probe for the detection of the SNP of SEQ ID NO: 83.
SEQ ID NO: 205 is a probe for the detection of the SNP of SEQ ID NO: 84.
SEQ ID NO: 206 is a probe for the detection of the SNP of SEQ ID NO: 84.
SEQ ID NO: 207 is a probe for the detection of the SNP of SEQ ID NO: 100.
SEQ ID NO: 208 is a probe for the detection of the SNP of SEQ ID NO: 100.
SEQ ID NO: 209 is a probe for the detection of the SNP of SEQ ID NO: 111.
SEQ ID NO: 210 is a probe for the detection of the SNP of SEQ ID NO: 111.
SEQ ID NO: 211 is a probe for the detection of the SNP of SEQ ID NO: 117.
SEQ ID NO: 212 is a probe for the detection of the SNP of SEQ ID NO: 117.
SEQ ID NO: 213 is a probe for the detection of the SNP of SEQ ID NO:119.
SEQ ID NO: 214 is a probe for the detection of the SNP of SEQ ID NO: 119.
SEQ ID NO: 215 is a probe for the detection of the SNP of SEQ ID NO: 120.
SEQ ID NO: 216 is a probe for the detection of the SNP of SEQ ID NO: 120.
SEQ ID NO: 217 is a probe for the detection of the SNP of SEQ ID NO: 82.
SEQ ID NO: 218 is a probe for the detection of the SNP of SEQ ID NO: 83.
SEQ ID NO: 219 is a probe for the detection of the SNP of SEQ ID NO: 84.
SEQ ID NO: 220 is a probe for the detection of the SNP of SEQ ID NO: 100.
SEQ ID NO: 221 is a probe for the detection of the SNP of SEQ ID NO: 111.
SEQ ID NO: 222 is a probe for the detection of the SNP of SEQ ID NO: 117.
SEQ ID NO: 223 is a probe for the detection of the SNP of SEQ ID NO: 119.
SEQ ID NO: 224 is a probe for the detection of the SNP of SEQ ID NO: 120.

DETAILED DESCRIPTION OF THE INVENTION

The present invention provides 28 aphid resistance loci that are located on linkage group A1, B1, B2, C1, D1a, D1b, E, F, G, H, I, and O in the soybean genome that are not previously associated with associated with aphid resistance (Table 1). The present invention also provides for quantitative trait loci (QTL) alleles capable of conferring resistance to soybean aphid. Alleles that are located at aphid resistance locus 1, aphid resistance locus 2, aphid resistance locus 3, aphid resistance locus 4, aphid resistance locus 5, aphid resistance locus 6, aphid resistance locus 7, aphid resistance locus 8, aphid resistance locus 9, aphid resistance locus 10, aphid resistance locus 11, aphid resistance locus 12, aphid resistance locus 13, aphid resistance locus 14, aphid resistance locus 15, aphid resistance locus 16, aphid resistance locus 17, aphid resistance locus 18, aphid resistance locus 19, aphid resistance locus 20, aphid resistance locus 21, aphid resistance locus 22, aphid resistance locus 23, aphid resistance locus 24, aphid resistance locus 25, aphid resistance locus 26, aphid resistance locus 27, and aphid resistance locus 28 are provided.

In the present invention, aphid resistance locus 1 is located on linkage group J. SNP markers used to monitor the introgression of aphid resistance locus 1 are SEQ ID NO: 81 through SEQ ID NO: 84. SNP marker DNA sequences associated with aphid resistance locus 1 (SEQ ID NO: 81 through SEQ ID NO: 84) can be amplified using the primers indicated as SEQ ID NO: 1 through SEQ ID NO: 8 and detected with probes indicated as SEQ ID NO: 121 through SEQ ID NO: 128, SEQ ID NO: 201 through SEQ ID NO: 206, and SEQ ID NO: 217 through SEQ ID NO: 219.

In the present invention, aphid resistance locus 2 is located on linkage group E. SNP marker used to monitor the introgression of aphid resistance locus 2 is SEQ ID NO: 85. SNP marker DNA sequences associated with aphid resistance locus 2 (SEQ ID NO: 85) can be amplified using the primers indicated as SEQ ID NO: 9 through SEQ ID NO: 10 and detected with probes indicated as SEQ ID NO: 129 through SEQ ID NO: 130.

In the present invention, aphid resistance locus 3 is located on linkage group E. SNP marker used to monitor the introgression of aphid resistance locus 3 is SEQ ID NO: 86. SNP marker DNA sequences associated with aphid resistance locus 3 (SEQ ID NO: 86) can be amplified using the primers indicated as SEQ ID NO: 11 through SEQ ID NO: 12 and detected with probes indicated as SEQ ID NO: 131 through SEQ ID NO: 132.

In the present invention, aphid resistance locus 4 is located on linkage group E. SNP marker used to monitor the introgression of aphid resistance locus 4 is SEQ ID NO: 87. SNP marker DNA sequences associated with aphid resistance locus 4 (SEQ ID NO: 87) can be amplified using the primers indicated as SEQ ID NO: 13 through SEQ ID NO: 14 and detected with probes indicated as SEQ ID NO: 133 through SEQ ID NO: 134.

In the present invention, aphid resistance locus 5 is located on linkage group B1. SNP marker used to monitor the introgression of aphid resistance locus 5 is SEQ ID NO: 88. SNP marker DNA sequences associated with aphid resistance locus 5 (SEQ ID NO: 88) can be amplified using the primers indicated as SEQ ID NO: 15 through SEQ ID NO: 16 and detected with probes indicated as SEQ ID NO: 135 through SEQ ID NO: 136.

In the present invention, aphid resistance locus 6 is located on linkage group N. SNP marker used to monitor the introgression of aphid resistance locus 6 is SEQ ID NO: 89. SNP marker DNA sequences associated with aphid resistance locus 6 (SEQ ID NO: 89) can be amplified using the primers indicated as SEQ ID NO: 17 through SEQ ID NO: 18 and detected with probes indicated as SEQ ID NO: 137 through SEQ ID NO: 138.

In the present invention, aphid resistance locus 7 is located on linkage group G. SNP marker used to monitor the introgression of aphid resistance locus 7 is SEQ ID NO: 90. SNP marker DNA sequences associated with aphid resistance locus 7 (SEQ ID NO: 90) can be amplified using the primers indicated as SEQ ID NO: 19 through SEQ ID NO: 20 and detected with probes indicated as SEQ ID NO: 139 through SEQ ID NO: 140.

In the present invention, aphid resistance locus 8 is located on linkage group N. SNP markers used to monitor the introgression of aphid resistance locus 8 are SEQ ID NO: 91 through SEQ ID NO 92. SNP marker DNA sequences associated with aphid resistance locus 8 (91 through SEQ ID NO 92) can be amplified using the primers indicated as SEQ ID NO: 21 through SEQ ID NO: 24 and detected with probes indicated as SEQ ID NO: 141 through SEQ ID NO: 144.

In the present invention, aphid resistance locus 9 is located on linkage group N. SNP marker used to monitor the introgression of aphid resistance locus 9 is SEQ ID NO: 93. SNP marker DNA sequences associated with aphid resistance locus 9 (SEQ ID NO: 93) can be amplified using the primers indicated as SEQ ID NO: 25 through SEQ ID NO: 26 and detected with probes indicated as SEQ ID NO: 145 through SEQ ID NO: 146.

In the present invention, aphid resistance locus 10 is located on linkage group A1. SNP marker used to monitor the introgression of aphid resistance locus 10 is SEQ ID NO: 94. SNP marker DNA sequences associated with aphid resistance locus 10 (SEQ ID NO: 94) can be amplified using the primers indicated as SEQ ID NO: 27 through SEQ ID NO: 28 and detected with probes indicated as SEQ ID NO: 147 through SEQ ID NO: 148.

In the present invention, aphid resistance locus 11 is located on linkage group A1. SNP marker used to monitor the introgression of aphid resistance locus 11 is SEQ ID NO: 95. SNP marker DNA sequences associated with aphid resistance locus 11 (SEQ ID NO: 95) can be amplified using the primers indicated as SEQ ID NO: 29 through SEQ ID NO: 30 and detected with probes indicated as SEQ ID NO: 149 through SEQ ID NO: 150.

In the present invention, aphid resistance locus 12 is located on linkage group DIa. SNP marker used to monitor the introgression of aphid resistance locus 12 is SEQ ID NO: 96. SNP marker DNA sequences associated with aphid resistance locus 12 (SEQ ID NO: 96) can be amplified using the primers indicated as SEQ ID NO: 31 through SEQ ID NO: 32 and detected with probes indicated as SEQ ID NO: 151 through SEQ ID NO: 152.

In the present invention, aphid resistance locus 13 is located on linkage group C2. SNP marker used to monitor the introgression of aphid resistance locus 13 is SEQ ID NO: 97. SNP marker DNA sequences associated with aphid resistance locus 13 (SEQ ID NO: 97) can be amplified using the primers indicated as SEQ iD NO: 33 through SEQ ID NO: 34 and detected with probes indicated as SEQ ID NO: 153 through SEQ ID NO: 154.

In the present invention, aphid resistance locus 14 is located on linkage group H. SNP marker used to monitor the introgression of aphid resistance locus 14 is SEQ ID NO: 98. SNP marker DNA sequences associated with aphid resistance locus 14 (SEQ ID NO: 98) can be amplified using the primers indicated as SEQ ID NO: 35 through SEQ ID NO: 36 and detected with probes indicated as SEQ ID NO: 155 through SEQ ID NO: 156.

In the present invention, aphid resistance locus 15 is located on linkage group H. SNP marker used to monitor the introgression of aphid resistance locus 15 is SEQ ID NO: 99.

SNP marker DNA sequences associated with aphid resistance locus 15 (SEQ ID NO: 99) can be amplified using the primers indicated as SEQ ID NO: 37 through SEQ ID NO: 38 and detected with probes indicated as SEQ ID NO: 157 through SEQ ID NO: 158.

In the present invention, aphid resistance locus 16 is located on linkage group D2. SNP marker used to monitor the introgression of aphid resistance locus 16 is SEQ ID NO: 100 through SEQ ID NO: 102. SNP marker DNA sequences associated with aphid resistance locus 16 (SEQ ID NO: 100 through SEQ ID NO: 102) can be amplified using the primers indicated as SEQ ID NO: 39 through SEQ ID NO: 44 and detected with probes indicated as SEQ ID NO: 159 through SEQ ID NO: 162, SEQ ID NO: 207 through SEQ ID NO: 208, and SEQ ID NO: 220.

In the present invention, aphid resistance locus 17 is located on linkage group F. SNP marker used to monitor the introgression of aphid resistance locus 17 is SEQ ID NO: 103. SNP marker DNA sequences associated with aphid resistance locus 17 (SEQ ID NO: 103) can be amplified using the primers indicated as SEQ ID NO: 45 through SEQ ID NO: 46 and detected with probes indicated as SEQ ID NO: 165 through SEQ ID NO: 166.

In the present invention, aphid resistance locus 18 is located on linkage group F. SNP marker used to monitor the introgression of aphid resistance locus 18 is SEQ ID NO: 104. SNP marker DNA sequences associated with aphid resistance locus 18 (SEQ ID NO: 104) can be amplified using the primers indicated as SEQ ID NO: 47 through SEQ ID NO: 48 and detected with probes indicated as SEQ ID NO: 167 through SEQ ID NO: 168.

In the present invention, aphid resistance locus 19 is located on linkage group I. SNP marker used to monitor the introgression of aphid resistance locus 19 is SEQ ID NO: 105. SNP marker DNA sequences associated with aphid resistance locus 19 (SEQ ID NO: 105) can be amplified using the primers indicated as SEQ ID NO: 49 through SEQ ID NO: 50 and detected with probes indicated as SEQ ID NO: 169 through SEQ ID NO: 170.

In the present invention, aphid resistance locus 20 is located on linkage group D1b. SNP marker used to monitor the introgression of aphid resistance locus 20 is SEQ ID NO: 106. SNP marker DNA sequences associated with aphid resistance locus 20 (SEQ ID NO: 106) can be amplified using the primers indicated as SEQ ID NO: 51 through SEQ ID NO: 52 and detected with probes indicated as SEQ ID NO: 171 through SEQ ID NO: 172.

In the present invention, aphid resistance locus 21 is located on linkage group D1b. SNP markers used to monitor the introgression of aphid resistance locus 21 are SEQ ID NO: 107 through SEQ ID NO. 108. SNP markers DNA sequences associated with aphid resistance locus 21 (SEQ ID NO: 107 through SEQ ID NO. 108) can be amplified using the primers indicated as SEQ ID NO: 53 through SEQ ID NO: 56 and detected with probes indicated as SEQ ID NO: 173 through SEQ ID NO: 176.

In the present invention, aphid resistance locus 22 is located on linkage group O, SNP marker used to monitor the introgression of aphid resistance locus 22 is SEQ ID NO: 109. SNP marker DNA sequences associated with aphid resistance locus 22 (SEQ ID NO: 109) can be amplified using the primers indicated as SEQ ID NO: 57 through SEQ ID NO: 58 and detected with probes indicated as SEQ ID NO: 177 through SEQ ID NO: 178.

In the present invention, aphid resistance locus 23 is located on linkage group O, SNP markers used to monitor the introgression of aphid resistance locus 23 are SEQ ID NO: 110 through SEQ ID NO: 111. SNP marker DNA sequences associated with aphid resistance locus 23 (SEQ ID NO: 110 through SEQ ID NO: 111) can be amplified using the primers indicated as SEQ ID NO: 59 through SEQ ID NO: 62 and detected with probes indicated as SEQ ID NO: 179 through SEQ ID NO: 182, SEQ ID NO: 209 through SEQ ID NO: 210, and SEQ ID NO: 221.

In the present invention, aphid resistance locus 24 is located on linkage group C1. SNP marker used to monitor the introgression of aphid resistance locus 24 is SEQ ID NO: 112. SNP marker DNA sequences associated with aphid resistance locus 24 (SEQ ID NO: 112) can be amplified using the primers indicated as SEQ ID NO: 63 through SEQ ID NO: 64 and detected with probes indicated as SEQ ID NO: 183 through SEQ ID NO: 184.

In the present invention, aphid resistance locus 25 is located on linkage group C1. SNP marker used to monitor the introgression of aphid resistance locus 25 is SEQ ID NO: 113. SNP marker DNA sequences associated with aphid resistance locus 25 (SEQ ID NO: 113) can be amplified using the primers indicated as SEQ ID NO: 65 through SEQ ID NO: 66 and detected with probes indicated as SEQ ID NO: 185 through SEQ ID NO: 186.

In the present invention, aphid resistance locus 26 is located on linkage group C1. SNP markers used to monitor the introgression of aphid resistance locus 26 are SEQ ID NO: 114 through SEQ ID NO: 115. SNP marker DNA sequences associated with aphid resistance locus 26 (SEQ ID NO: 114 through SEQ ID NO: 115) can be amplified using the primers indicated as SEQ ID NO: 67 through SEQ ID NO: 70 and detected with probes indicated as SEQ ID NO: 187 through SEQ ID NO: 190.

In the present invention, aphid resistance locus 27 is located on linkage group K. SNP marker used to monitor the introgression of aphid resistance locus 27 is SEQ ID NO: 116. SNP marker DNA sequences associated with aphid resistance locus 27 (SEQ ID NO: 116) can be amplified using the primers indicated as SEQ ID NO: 71 through SEQ ID NO: 72 and detected with probes indicated as SEQ ID NO: 191 through SEQ ID NO: 192.

In the present invention, aphid resistance locus 28 is located on linkage group B2. SNP markers used to monitor the introgression of aphid resistance locus 28 are SEQ ID NO: 117 through SEQ ID NO: 120. SNP marker DNA sequences associated with aphid resistance locus 28 (SEQ ID NO: 117 through SEQ ID NO: 120) can be amplified using the primers indicated as SEQ ID NO: 73 through SEQ ID NO: 80 and detected with probes indicated as SEQ ID NO: 193 through SEQ ID NO: 200, SEQ ID NO: 211-216, and SEQ ID NO: 222-223.

The present invention also provides a soybean plant comprising a nucleic acid sequence selected from the group consisting of SEQ ID NO: 81 through SEQ ID NO: 120 and complements thereof. In one aspect, the soybean plant comprises 1, 2, 3, 4, 5, 6, 7, 8, 9, 10, 11, 12, 13, 14, 15, 16, 17, 18, 19, 20, 21, 22, 23, 24, 25, 26, 27, or 28 nucleic acid sequences selected from the group consisting of SEQ ID NO: 81 through SEQ ID NO: 120, fragment thereof, and complements thereof.

The present invention also provides a soybean plant comprising 1, 2, 3, 4, 5, 6, 7, 8, 9, 10, 11, 12, 13, 15, 16, 17, 18, 19, 20, 21, 22, 23, 24, 25, 26, 27, or 28 aphid resistance loci where one or more alleles at one or more of their loci are selected from the group consisting of aphid resistance allele 1, aphid resistance allele 2, aphid resistance allele 3, aphid resistance allele 4, aphid resistance allele 5, aphid resistance allele 6, aphid resistance allele 7, aphid resistance allele 8, aphid resistance allele 9, aphid resistance allele 10, aphid resistance allele 11, aphid resistance allele 12, aphid resistance allele 13, aphid resistance allele 14, aphid resistance allele 15, aphid resistance allele 16, aphid resistance allele 17, aphid resistance allele 18, aphid resistance allele 19, aphid resistance allele 20, aphid resistance allele 21, aphid resistance allele 22, aphid resistance allele 23, aphid resistance allele 24, aphid resistance allele 25, aphid resistance allele 26, aphid resistance allele 27, aphid resistance allele 28, aphid resistance allele 29, aphid resistance allele 30, aphid resistance allele 31, aphid resistance allele 32, aphid resistance allele 33, aphid resistance allele 34, aphid resistance allele 35, aphid resistance allele 36, aphid resistance allele 37, aphid resistance allele 38, aphid resistance allele 39, and aphid resistance allele 40. Such alleles may be homozygous or heterozygous.

As used herein, aphid refers to any of various small, soft-bodied, plant-sucking insects of the Order Homoptera, further of the family Aphididae, wherein examples of Aphididae include but are not limited to the genus of *Acyrthosiphon, Allocotaphis, Amphorophora, Anoecia, Anuraphis, Aphidounguis, Aphidura, Aphis, Asiphonaphis, Astegopteryx, Aulacorthum, Betacallis, Betulaphis, Boernerina, Brachycaudus, Brachycorynella, Brevicoryne, Calaphis, Callipterinella, Callipterus, Cavariella, Cerataphis, Ceratovacuna, Chaetomyzus, Chaetosiphon, Chaitophorus, Chaitoregma, Chromaphis, Cinara, Clethrobius, Clydesmithia, Coloradoa, Cornaphis, Cryptomyzus, Crypturaphis, Doralis, Doraphis, Drepanaphis, Drepanosiphoniella, Drepanosiphum, Dysaphis, Eomacrosiphum, Epipemphigus, Ericolophium, Eriosoma, Essigella, Euceraphis, Eulachnus, Eumyzus, Eutrichosiphum, Fimbriaphis, Fullawaya, Geopemphigus, Glyphina, Gootiella, Greenidea, Grylloprociphilus, Hamamelistes, Hannabura, Hornaphis, Hyadaphis, Hyalomyzus, Hyalopterus, Hyperomyza, Hyperomyzus, Hysteroneura, Illinoia, Indiaphis, Indomasonaphis, Kakimia, Lachnus, Laingia, Lambersaphis, Latgerina, Longicaudus, Longistigma, Macromyzus, Macrosiphoniella*, etc. while even further any one or more of the following genus species of Aphididae, examples of which including soybean aphid *Aphis glycines*, Bean aphid *Aphis fabae*, Cotton aphid *Aphis gossypii*, Rose aphid *Macrosiphun rosae*, green peach aphid *Myzus persicae*, corn leaf aphid *Rhopalosiphum maidis*, spotted alfalfa aphid *Therioaphis maculata*, wooly apple aphid *Eriosoma lanigerum* and the like.

As used herein, soybean aphid, *Aphis glycines*, and *Aphis glycines* Matasamura refers to an aphid that feeds on soybean. However, any aphid that is found on and feeds on a soybean plant, such as the bean aphis *Aphis fabae* is a target for aphid resistance in soybean and is within the scope of the invention. A soybean plant of the present invention can be resistant to one or more aphids infesting a soybean plant. In one aspect, the present invention provides plants resistant to aphids as well as methods and compositions for screening soybean plants for resistance or, susceptibility to aphids, caused by the genus *Aphis*. In a preferred aspect, the present invention provides methods and compositions for screening soybean plants for resistance or susceptibility to *Aphis glycines*.

In an aspect, the plant is selected from the genus *Glycine*. *Glycine* plants, including but not limited to exotic germplasm, populations, lines, elite lines, cultivars and varieties.

As uses herein, soybean plant refers to a plant of the family Fabaceae, herein uses in the broadest sense and includes but is not limited to any species of soybean, examples of which including a *Glycine* species. A soybean plant may be a *Glycine arenaria, Glycine argyrea, Glycine canescens, Glycine clandestine, Glycine curvata, Glycine cyrtoloba, Glycinefalcate, Glycine latifolia, Glycine latrobeana, Glycine max, Glycine microphylla, Glycine pescadrensis, Glycine pindanica, Glycine rubiginosa, Glycine soja, Glycine* sp., *Glycine stenophita, Glycine tabacina*, and *Glycine tomentella*.

Plants of the present invention can be a soybean plant that is very resistant, resistant, substantially resistant, mid-resistant, comparatively resistant, partially resistant, mid-susceptible, or susceptible.

As used herein, the term resistant, resistance and host plant resistance refers the ability of a host plant to prevent or reduce infestation and damage of a pest from the group comprising insects, nematodes, pathogens, fungi, viruses, and diseases.

As used herein, the term antixenosis or non-preference resistance refers to the ability of a plant to ability to repel insects, causing a reduction in egg laying and feeding.

As used herein, the term antibiosis refers the ability of a plant to reduce survival, growth, or reproduction of insects that feed on it.

As used herein, the term tolerance refers to the ability of host plant to produce a larger yield of good quality than other plants when being fed upon by similar numbers of insects.

In a preferred aspect, the present invention provides a soybean plant to be assayed for resistance or susceptibility to aphids by any method to determine whether a soybean plant is very resistant, resistant, moderately resistant, moderately susceptible, or susceptible.

In this aspect, a plant is assayed for aphid resistance or susceptibility by visually estimating the number of aphids on a plant (Mensah et al. *Crop Sci* 25:2228-2233 (2005)).

As used herein, aphid resistance refers to preventing or inhibiting the ability of aphids to cause damage, such as reducing feeding, delaying growth and developing, reducing fecundity and the like, to a host plant.

In another aspect, the soybean plant can show a comparative resistance compared to a non-resistant control soybean plant. In this aspect, a control soybean plant will preferably be genetically similar except for the aphid resistant allele or alleles in question. Such plants can be grown under similar conditions with equivalent or near equivalent exposure to the pest. In this aspect, the resistant plant or plants has significantly fewer aphids per plant or damage per plant on resistant plants compared to known susceptible plants, and equivalent number of aphids or damage per plant compared to known resistant plants As used herein, the terms quantitative trait loci and QTL refer to a genomic region affecting the phenotypic variation in continuously varying traits like yield or resistance. A QTL can comprise multiple genes or other genetic factors even within a contiguous genomic region or linkage group.

As used herein, the terms single nucleotide polymorphism and SNP refer to a single base difference between two DNA sequences.

As used herein, the term oligonucleotide refers to a molecule comprised of two or more deoxyribonucleotides or ribonucleotides.

As used herein, the term primer refers to an oligonucleotide complementary to a given nucleotide sequence and that is needed to initiate replication by a polymerase.

As used herein, the term probe refers to an oligonucleotide that is capable of hybridizing to another oligonucleotide of interest. A probe may be a single-stranded or double stranded oligonucleotide. Probes are useful for detection, identification or isolation of particular nucleotide sequence.

As used herein, the term gene refers to a nucleic acid sequence that comprises introns, untranslated regions and control regions, and coding sequences necessary for the production RNA, a polypeptide or a pre-cursor of a polypeptide.

As used herein, the term marker, DNA marker, and genetic marker refers to a trait, including genetic traits such as DNA sequences loci alleles chromosome features isozyme, and morphological traits that can be used as detect the presence or location of a gene or trait in an individual or in a population.

As used herein, a diagnostic marker refers to a genetic marker than can detect or identify a trait, examples of which including aphid resistance, rust resistance and yield.

A resistance QTL of the present invention may be introduced into an elite soybean line. Herein, "line" refers to a group of individual plants from the similar parentage with similar traits. An "elite line" is any line that has resulted from breeding and selection for superior agronomic performance. Additionally, an elite line is sufficiently homogenous and homozygous to be used for commercial production. Elite lines may be used in the further breeding efforts to develop new elite lines.

An aphid resistance QTL of the present invention may also be introduced into an soybean line comprising one or more transgenes conferring transgenic plant that contains one or more genes for herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistant, increased digestibility, industrial enzymes, pharmaceutical proteins, peptides and small molecules, improved processing traits, improved flavor, nitrogen fixation, hybrid seed production, reduced allergenicity, biopolymers, and biofuels among others. These agronomic traits can be provided by the methods of plant biotechnology as transgenes in soybean.

An aphid resistant QTL allele or alleles can be introduced from any plant that contains that allele (donor) to any recipient soybean plant. In one aspect, the recipient soybean plant can contain additional aphid resistant loci. In another aspect, the recipient soybean plant can contain a transgene. In another aspect, while maintaining the introduced QTL, the genetic contribution of the plant providing the aphid resistant QTL can be reduced by back-crossing or other suitable approaches. In one aspect, the nuclear genetic material derived from the donor material in the soybean plant can be less than or about 50%, less than or about 25%, less than or about 13%, less than or about 5%, 3%, 2% or 1%, but that genetic material contains the aphid resistant locus or loci of interest.

Plants containing one or more aphid resistant loci described can be donor plants. Aphid plants containing resistant loci can be, examples of which including screened for by using a nucleic acid molecule capable of detecting a marker polymorphism associated with resistance. In one aspect, a donor plant is PI 594427C. In a preferred aspect, a donor plant is the source for aphid resistance loci 1, 2, 4, 6, 7, 8, 9, 11, 13, 15, 16, 17, 18, 19, 20, 21, 22, 23, 27, and 28. In another aspect, a donor plant is soybean variety MV0031. In another preferred aspect, a donor plant is the source for aphid resistance loci 2, 5, 8, 10, 25, and 26. In another aspect, a donor plant is soybean variety CNS (PI 548445). In another preferred aspect, a donor plant is the source for aphid resistance loci 3, 12, 14, and 24. A donor plant can be a susceptible line. In one aspect, a donor plant can also be a recipient soybean plant.

As used herein, a maturity group refers to an industry division of groups of varieties based range in latitude which the plant is best adapted and most productive. Soybean varieties are classified into 13 recognized maturity groups with the designations ranging from maturity groups 000, 00, 0, and I through X, wherein 000 represents the earliest maturing variety and X represents the latest maturing variety. Soybean plants in maturity groups 000 to IV have indeterminate plant habit, while soybean plants in maturity groups V through X have determinate plant habit. Herein, determinate growth habit refers to a cease vegetative growth after the main stem terminates in a cluster of mature pods. Herein, indeterminate growth habit refers to the development of leaves and flowers simultaneously throughout a portion of their reproductive period, with one to three pods at the terminal apex. Early maturity varieties (000 to IV) are adapted to northern latitudes with longer day lengths with the maturity designation increasing in southern latitudes with shorter day lengths Herein, relative maturity refers to a soybean plant maturity group subdividing a maturity group into tenths, for example III.5. Relative maturity provided a more exact maturity. The number following the decimal point refers to the relative earliness or lateness with a maturity group, examples of which including IV.2 is an early group IV variety and IV.9 is a late group IV.

It is further understood that a soybean plant of the present invention may exhibit the characteristics of any relative maturity group. In an aspect, the relative maturity group is selected from the group consisting of 000.1-000.9, 00.1-00.9, 0.1-0.9, I.1-I.9, II.1-II.9, III.1-III.9, IV.1-IV.9, V.1-V.9, VI.1-VI.9, VII.1-VII.9, VIII.1-VIII.9, IX.1-IX.9, and X.1-X.9. The pollen for selected soybean plant can be cryopreserved and used in crosses with soybean lines from other maturity groups to introgress an aphid resistance locus in a line that would not normally be available for crossing in nature. Pollen cryopreservation techniques are well known in the art (Tyagi and Hymowitz, *Cryo letters* 24: 119-124 (2003), Liang et al. *Acta Botanica Sinica* 35: 733-738 (1993)).

The aphid resistance effect of the QTL can vary based on parental genotype and on the environmental factors in which the aphid resistance is measured. It is within the skill of those in the art of plant breeding and without undue experimentation to use methods described herein to select from populations of plants or from a collection of parental genotypes those that when containing an aphid resistance locus result in enhanced aphid resistance relative to the parental genotype. Herein, an infestation can be caused by insects, fungi, virus, bacterium or invertebrate animal.

A number of molecular genetic maps of *Glycine* have been reported (Mansur et al., *Crop Sci.* 36: 1327-1336 (1996), Shoemaker et al., *Genetics* 144: 329-338 (1996); Shoemaker et al., *Crop Science* 32: 1091-1098 (1992), Shoemaker et al., *Crop Science* 35: 436-446 (1995); Tinley and Rafalski, *J. Cell Biochem. Suppl.* 14E: 291 (1990),); Cregan et al., *Crop Science* 39:1464-1490 (1999). *Glycine max, Glycine soja* and *Glycine max* x. *Glycine soja* share linkage groups (Shoemaker et al., *Genetics* 144: 329-338 (1996). A linkage group (LG) is a set of genes that tend to be inherited together from generation to generation. As used herein, reference to the linkage groups (LG), J, E, B1, N, A1, D1a_Q, H, D1, F, I D1b+W, O C1 and B2 of *Glycine max* refers to the linkage group that corresponds to linkage groups, J, E, B1, N, A1, D1a_Q, H, D1, F, I D1b+W, O C1 and B2 from the genetic map of *Glycine max* (Mansur et al., *Crop Science* 36: 1327-1336 (1996); Cregan et al., *Crop Science* 39:1464-1490 (1999), and Soybase, Agricultural Research Service, United States Department of Agriculture).

An allele of a QTL can, of course, comprise multiple genes or other genetic factors even within a contiguous genomic region or linkage group, such as a haplotype. A linkage group is a group loci carried on the same chromosome. A haplotype is set of genetic markers associated with closely linked segments of DNA on one chromosome and tend to be inherited as a unit. As used herein, an allele of a resistance locus can therefore encompass more than one gene or other genetic factor wherein each individual gene or genetic component is also capable of exhibiting allelic variation and wherein each gene or genetic factor is also capable of eliciting a phenotypic effect on the quantitative trait in question. In an aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present invention can denote a haplotype within a haplotype window wherein a phenotype can be pest resistance. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker. As used herein, an allele is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus. Plants of the present invention may be homozygous or heterozygous at any particular aphid resistance locus or for a particular polymorphic marker.

The present invention also provides for parts of the plants of the present invention. Plant parts, without limitation, include seed, endosperm, ovule and pollen. In a particularly preferred aspect of the present invention, the plant part is a seed.

Plants or parts thereof of the present invention may be grown in culture and regenerated. Methods for the regeneration of *Glycine max* plants from various tissue types and methods for the tissue culture of *Glycine max* are known in the art (See, examples of which including Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use as the starting material a variety of tissue or cell types. With *Glycine max* in particular, regeneration processes have been developed that begin with certain differentiated tissue types such as meristems, Cartha et al., *Can. J. Bot.* 59:1671-1679 (1981), hypocotyl sections, Cameya et al., *Plant Science Letters* 21: 289-294 (1981), and stem node segments, Saka et al., *Plant Science Letters*, 19: 193-201 (1980); Cheng et al., *Plant Science Letters*, 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986).

The present invention also provides an aphid resistant soybean plant selected for by screening for aphid resistance or susceptibility in the soybean plant, the selection comprising interrogating genomic nucleic acids for the presence of a marker molecule that is genetically linked to an allele of a QTL associated with aphid resistance in the soybean plant, where the allele of a QTL is also located on a linkage group associated with aphid resistant soybean.

The present invention includes a method of introgressing an aphid resistant allele into a soybean plant comprising (A) crossing at least one first soybean plant comprising a nucleic acid sequence selected from the group consisting of SEQ ID NO: 81 through SEQ ID NO: 120 with at least one second soybean plant in order to form a segregating population, (B) screening the segregating population with one or more nucleic acid markers to determine if one or more soybean plants from the segregating population contains the nucleic acid sequence, and (C) selecting from the segregation population one or more soybean plants comprising a nucleic acid sequence selected from the group consisting of SEQ ID NO: 81 through SEQ ID NO: 120.

The present invention includes a method of introgressing an allele into a soybean plant comprising: (A) crossing at least one aphid resistant soybean plant with at least one aphid sensitive soybean plant in order to form a segregating population; (B) screening said segregating population with one or more nucleic acid markers to determine if one or more soybean plants from said segregating population contains an aphid resistant allele, wherein said aphid resistance allele is an allele selected from the group consisting of aphid resistance allele 1, aphid resistance allele 2, aphid resistance allele 3, aphid resistance allele 4, aphid resistance allele 5, aphid resistance allele 6, aphid resistance allele 7, aphid resistance allele 8, aphid resistance allele 9, aphid resistance allele 10, aphid resistance allele 11, aphid resistance allele 12, aphid resistance allele 13, aphid resistance allele 14, aphid resistance allele 15, aphid resistance allele 16, aphid resistance allele 17, aphid resistance allele 18, aphid resistance allele 19, aphid resistance allele 20, aphid resistance allele 21, aphid resistance allele 22, aphid resistance allele 23, aphid resistance allele 24, aphid resistance allele 25, aphid resistance allele 26, aphid resistance allele 27, aphid resistance allele 28, aphid resistance allele 29, aphid resistance allele 30, aphid resistance allele 31, aphid resistance allele 32, aphid resistance allele 33, aphid resistance allele 34, aphid resistance allele 35, aphid resistance allele 36, aphid resistance allele 37, aphid resistance allele 38, aphid resistance allele 39, and aphid resistance allele 40.

The present invention includes nucleic acid molecules. Such molecules include those nucleic acid molecules capable of detecting a polymorphism genetically or physically linked to aphid resistance loci. Such molecules can be referred to as markers. Additional markers can be obtained that are linked to aphid resistance locus 1, aphid resistance locus 2, aphid resistance locus 3, aphid resistance locus 4, aphid resistance locus 5, aphid resistance locus 6, aphid resistance locus 7, aphid resistance locus 8, aphid resistance locus 9, aphid resistance locus 10, aphid resistance locus 11, aphid resistance locus 12, aphid resistance locus 13, aphid resistance locus 14, aphid resistance locus 15, aphid resistance locus 16, aphid resistance locus 17, aphid resistance locus 18, aphid resistance locus 19, aphid resistance locus 20, aphid resistance locus 21, aphid resistance locus 22, aphid resistance locus 23, aphid resistance locus 24, aphid resistance locus 25, aphid resistance locus 26, aphid resistance locus 27, and aphid resistance locus 28 by available techniques. In one aspect, the nucleic acid molecule is capable of detecting the presence or absence of a marker located less than 50, 40, 30, 20, 10, 5, 2, or 1 centimorgans from an aphid resistance loci. In another aspect, a marker exhibits a LOD score of 2 or greater, 3 or greater, or 4 or greater with aphid resistance, measuring using MapManager or QGene Version 3 and default parameters. In another aspect, the nucleic acid molecule is capable of detecting a marker in a locus selected from the group aphid resistance locus 1, aphid resistance locus 2, aphid resistance locus 3, aphid resistance locus 4, aphid resistance locus 5, aphid resistance locus 6, aphid resistance locus 7, aphid resistance locus 8, aphid resistance locus 9, aphid resistance locus 10, aphid resistance locus 11, aphid resistance locus 12, aphid resistance locus 13, aphid resistance locus 14, aphid resistance locus 15, aphid resistance locus 16, aphid resistance locus 17, aphid resistance locus 18, aphid resistance locus 19, aphid resistance locus 20, aphid resistance locus 21, aphid resistance locus 22, aphid resistance locus 23, aphid resistance locus 24, aphid resistance locus 25, aphid resistance locus 26, aphid resistance locus 27, and aphid resistance locus 28. In a further aspect, a nucleic acid molecule is selected from the group consisting of SEQ ID NO: 81 through SEQ ID NO: 120, fragments thereof, complements thereof, and nucleic acid molecules capable of specifically hybridizing to one or more of these nucleic acid molecules.

In a preferred aspect, a nucleic acid molecule of the present invention includes those that will specifically hybridize to one or more of the nucleic acid molecules set forth in SEQ ID NO: 81 through SEQ ID NO: 120 or complements thereof or fragments of either under moderately stringent conditions, for example at about 2.0×SSC and about 65° C. In a particularly preferred aspect, a nucleic acid of the present invention will specifically hybridize to one or more of the nucleic acid molecules set forth in SEQ ID NO: 81 through SEQ ID NO: 120 or complements or fragments of either under high stringency conditions. In one aspect of the present invention, a preferred marker nucleic acid molecule of the present invention has the nucleic acid sequence set forth in SEQ ID NO: 81 through SEQ ID NO: 120 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO: 81 through SEQ ID NO: 120 or complement thereof or fragments of either. In a further aspect of the present invention, a preferred marker nucleic acid molecule of the present invention shares between 95% and 100% sequence identity with the sequence set forth in SEQ ID NO: 81 through SEQ ID NO: 120 or complement thereof or fragments of either. In a more preferred aspect of the present invention, a preferred marker nucleic acid molecule of the present invention shares between 98% and 100% sequence identity with the nucleic acid sequence set forth in SEQ ID NO: 81 through SEQ ID NO: 120 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, molecules are exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual*, 2nd Edition, Cold Spring Harbor Press, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 *Nucl. Acids Res.* 12: 203-213; and Wetmur et al. 1968 *J. Mol. Biol.* 31:349-370. Appropriate stringency conditions that promote DNA hybridization are, examples of which including 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. Examples of which including the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Examples of which including hybridization using DNA or RNA probes or primers can be performed at 65° C. in 6×SSC, 0.5% SDS, 5×Denhardt's, 100 µg/mL nonspecific DNA (e.g., sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule can be any sized fragment and illustrative fragments include fragments of nucleic acid sequences set forth in SEQ ID NO: 81 through SEQ ID NO: 120 and complements thereof. In one aspect, a fragment can be between 15 and 25, 15 and 30, 15 and 40, 15 and 50, 15 and 100, 20 and 25, 20 and 30, 20 and 40, 20 and 50, 20 and 100, 25 and 30, 25 and 40, 25 and 50, 25 and 100, 30 and 40, 30 and 50, and 30 and 100. In another aspect, the fragment can be greater than 10, 15, 20, 25, 30, 35, 40, 50, 100, or 250 nucleotides.

Additional genetic markers can be used to select plants with an allele of a QTL associated with aphid resistance of soybean of the present invention. Examples of public marker databases include, for example: Soybase, Agricultural Research Service, United States Department of Agriculture.

A genetic marker is a DNA sequence that has a known location on a chromosome and associated with a particular trait or gene. Genetic markers associated with aphid resistance can be used to determine whether an individual plant is resistant to aphids.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations wherein individuals are predominantly homozygous and loci are predominantly dimorphic, dominant and codominant markers can be equally valuable. As populations become more heterozygous and multiallelic, codominant markers often become more informative of the genotype than dominant markers.

Markers, such as single sequence repeat markers (SSR), AFLP markers, RFLP markers, RAPD markers, phenotypic markers, SNPs, isozyme markers, microarray transcription profiles that are genetically linked to or correlated with alleles of a QTL of the present invention can be utilized (Walton, 1993; Burow et al. 1988). Methods to isolate such markers are known in the art.

The detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor *Symp. Quant. Biol.* 51:263-273; European Patent No. 50,424; European Patent No. 84,796; European Patent No. 258,017; European Patent No. 237,362; European Patent No. 201,184; U.S. Pat. Nos. 4,683,202; 4,582,788; and 4,683,194), using primer pairs that are capable of hybridizing to the proximal sequences that define a polymorphism in its double-stranded form.

For the purpose of QTL mapping, the markers included should be diagnostic of origin in order for inferences to be made about subsequent populations. SNP markers are ideal for mapping because the likelihood that a particular SNP allele is derived from independent origins in the extant populations of a particular species is very low. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al. (Lander et al. 1989 *Genetics,* 121:185-199), and the interval mapping, based on maximum likelihood methods described therein, and implemented in the software package MAPMAKER/QTL (Lincoln and Lander, *Mapping Genes Controlling Quantitative Traits Using MAPMAKER/QTL*, Whitehead Institute for Biomedical Research, Massachusetts, (1990). Additional software includes Qgene, Version 3, Department of Plant Breeding and Biometry, 266 Emerson Hall, Cornell University, Ithaca, N.Y.). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$(MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al. (1989), and further described by Arús and Moreno-González, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al. 1995 *Genetics,* 139:1421-1428). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al. 1994 *Genetics,* 136:1447-1455) and Zeng (Zeng 1994 *Genetics* 136: 1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al. 1995 *Theor. Appl. Genet.* 91:33-3).

Selection of appropriate mapping populations is important to map construction. The choice of an appropriate mapping population depends on the type of marker systems employed (Tanksley et al., *Molecular mapping in plant chromosomes. chromosome structure and function: Impact of new concepts* J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted× adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. pest resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequilibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al. 1992 *Proc. Natl. Acad. Sci.* (USA) 89:1477-1481). However, as the distance between markers becomes larger (i.e., loci become more independent), the information in RIL populations decreases dramatically.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created comprising of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al. 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant-analysis (BSA) is a method developed for the rapid identification of linkage between markers and traits of interest (Michelmore et al. 1991 *Proc. Natl. Acad. Sci.* (U.S.A.) 88:9828-9832). In BSA, two bulked DNA samples are drawn from a segregating population originating from a single cross. These bulks contain individuals that are identical for a particular trait (resistant or susceptible to particular pests) or genomic region but arbitrary at unlinked regions (i.e. heterozygous). Regions unlinked to the target region will not differ between the bulked samples of many individuals in BSA.

An alternative to traditional QTL mapping involves achieving higher resolution by mapping haplotypes, versus individual markers (Fan et al. 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well with in the skill of the ordinary practitioner of the art.

Plants of the present invention can be part of or generated from a breeding program. The choice of breeding method depends on the mode of plant reproduction, the heritability of the trait(s) being improved, and the type of cultivar used commercially (e.g., $F_1$ hybrid cultivar, pureline cultivar, etc). A cultivar is a race or variety of a plant species that has been created or selected intentionally and maintained through cultivation.

Selected, non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial and non-commercial cultivars can be utilized in a breeding program. Factors such as, examples of which including emergence vigor, vegetative vigor, stress tolerance, disease resistance, branching, flowering, seed set, seed size, seed density, standability, and threshability etc. will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In a preferred aspect, a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease and insect-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

The development of new elite soybean hybrids requires the development and selection of elite inbred lines, the crossing of these lines and selection of superior hybrid crosses. The hybrid seed can be produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (e.g., cultivar) and, in addition, the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books (Allard, "Principles of Plant Breeding," John Wiley & Sons, NY, U. of CA, Davis, Calif., 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: *Soybeans: Improvement, Production and Uses,* 2nd Edition, *Manograph.,* 16:249, 1987; Fehr, "Principles of variety development," *Theory and Technique,* (Vol. 1) and *Crop Species Soybean* (Vol. 2), Iowa State Univ., Macmillan Pub. Co., NY, 360-376, 1987).

It is further understood, that the present invention provides bacterial, viral, microbial, insect, mammalian and plant cells comprising the nucleic acid molecules of the present invention.

As used herein, a "nucleic acid molecule," be it a naturally occurring molecule or otherwise may be "substantially purified", if desired, referring to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

The agents of the present invention may be labeled with reagents that facilitate detection of the agent (e.g. fluorescent labels (Prober et al. 1987 Science 238:336-340; Albarella et al., European Patent No. 144914), chemical labels (Sheldon et al., U.S. Pat. No. 4,582,789; Albarella et al., U.S. Pat. No. 4,563,417), modified bases (Miyoshi et al., European Patent No. 119448).

Having now generally described the invention, the same will be more readily understood through reference to the following examples which are provided by way of illustration, and are not intended to be limiting of the present invention, unless specified.

EXAMPLES

Example 1

Identifying Antixenosis Type Aphid Resistance in PI594427C

Soybean breeders evaluate soybean germplasm for genetic traits that confer resistance to attack and injury by aphids. Host plant resistance is classified as antixenosis, antibiosis or tolerance. Antixenosis, also referred to as non-preference, is the ability of a plant to repel insects, causing a reduction in oviposition or feeding. Dowling, CNS (PI 548445). Jackson, PI 597727C, PI 594403 and Williams were evaluated for antixenosis type resistance. Antixenosis resistance is typical evaluated choice experiments where insects can select between at least two host plants.

PI 594427C was identified to have resistance to aphids in choice field tests conducted at Michigan State University over three field season. In the choice field tests, Dowling, CNS, Jackson, PI 597727C, PI 594403 and Williams were grown and enclosed in a single cage. Two field collected aphids were placed on each plant. Aphids were able to move freely from plant to plant, therefore the study evaluated the aphid plant preference. Plants were individually scored at 2, 3, 4, or 5 wks after infestation, depending on when symptoms were first observed. Plants were given a visual rating ranging from 0 to 4 (Table 1).

TABLE 1

Description of rating scale used for aphid resistance phenotyping

| Rating | | Symptoms |
|---|---|---|
| 0 | Very Resistant | No aphids |
| 1 | Resistant | Fewer than 100 aphids |
| 2 | Moderately Resistant | 101-300 aphids |
| 3 | Moderately Susceptible | 300-800 aphids |
| 4 | Susceptible | >800 aphids |

Each week, the plants were also assigned a damage index (DI), which is calculated using the following formula:

$$DI = \frac{\Sigma(\text{each scale} \times \text{no. of plants in the scale})}{4 \times \text{total no. of plants evaluated}} \times 100$$

A higher damage index corresponds to a more susceptible plant.

Over three years of field tests, PI 594427C consistently showed equivalent or lower aphid ratings and damage indices than known aphid resistant varieties, Jackson and Dowling (Table 2). CNS and Williams were sensitive to aphid infestation.

TABLE 2

Average soybean aphid rating and damage index for aphid-resistant and -susceptible soybean genotypes tested in triplicate in field cages over 3 years at Michigan State University.

| Line | Aphid rating (0-4) | Damage index¶ (%) |
|---|---|---|
| Dowling | 1.8 | 44 |
| CNS | 3.8 | 95 |
| Jackson | 1.9 | 48 |
| PI 594427C | 1.5 | 37 |
| PI 594403 | 2.5 | 63 |
| Williams | 3.8 | 94 |

Example 2

Identifying Antibiosis Type Aphid Resistance in PI1594427C

Host plant resistance is classified as antixenosis, antibiosis or tolerance. Antibiosis is the ability of a plant to reduce the survival, growth, or reproduction of insects that feed on it. Antibiosis is often caused by the production of toxic chemicals by the plant. Antibiosis type plant resistance is often evaluated in no-choice studies where insect are supplied a single food source. Pana, PI 594403, PI 71506, Williams, PI594403, PI 594427C, CNS, Jackson, and Dowling were evaluated for antibiosis resistance in no choice experiments.

Antibiosis resistance was identified in PI 594427C in no choice conducted at University of Illinois. Plants were grown in isolated cages in a choice situation. Three aphid nymphs were placed on each plant. The number of aphids was counted at 14, 17, and 21 days after inoculation (Table 2). Four replications were performed for each entry. Aphids were able to readily reproduce on CNS under antixenosis conditions (Table 2), but not under antibiosis conditions. The level of aphid infestation was higher and the aphid age range was broader under the antixenosis evaluation compared to aphid infestation and age range under the antibiosis evaluation. The difference in aphid infestation level and aphid maturity may account for the differences observed on CNS in the antibiosis and antixenosis evaluations. Furthermore, geographic aphid biotypes from Illinois and Michigan may account for differences in reaction on CNS.

TABLE 3

Average number of soybean aphid for aphid-resistant and aphid-susceptible soybean genotypes tested at University of Illinois.

| | No. of Aphids per Plant at: | | |
|---|---|---|---|
| Line | 14 d | 17 d | 21 d* |
| Pana | 190 | 405 | 1076a |
| PI 594403 | 142 | 497 | 603a |
| PI 71506 | 200 | 316 | 294ab |
| Williams | 126 | 251 | 236ab |
| PI 594403 | 36 | 83 | 59bc |
| PI 594427C | 20 | 17 | 12cd |
| CNS | 21 | 22 | 11cd |
| CNS | 17 | 24 | 10cd |
| Jackson | 14 | 5 | 6d |
| PI 594427C | 17 | 12 | 5d |
| Dowling | 7 | 3 | 3d |
| Dowling | 6 | 3 | 3d |

*Means followed by different letters are significantly different at 0.05 level.

Example 3

Aphid Mapping Studies

In order to map putative QTL to aphid resistance, a resistant line (PI 594427C) was crossed with a CNS or MV0031. Two mapping populations were developed to map putative QTLs linked with aphid resistance: PI594427C (aphid resistant)×MV0031 and PI594427C (aphid resistant)×CNS. $F_3$: PI594427C×MV0031 and $F_4$: PI594427C×CNS populations were evaluated for aphid resistance phenotype in enclosed cages in East Lansing, Mich. Three aphid nymphs were placed per plant and aphid density was rated at 3, 4, 5 weeks after inoculation. The rating scale was 0-5 (Table 1). Twenty-eight aphid resistant loci were identified (Table 6 and 7).

The phenotype data from week 4 evaluation was used from QTL mapping studies (Tables 4 and 5). At week 4, the aphid resistant parent, PI594427C, was rated 1.5 and the aphid sensitive parents, MV0031 and CNS, were rated 3.5 In addition to the above-described phenotyping, each population was genotyped with SNP markers: 181 polymorphic SNPs with the $F_3$: PI594427C×MV0031 population and 164 polymorphic SNPs with the $F_4$: PI594427C×CNS population. Single marker and marker regression analyses were performed to determine QTL regions conditioning aphid resistance. Tables 6 and 7 list significant associations between genomic regions and aphid resistance along with diagnostic markers.

TABLE 4

Phenotype of $F_4$: PI594427C×CNS at week 4 after inoculation.

| Aphid Rating | Number of Plants |
|---|---|
| 0.5 | 0 |
| 1 | 4 |
| 1.5 | 8 |
| 2 | 32 |
| 2.5 | 64 |
| 3 | 70 |
| 3.5 | 6 |
| 4 | 0 |
| Total (n) | 184 |

TABLE 5

Phenotype of $F_3$: PI594427C×MV0031 at week 4 after inoculation.

| Aphid Rating | Number of Plants |
|---|---|
| 0.5 | 0 |
| 1 | 2 |
| 1.5 | 5 |
| 2 | 29 |
| 2.5 | 29 |
| 3 | 88 |
| 3.5 | 30 |
| 4 | 0 |
| Total (n) | 183 |

TABLE 6

Results of markers associated with aphid resistance determined (ns = not significant)

| Population | Aphid Resistance Loci | LG | Marker | Allele | t-value* | p-value** | R-sq. value*** | Marker Interval |
|---|---|---|---|---|---|---|---|---|
| PI 594427C x CNS | 1 | J | NS0115450 | T | 3.36(P < 0.05) | 0.00118 | 8 | 38-58 cM |
| PI 594427C x MV0031 | 1 | J | NS0122151 | A | 5.51(P < 0.05) | <0.0001 | 14 | 28-48 cM |
| PI 594427C x MV0031 | 2 | E | NS0126797 | G | 2.49(P < 0.05) | 0.04961 | 3 | 30-50 cM |
| PI 594427C x CNS | 2 | E | NS0126797 | A | 2.01(P < 0.05) | ns | 3 | 30-50 cM |
| PI 594427C x CNS | 3 | E | NS0098210 | C | 2.78(P < 0.05) | 0.00741 | 5 | 76-96 cM |
| PI 594427C x CNS | 4 | E | NS0099483 | C | 2.64(P < 0.05) | 0.01348 | 5 | 111-131 cM |
| PI 594427C x MV0031 | 5 | B1 | NS0100200 | A | 2.04(P < 0.05) | ns | 2 | 44-64 cM |
| PI 594427C x CNS | 6 | N | NS0137720 | C | ns | 0.02978 | 4 | 0-10 cM |
| PI 594427C x CNS | 7 | G | NS0118422 | T | ns | 0.02406 | 4 | 77-97 cM |
| PI 594427C x MV0031 | 8 | N | NS0125467 | T | 2.03(P < 0.05) | ns | 3 | 26-46 cM |
| PI 594427C x CNS | 8 | N | NS0129030 | C | ns | 0.04662 | 4 | 15-35 cM |
| PI 594427C x CNS | 9 | N | NS0098575 | T | 2.03(P < 0.05) | 0.04894 | 3 | 97-117 cM |
| PI 594427C x MV0031 | 10 | A1 | NS0129617 | C | 2.06(P < 0.05) | 0.04753 | 4 | 0-15 cM |
| PI 594427C x MV0031 | 11 | A1 | NS0130304 | A | 2.2(P < 0.05) | ns | 3 | 33-53 cM |
| PI 594427C x CNS | 12 | D1a | NS0095317 | I | 2.51(P < 0.05) | 0.00628 | 6 | 12-32 cM |
| PI 594427C x CNS | 13 | C2 | NS0115731 | A | ns | 0.02083 | 4 | 54-74 cM |
| PI 594427C x CNS | 14 | H | NS0120346 | T | 2.28(P < 0.05) | ns | 3 | 1-13 cM |
| PI 594427C x CNS | 15 | H | NS0097165 | A | 2.03(P < 0.05) | ns | 3 | 62-82 cM |
| PI 594427C x MV0031 | 16 | D2 | NS0092748 | T | 4.44(P < 0.05) | 0.00008 | 10 | 0-18 cM |
| PI 594427C x MV0031 | 16 | D2 | NS0096662 | | 4.44 | 0.00008 | | 0-18 cM |
| PI 594427C x CNS | 16 | D2 | NS0118525 | T | 2.37(P < 0.05) | ns | 3 | 0-10 cM |
| PI 594427C x MV0031 | 17 | F | NS0099503 | T | 3.21(P < 0.05) | 0.0049 | 6 | 0-18 cM |
| PI 594427C x CNS | 18 | F | NS0123719 | A | 2.97(P < 0.05) | 0.0062 | 6 | 62-82 cM |
| PI 594427C x MV0031 | 19 | I | NS0130766 | A | 2.47(P < 0.05) | 0.02812 | 4 | 0-14 cM |
| PI 594427C x CNS | 20 | D1b | NS0121903 | C | 3.23(P < 0.05) | 0.00633 | 6 | 30-50 cM |
| PI 594427C x CNS | 21 | D1b | NS0098438 | A | 2.01(P < 0.05) | ns | 2 | 124-144 cM |
| PI 594427C x CNS | 21 | D1b | NS0114263 | C | ns | 0.04948 | 3 | 91-111 cM |
| PI 594427C x MV0031 | 22 | O | NS0124919 | C | 2.06(P < 0.05) | ns | 4 | 50-70 cM |
| PI 594427C x CNS | 23 | O | NS0124051 | C | 2.72(P < 0.05) | 0.00485 | 6 | 120-140 cM |
| PI 594427C x CNS | 24 | C1 | NS0124300 | G | 2.64(P < 0.05) | 0.02273 | 4 | 0-15 cM |
| PI 594427C x MV0031 | 25 | C1 | NS0093331 | C | 2.04(P < 0.05) | ns | 3 | 28-48 cM |
| PI 594427C x MV0031 | 26 | C1 | NS0097882 | T | 2.02(P < 0.05) | ns | 3 | 113-133 cM |
| PI 594427C x MV0031 | 26 | C1 | NS0136956 | G | ns | 0.00561 | 6 | 72-92 cM |
| PI 594427C x CNS | 27 | K | NS0098803 | T | ns | 0.02604 | 4 | 0-20 cM |
| PI 594427C x MV0031 | 28 | B2 | NS0092589 | G | 2.21(P < 0.05) | 0.03209 | 5 | 7-27 cM |
| PI 594427C x CNS | 28 | B2 | NS0103077 | D | 2.18(P < 0.05) | 0.0415 | 4 | 0-10 cM |

*Marker analysis was performed using a t-test. P-value ≦ 0.05 is significant.
**Marker analysis was performed using marker regression in MapManager QTX;
***R-squared value from marker regression in MapManager QTX

TABLE 7

Listing of SNP markers for aphid resistance loci 1-28

| Aphid Resistance Loci | Marker | Resistance Allele | SEQ ID | SEQ ID Forward Primer | SEQ ID Reverse Primer | SEQ ID VIC probe | SEQ ID FAM probe |
|---|---|---|---|---|---|---|---|
| 1 | NS0115450 | T | 81 | 1 | 2 | 121 | 122 |
| 1 | NS0122151 | A | 82 | 3 | 4 | 123 | 124 |
| 1 | NS0125096 | | 83 | 5 | 6 | 125 | 126 |
| 1 | NS0120948 | | 84 | 7 | 8 | 127 | 128 |
| 2 | NS0126797 | G | 85 | 9 | 10 | 129 | 130 |
| 3 | NS0098210 | C | 86 | 11 | 12 | 131 | 132 |
| 4 | NS0099483 | C | 87 | 13 | 14 | 133 | 134 |
| 5 | NS0100200 | A | 88 | 15 | 16 | 135 | 136 |
| 6 | NS0137720 | C | 89 | 17 | 18 | 137 | 138 |
| 7 | NS0118422 | T | 90 | 19 | 20 | 139 | 140 |
| 8 | NS0125467 | T | 91 | 21 | 22 | 141 | 142 |
| 8 | NS0129030 | C | 92 | 23 | 24 | 143 | 144 |
| 9 | NS0098575 | T | 93 | 25 | 26 | 145 | 146 |
| 10 | NS0129617 | C | 94 | 27 | 28 | 147 | 148 |
| 11 | NS0130304 | A | 95 | 29 | 30 | 149 | 150 |
| 12 | NS0095317 | I | 96 | 31 | 32 | 151 | 152 |
| 13 | NS0115731 | A | 97 | 33 | 34 | 153 | 154 |
| 14 | NS0120346 | T | 98 | 35 | 36 | 155 | 156 |
| 15 | NS0097165 | A | 99 | 37 | 38 | 157 | 158 |
| 16 | NS0092748 | T | 100 | 39 | 40 | 159 | 160 |
| 16 | NS0096662 | | 101 | 41 | 42 | 161 | 162 |
| 16 | NS0118525 | T | 102 | 43 | 44 | 163 | 164 |
| 17 | NS0099503 | T | 103 | 45 | 46 | 165 | 166 |
| 18 | NS0123719 | A | 104 | 47 | 48 | 167 | 168 |
| 19 | NS0130766 | A | 105 | 49 | 50 | 169 | 170 |
| 20 | NS0121903 | C | 106 | 51 | 52 | 171 | 172 |
| 21 | NS0098438 | A | 107 | 53 | 54 | 173 | 174 |
| 21 | NS0114263 | C | 108 | 55 | 56 | 175 | 176 |
| 22 | NS0124919 | C | 109 | 57 | 58 | 177 | 178 |
| 23 | NS0124051 | C | 110 | 59 | 60 | 179 | 180 |
| 23 | NS0118907 | | 111 | 61 | 62 | 181 | 182 |
| 24 | NS0124300 | G | 112 | 63 | 64 | 183 | 184 |
| 25 | NS0093331 | C | 113 | 65 | 66 | 185 | 186 |
| 26 | NS0097882 | T | 114 | 67 | 68 | 187 | 188 |
| 27 | NS0098803 | T | 116 | 71 | 72 | 191 | 192 |
| 28 | NS0092589 | G | 117 | 73 | 74 | 193 | 194 |
| 28 | NS0103077 | D | 118 | 75 | 76 | 195 | 196 |
| 28 | NS0100457 | | 119 | 77 | 78 | 197 | 198 |
| 28 | NS0116259 | | 120 | 79 | 80 | 199 | 200 |

SNP markers determined to be associated with region 1 are SEQ ID NO: 81 through SEQ ID NO: 84. SNP markers for region 1 are mapped to a region on linkage group J. Table 7 lists sequences for PCR amplification primers, indicated as SEQ ID NO: 1 through SEQ ID NO: 8 and probes indicated as SEQ ID NO: 121 through SEQ ID NO: 128.

A SNP marker determined to be associated with region 2 is SEQ ID NO: 85. A SNP marker for region 2 is mapped to a region on linkage group E. Table 7 lists sequences for PCR amplification primers, indicated as SEQ ID NO: 9 through SEQ ID NO: 10 and probes indicated as SEQ ID NO: 129 through SEQ ID NO: 130.

A SNP marker determined to be associated with region 3 is SEQ ID NO: 86. A SNP marker for region 3 is mapped to a region on linkage group E. Table 7 lists sequences for PCR amplification primers, indicated as SEQ ID NO: 11 through SEQ ID NO: 12 and probes indicated as SEQ ID NO: 131 through SEQ ID NO: 132.

A SNP marker determined to be associated with region 4 is SEQ ID NO: 87. A SNP marker for region 4 is mapped to a region on linkage group E. Table 7 lists sequences for PCR amplification primers, indicated as SEQ ID NO: 13 through SEQ ID NO: 14 and probes indicated as SEQ ID NO: 133 through SEQ ID NO: 134.

A SNP marker determined to be associated with region 5 is SEQ ID NO: 88. A SNP marker for region 5 is mapped to a region on linkage group B1. Table 7 lists sequences for PCR amplification primers, indicated as SEQ ID NO: 15 through SEQ ID NO: 16 and probes indicated as SEQ ID NO: 135 through SEQ ID NO: 136.

A SNP marker determined to be associated with region 6 is SEQ ID NO: 89. A SNP marker for region 6 is mapped to a region on linkage group N. Table 7 lists sequences for PCR amplification primers, indicated as SEQ ID NO: 17 through SEQ ID NO: 18 and probes indicated as SEQ ID NO: 137 through SEQ ID NO: 138.

A SNP marker determined to be associated with region 7 is SEQ ID NO: 90. A SNP marker for region 7 is mapped to a region on linkage group G. Table 7 lists sequences for PCR amplification primers, indicated as SEQ ID NO: 19 through SEQ ID NO: 20 and probes indicated as SEQ ID NO: 139 through SEQ ID NO: 140.

SNP markers determined to be associated with region 8 are SEQ ID NO: 91 through SEQ ID NO: 92. SNP markers for region 8 are mapped to a region on linkage group N. Table 7 lists sequences for PCR amplification primers, indicated as SEQ ID NO: 21 through SEQ ID NO: 24 and probes indicated as SEQ ID NO: 141 through SEQ ID NO: 144.

A SNP marker determined to be associated with region 9 is SEQ ID NO: 93. A SNP marker for region 9 is mapped to a region on linkage group N. Table 7 lists sequences for PCR amplification primers, indicated as SEQ ID NO: 25 through SEQ ID NO: 26 and probes indicated as SEQ ID NO: 145 through SEQ ID NO: 146.

A SNP marker determined to be associated with region 10 is SEQ ID NO: 94. A SNP marker for region 10 is mapped to a region on linkage group A1. Table 7 lists sequences for PCR amplification primers, indicated as SEQ ID NO: 27 through SEQ ID NO: 28 and probes indicated as SEQ ID NO: 147 through SEQ ID NO: 148.

A SNP marker determined to be associated with region 11 is SEQ ID NO: 95. A SNP marker for region 11 is mapped to a region on linkage group A1. Table 7 lists sequences for PCR amplification primers, indicated as SEQ ID NO: 29 through SEQ ID NO: 30 and probes indicated as SEQ ID NO: 149 through SEQ ID NO: 150.

A SNP marker determined to be associated with region 12 is SEQ ID NO: 96. A SNP marker for region 12 is mapped to a region on linkage group D1a. Table 7 lists sequences for PCR amplification primers, indicated as SEQ ID NO: 31 through SEQ ID NO: 32 and probes indicated as SEQ ID NO: 151 through SEQ ID NO: 152.

A SNP marker determined to be associated with region 13 is SEQ ID NO: 97. A SNP marker for region 13 is mapped to a region on linkage group C2. Table 7 lists sequences for PCR amplification primers, indicated as SEQ ID NO: 33 through SEQ ID NO: 34 and probes indicated as SEQ ID NO: 153 through SEQ ID NO: 154.

A SNP marker determined to be associated with region 14 is SEQ ID NO: 98. A SNP marker for region 14 is mapped to a region on linkage group H. Table 7 lists sequences for PCR amplification primers, indicated as SEQ ID NO: 35 through SEQ ID NO: 36 and probes indicated as SEQ ID NO: 155 through SEQ ID NO: 156.

A SNP marker determined to be associated with region 15 is SEQ ID NO: 99. A SNP marker for region 15 is mapped to a region on linkage group H. Table 7 lists sequences for PCR amplification primers, indicated as SEQ ID NO: 37 through SEQ ID NO: 38 and probes indicated as SEQ ID NO: 157 through SEQ ID NO: 158.

SNP markers determined to be associated with region 16 are SEQ ID NO: 100 through SEQ ID NO: 102. SNP markers for region 16 are mapped to a region on linkage group D2. Table 7 lists sequences for PCR amplification primers, indicated as SEQ ID NO: 39 through SEQ ID NO: 42 and probes indicated as SEQ ID NO: 159 through SEQ ID NO: 164.

A SNP marker determined to be associated with region 17 is SEQ ID NO: 103. A SNP marker for region 17 is mapped to a region on linkage group F. Table 7 lists sequences for PCR amplification primers, indicated as SEQ ID NO: 45 through SEQ ID NO: 46 and probes indicated as SEQ ID NO: 165 through SEQ ID) NO: 166.

A SNP marker determined to be associated with region 18 is SEQ ID NO: 104. A SNP marker for region 18 is mapped to a region on linkage group F. Table 7 lists sequences for PCR amplification primers, indicated as SEQ ID NO: 47 through SEQ ID NO: 48 and probes indicated as SEQ ID NO: 167 through SEQ ID NO: 168.

A SNP marker determined to be associated with region 19 is SEQ ID NO: 105. A SNP marker for region 19 is mapped to a region on linkage group I. Table 7 lists sequences for PCR amplification primers, indicated as SEQ ID NO: 49 through SEQ ID NO: 50 and probes indicated as SEQ ID NO: 169 through SEQ ID NO: 170.

A SNP marker determined to be associated with region 20 is SEQ ID NO: 106. A SNP marker for region 20 is mapped to a region on linkage group D1b. Table 7 lists sequences for PCR amplification primers, indicated as SEQ ID NO: 51 through SEQ ID NO: 52 and probes indicated as SEQ ID NO: 171 through SEQ ID NO: 172.

SNP markers determined to be associated with region 21 are SEQ ID NO: 107 through SEQ ID NO: 108. SNP markers for region 21 are mapped to a region on linkage group D1b. Table 7 lists sequences for PCR amplification primers, indicated as SEQ ID NO: 53 through SEQ ID NO: 56 and probes indicated as SEQ ID NO: 173 through SEQ ID NO: 176.

A SNP marker determined to be associated with region 22 is SEQ ID NO: 109. A SNP marker for region 22 is mapped to a region on linkage group O. Table 7 lists sequences for PCR amplification primers, indicated as SEQ ID NO: 57 through SEQ ID NO: 58 and probes indicated as SEQ ID NO: 177 through SEQ ID NO: 178.

SNP markers determined to be associated with region 23 are SEQ ID NO: 110 SEQ ID NO: 11. A SNP marker for region 23 is mapped to a region on linkage group O. Table 7 lists sequences for PCR amplification primers, indicated as SEQ ID NO: 59 through SEQ ID NO: 62 and probes indicated as SEQ ID NO: 179 through SEQ ID NO: 180.

A SNP marker determined to be associated with region 23 is SEQ ID NO: 111. A SNP marker for region 23 is mapped to a region on linkage group C1. Table 7 lists sequences for PCR amplification primers, indicated as SEQ ID NO: 61 through SEQ ID NO: 62 and probes indicated as SEQ ID NO: 181 through SEQ ID NO: 182.

A SNP marker determined to be associated with region 24 is SEQ ID NO: 112. A SNP marker for region 24 is mapped to a region on linkage group C1. Table 7 lists sequences for PCR amplification primers, indicated as SEQ ID NO: 63 through SEQ ID NO: 64 and probes indicated as SEQ ID NO: 183 through SEQ ID NO: 184.

A SNP marker determined to be associated with region 25 is SEQ ID NO: 113. A SNP marker for region 25 is mapped to a region on linkage group C1. Table 7 lists sequences for PCR amplification primers, indicated as SEQ ID NO: 65 through SEQ ID NO: 66 and probes indicated as SEQ ID NO: 185 through SEQ ID NO: 186.

SNP markers determined to be associated with region 26 are SEQ ID NO: 114 through SEQ ID NO: 116. SNP markers for region 26 are mapped to a region on linkage group C1. Table 7 lists sequences for PCR amplification primers, indicated as SEQ ID NO: 67 through SEQ ID NO: 70 and probes indicated as SEQ ID NO: 187 through SEQ ID NO: 190.

A SNP marker determined to be associated with region 27 is SEQ ID NO: 116. A SNP marker for region 27 is mapped to a region on linkage group K. Table 7 lists sequences for PCR amplification primers, indicated as SEQ ID NO: 71 through SEQ ID NO: 72 and probes indicated as SEQ ID NO: 191 through SEQ ID NO: 192.

A SNP marker determined to be associated with region 28 is SEQ ID NO: 117. SNP markers for region 28 are mapped to a region on linkage group B2. Table 7 lists sequences for PCR amplification primers, indicated as SEQ ID NO: 73 through SEQ ID NO: 80 and probes indicated as SEQ ID NO: 193 through SEQ ID NO: 200.

Example 4

Oligonucleotide Hybridization Probes Useful for Detecting Soybean Plants with Aphid Resistance Loci Oligonucleotides can also be used to detect or type the polymorphisms associated with aphid resistance disclosed herein by hybridization-based SNP detection methods. Oligonucleotides capable of hybridizing to isolated nucleic acid sequences which include the polymorphism are provided. It is within the skill of the art to design assays with experimentally determined stringency to discriminate between the allelic states of the polymorphisms presented herein. Exemplary assays include Southern blots, Northern blots, microarrays, in situ hybridization, and other methods of polymorphism detection based on hybridization Exemplary oligonucleotides for use in hybridization-based SNP detection are provided in Table 8. These oligonucleotides can be detectably labeled with radioactive labels, fluorophores, or other chemiluminescent means to facilitate detection of hybridization to samples of genomic or amplified nucleic acids derived from one or more soybean plants using methods known in the art.

TABLE 8

Oligonucleotide Hybridization Probes

| Marker | Marker SEQ ID | SNP Position | Hybridization Probe | SEQ ID |
|---|---|---|---|---|
| NS0122151 | 82 | 62 | CCTTGCAAGTCATGCT | 201 |
| NS0122151 | 82 | 62 | CCTTGCATGTCATGCT | 202 |
| NS0125096 | 83 | 139 | AAGTTTATGATTTGAA | 203 |
| NS0125096 | 83 | 139 | AAGTTTAAGATTTGAA | 204 |
| NS0120948 | 84 | 109 | ATTCTTCAGCATGATC | 205 |
| NS0120948 | 84 | 109 | ATTCTTCTGCATGATC | 206 |
| NS0092748 | 100 | 289 | TACCTCTAAAACTTGT | 207 |
| NS0092748 | 100 | 289 | TACCTCTTAAACTTGT | 208 |
| NS0118907 | 111 | 449 | CTCCAACCTATGATTG | 209 |
| NS0118907 | 111 | 449 | CTCCAACATATGATTG | 210 |
| NS0092589 | 117 | 126 | AGCCATCACAAGGAAA | 211 |
| NS0092589 | 117 | 126 | AGCCATCATAAGGAAA | 212 |
| NS0100457 | 119 | 34 | TTGGTCCTGCCGGTAA | 213 |
| NS0100457 | 119 | 34 | TTGGTCCCGCCGGTAA | 214 |
| NS0116259 | 120 | 216 | TGATAATGACTCCTGA | 215 |
| NS0116259 | 120 | 216 | TGATAATAACTCCTGA | 216 |

Example 5

Oligonucleotide Probes Useful for Detecting Soybean Plants with Aphid Resistance Loci by Single Base Extension Methods Oligonucleotides can also be used to detect or type the polymorphisms associated with Soybean aphid resistance disclosed herein by single base extension (SBE)-based SNP detection methods. Exemplary oligonucleotides for use in SBE-based SNP detection are provided in Table 9. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 7 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

TABLE 9

Probes (extension primers) for Single Base Extension (SBE) assays.

| Marker | Marker SEQ ID | SNP Position | Probe (SBE) | SEQ ID |
|---|---|---|---|---|
| NS0122151 | 82 | 62 | AGTAGTTACTCCCTTGC | 217 |
| NS0125096 | 83 | 139 | TTCCAAAACTCAAGTTT | 218 |
| NS0120948 | 84 | 109 | GTCTGATTAATATTCTT | 219 |
| NS0092748 | 100 | 289 | GCATTCCTCAATACCTC | 220 |
| NS0118907 | 111 | 449 | AAAGAGAAAAGCTCCAA | 221 |
| NS0092589 | 117 | 126 | GGCCAATAAAAGCCAT | 222 |
| NS0100457 | 119 | 34 | GGGAGCTAGATTTGGTC | 223 |
| NS0116259 | 120 | 216 | TTTAATCAACATGATAA | 224 |

Example 6

Confirmation of Selected Aphid Resistance Alleles

Forty soybean breeding lines were screened for antibiosis in a no-choices field study. Ten plants of each breeding line were planted in a plot. Individual plots were covered by a small insect cage. The cages were inoculated soybean aphids when the soybean plants reached the VI stage. The plants were rated weekly as described in Table 1. The plants were assigned a damage index (DI) each week. Table 8 listed the average DI rating for soybean lines with various aphid resistance alleles.

In addition, the forty lines were screened for antibiosis in a no-choice greenhouse study. Several plants of each of the forty soybean breeding lines were cultivated in a greenhouse. Leaves were excised from each plant and inoculated with 2 soybean aphids in closed container. The number of aphids on each leaf was counted after seven days. Table 10 listed the average number of aphids on soybean lines with various aphid resistance alleles.

TABLE 10

Confirmation of aphid resistance alleles 1, 16, 23, and 28. Soybean lines were screened for antibiosis to soybean aphid in no-choice greenhouse and field experiments.

| | Homozygous for Resistance Allele | | | Homozygous for Susceptible Allele | | |
|---|---|---|---|---|---|---|
| Aphid Resistance Locus | No. Plants | Greenhouse No. aphids | Field Damage Index | No. Plants | Greenhouse No. aphids | Field Damage Index |
| 1 | 21 | 35 | 36 | 18 | 49 | 88 |
| 16 | 14 | 38 | 90 | 26 | 45 | 95 |
| 1 + 16 | 9 | 33 | 32 | 13 | 49 | 88 |
| 23 | 12 | 45 | 94 | 28 | 48 | 93 |
| 1 + 23 | 9 | 31 | 34 | 15 | 50 | 92 |
| 1 + 28 | 6 | 28.1 | 35.9 | 11 | 45 | 95 |
| 1 + 16 + 23 | 6 | 30 | 41 | 10 | 48 | 93 |
| 1 + 23 + 28 | 4 | 29 | 43 | 10 | 41 | 92 |
| 1 + 16 + 28 | 4 | 29 | 43 | 6 | 47 | 93 |
| 1 + 16 + 23 + 28 | 3 | 26 | 47 | 3 | 46 | 94 |

| Check Varieties | No. Plants | Greenhouse No. aphids | Field Damage Index |
|---|---|---|---|
| CNS | 25 | 28.2 | 100.0 |
| PI594427C | 19 | 20.8 | 25.0 |
| Jackson | 25 | 32.4 | 21.7 |
| Dowling | 9 | 20.8 | — |
| Williams | 16 | 59.4375 | — |

Aphid resistance allele 1 conferred aphids resistance in both the no-choice field and greenhouse tests. In addition, aphid resistance locus 16 conferred resistance in no-choice field tests. Moreover, aphid resistance allele 23 enhanced the aphid resistance conferred by aphid resistance allele 1. Similarly, aphid resistance allele 28 enhanced the aphid resistance conferred by aphid resistance allele 1. Soybean plant with three aphid resistance alleles had a higher level of aphid resistance compared soybean plants with one or two resistance alleles. Furthermore, soybean plants with four aphid resistance alleles possessed the highest level of aphids resistance.

Host plant resistance management methods may fall into three categories: (1) deploying single resistance alleles sequentially, (2) deploying multiple varieties with difference single resistance alleles through a seed mixtures or crop rotation, (3) stacking or combining different resistance allele into a single soybean line. Soybean plants may be bred for aphid resistance alleles 1, 2, 3, 4, 5, 6, 7, 8, 9, 10, 11, 12, 13, 14, 15, 16, 17, 18, 19, 20, 21, 22, 23, 24, 25, 26, 27, 28 singly or in combination depending on the aphid pressure of the geographic region and host plant resistance management plan.

Having illustrated and described the principles of the present invention, it should be apparent to persons skilled in the art that the invention can be modified in arrangement and detail without departing from such principles. We claim all modifications that are within the spirit, scope and concept of the appended claims.

We claim:

1. A method of introgressing an allele into a soybean plant comprising:
    A) Providing a population of soybean plants,
    B) Genotyping at least one soybean plant in the population with respect to a soybean genomic nucleic acid marker selected from the group consisting of SEQ ID NO: 81, SEQ ID NO: 82, SEQ ID NO: 83, and SEQ ID NO: 84, wherein said nucleic acid markers are indicative of an allele conferring aphid resistance in a soybean plant,
    C) Selecting at least one soybean plant from the population based upon the presence of at least one of said genomic nucleic acid markers.

2. The method according to claim 1, wherein said selected soybean plants exhibit at least partial resistance to aphids.

3. The method according to claim 1, wherein said selected soybean plants exhibit at least substantial resistance to aphids.

4. The method of claim 1, wherein genotyping further comprises an assay which is selected from the group consisting of single base extension (SBE), allele-specific primer extension sequencing (ASPE), DNA sequencing, RNA sequencing, micro-array based analyses, universal PCR, allele specific extension, hybridization, mass spectrometry, ligation, extension-ligation, and Flap-Endonuclease-mediated assays.

5. The method of claim 1 wherein the soybean genomic nucleic acid marker selected from the group consisting of SEQ ID NO: 81 and SEQ ID NO: 82.

6. A method of introgressing an allele into a soybean plant comprising:
    A) crossing at least one aphid resistant soybean plant with at least one aphid sensitive soybean plant in order to form a segregating population,
    B) screening said segregating population with one or more nucleic acid markers to determine if one or more soybean plants from said segregating population contains an aphid resistant locus comprising SEQ ID NO: 81, SEQ ID NO: 82, SEQ ID NO: 83, and SEQ ID NO: 84.

7. The method according to claim 6, wherein at least one of said one or more nucleic acid markers is located within 30 cM of said resistant locus.

8. The method according to claim 6, wherein at least one of said one or more markers is located within 20 cM of said resistant locus.

9. The method according to claim 6, wherein at least one of said one or more nucleic acid markers is located within 2 cM of said resistant locus.

10. The method according to claim 6, wherein at least one of said one or more nucleic acid markers is located within 1 cM of said resistant locus.

11. A method of identifying an aphid resistance allele in a soybean plant comprising detecting a locus associated with aphid resistance with a SNP marker selected from the group consisting of SEQ ID NO: 81, SEQ ID NO: 82, SEQ ID NO: 83, and SEQ ID NO: 84.

* * * * *